(12) United States Patent
Hill et al.

(10) Patent No.: US 8,349,571 B2
(45) Date of Patent: Jan. 8, 2013

(54) HIGH CONTENT SCREENING

(75) Inventors: Stephen John Hill, Nottingham (GB);
Barrie Kellam, Nottingham (GB);
Stephen John Briddon, Nottingham (GB)

(73) Assignee: Cellaura Technologies Limited, Nottingham (GB)

( * ) Notice: Subject to any disclaimer, the term of this patent is extended or adjusted under 35 U.S.C. 154(b) by 968 days.

(21) Appl. No.: 11/576,035

(22) PCT Filed: Sep. 26, 2005

(86) PCT No.: PCT/GB2005/003709
§ 371 (c)(1),
(2), (4) Date: Dec. 15, 2008

(87) PCT Pub. No.: WO2006/032926
PCT Pub. Date: Mar. 30, 2006

(65) Prior Publication Data
US 2009/0093001 A1    Apr. 9, 2009

(30) Foreign Application Priority Data

Sep. 24, 2004  (GB) .................................. 0421285.8

(51) Int. Cl.
*G01N 33/53* (2006.01)
*G01N 31/00* (2006.01)
(52) U.S. Cl. ......... 435/7.21; 435/4; 435/7.1; 435/287.9; 436/501; 436/518; 530/300; 530/350
(58) Field of Classification Search .................. None
See application file for complete search history.

(56) References Cited

U.S. PATENT DOCUMENTS

| 2002/0182655 A1 | 12/2002 | Kostenis et al. |
| 2006/0172281 A1 | 8/2006 | Schutz et al. |

FOREIGN PATENT DOCUMENTS

| WO | WO 97/20952 | 6/1997 |
| WO | WO 98/02571 | 1/1998 |
| WO | WO 02/33102 A1 | 4/2002 |
| WO | WO 02/095400 A3 | 11/2002 |
| WO | WO 04/001418 A2 | 12/2003 |
| WO | WO 2004/016766 A3 | 2/2004 |
| WO | WO 2004/068116 A3 | 8/2004 |
| WO | WO 2004/088312 A2 | 10/2004 |

OTHER PUBLICATIONS

Cordeaux et al. (The British Pharmacological Society, 016P University of Surrey Summer Meeting Jun. 2003).*
International Search Report for PCT/GB2005/003709, Sep. 26, 2005.
UK Search Report for GB0421285.8, Jul. 22, 2005.
Conway, B.R. et al., "The Use of Biosensors to Study GPCR Function: Applications for High-Content Screening", Receptors and Channels, 2002, 8:331-341.
Yan et al., "Cell-Based High-Throughput Screening Assay System for Monitoring G Protein-Coupled Receptor Activation Using β-Galactosidase Ezyme Complementation Technology", Journal of Biomolecular Screening, vol. 7, 2002, pp. 451-459.
Oakley, R. H. et al., "The Cellular Distribution of Fluorescently Labeled Arrestins Provides a Robust, Sensitive, and Universal Assay for Screening G Protein-Coupled Receptors", Assay and Drug Development Technologies, vol. 1, No. 1-1, 2002, pp. 21-30.
Briddon, S. J. et al., "Quantitative analysis of the formation and diffusion of $A_1$-adenosine receptor-antagonist complexes in single living cells", PNAS, 2004, vol. 101, No. 13, pp. 4673-4678.
Pramanik, A., "Ligand-Receptor Interactions in Live Cells by Fluorescence Correlation Spectroscopy", Current Pharmaceutical Biotechnology, 2004, pp. 205-212.

* cited by examiner

*Primary Examiner* — Lisa Cook
(74) *Attorney, Agent, or Firm* — Andrus, Sceales, Starke & Sawall, LLP

(57) ABSTRACT

A high content screening (HCS) assay for rapidly screening one or more compounds to determine functional response or pharmacological properties thereof, comprising: i) priming a cell or cell material with a sensor for a biological response; ii) contacting the compound(s) to be tested with the primed cell or cell material or contacting a cell or cell material which has been contacted with the compound(s) with the primed cell or cell material; iii) simultaneously or subsequently contacting with a fluorescent agonist or a fluorescent neutral antagonist wherein the binding of the fluorescent agonist or antagonist and its associated biological response are detected or monitored in the same cell and are distinct allowing separate readout.

29 Claims, 85 Drawing Sheets

Figure 2:
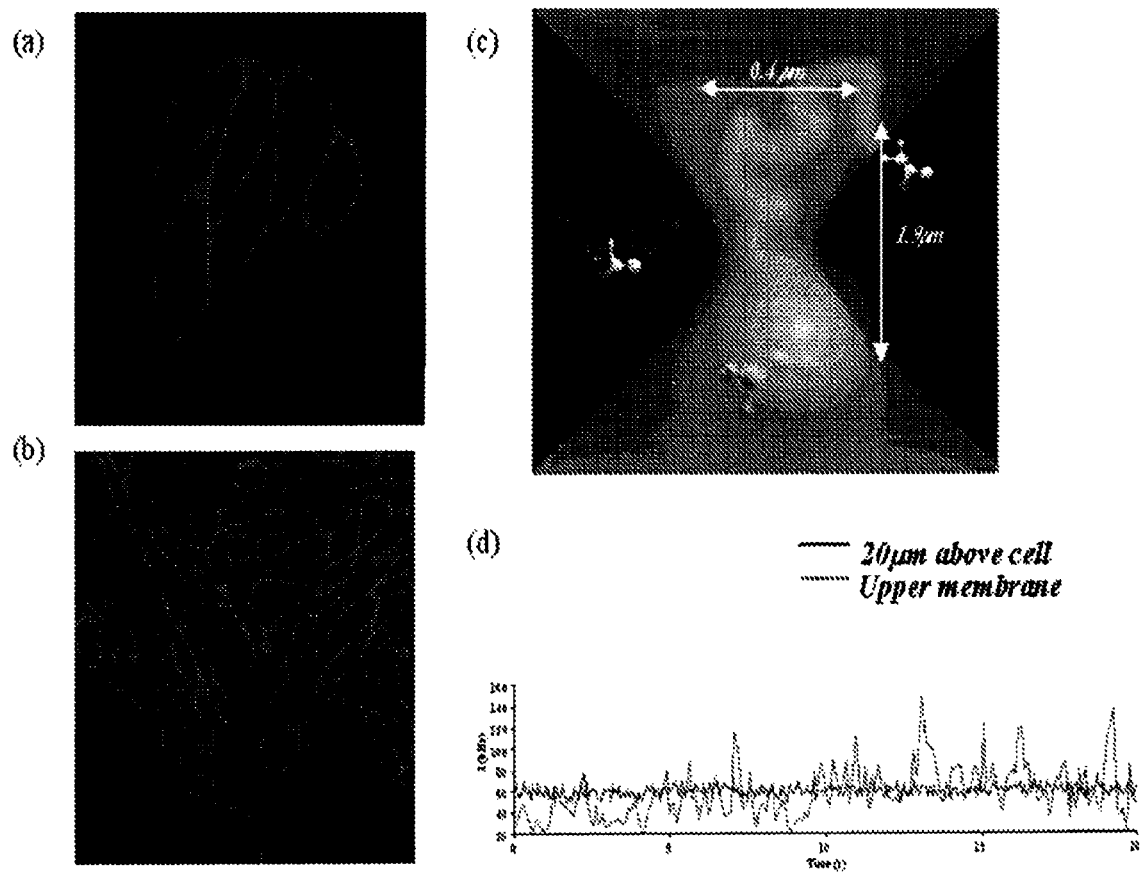

FIG. 1.1
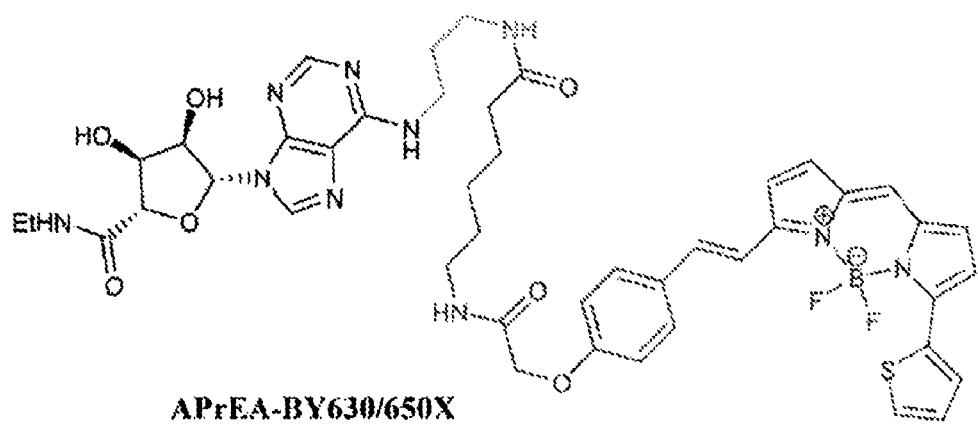
APrEA-BY630/650X
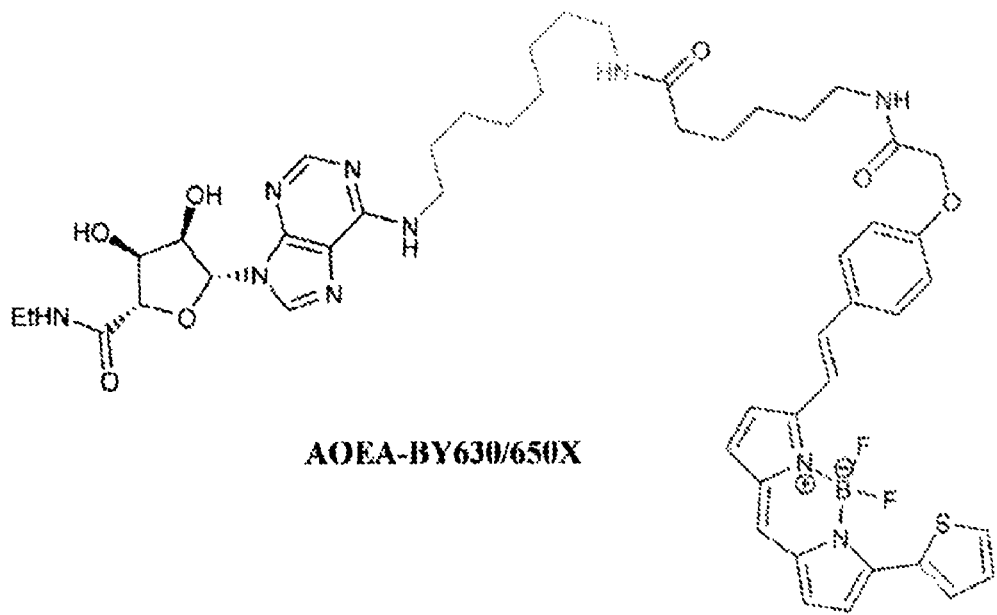
AOEA-BY630/650X

FIG. 1.2
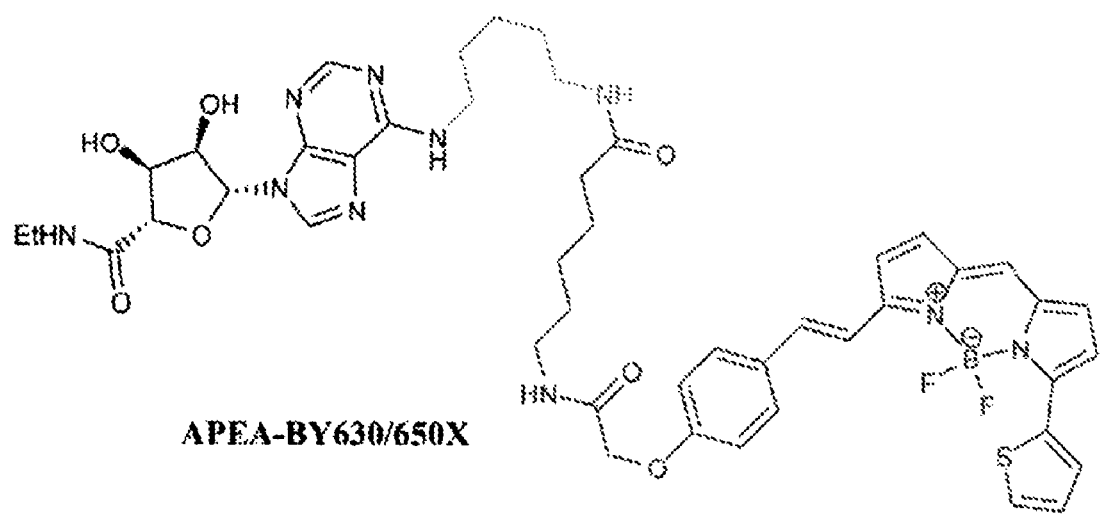
APEA-BY630/650X
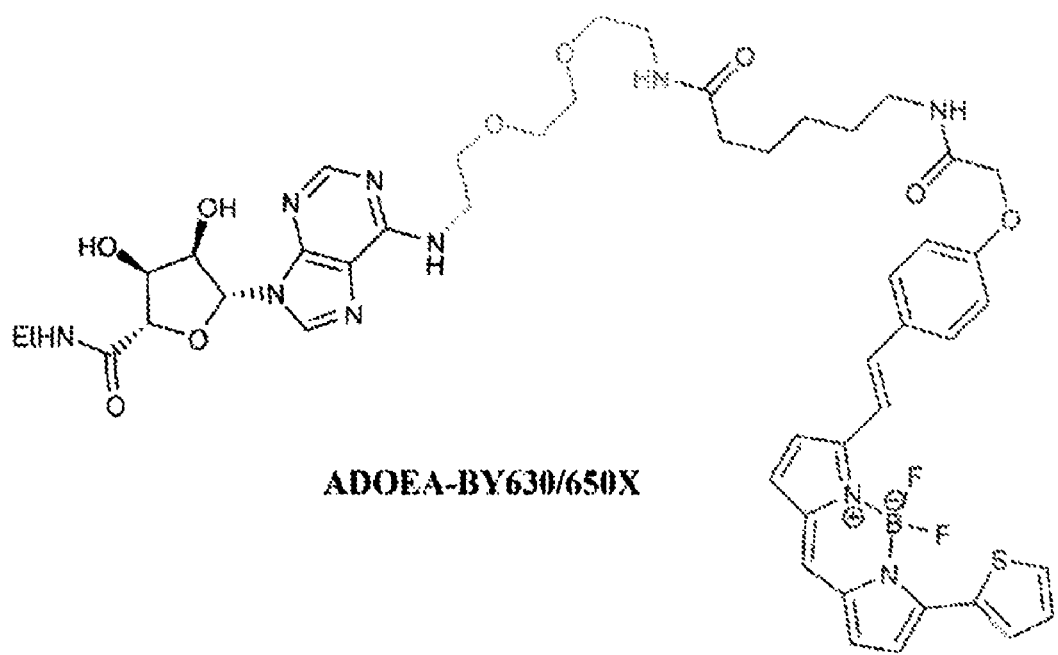
ADOEA-BY630/650X

FIG. 1.3
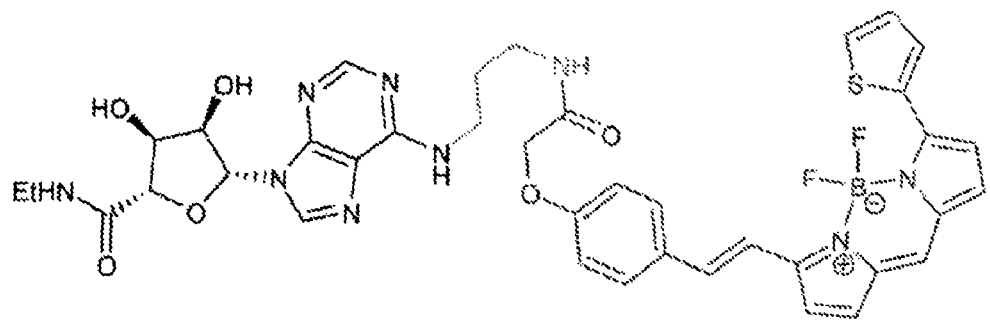
APrEA-BY630
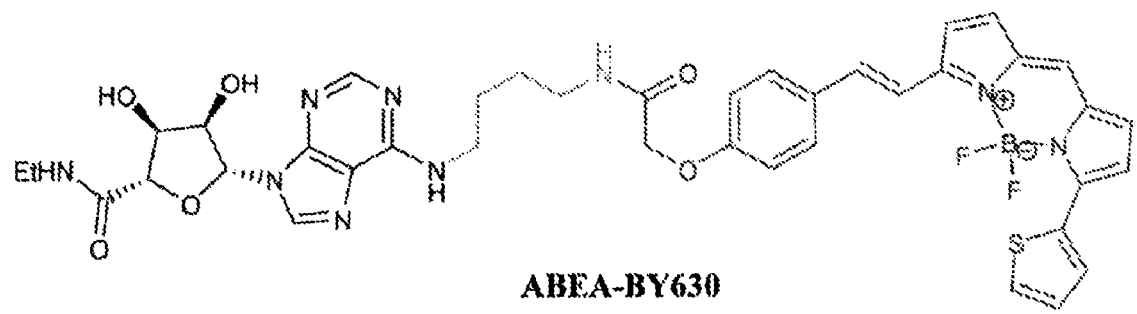
ABEA-BY630
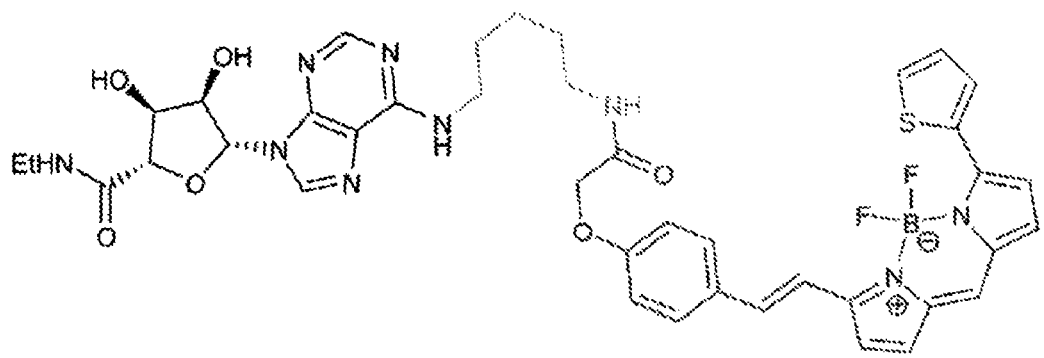
APEA-BY630

FIG. 1.4
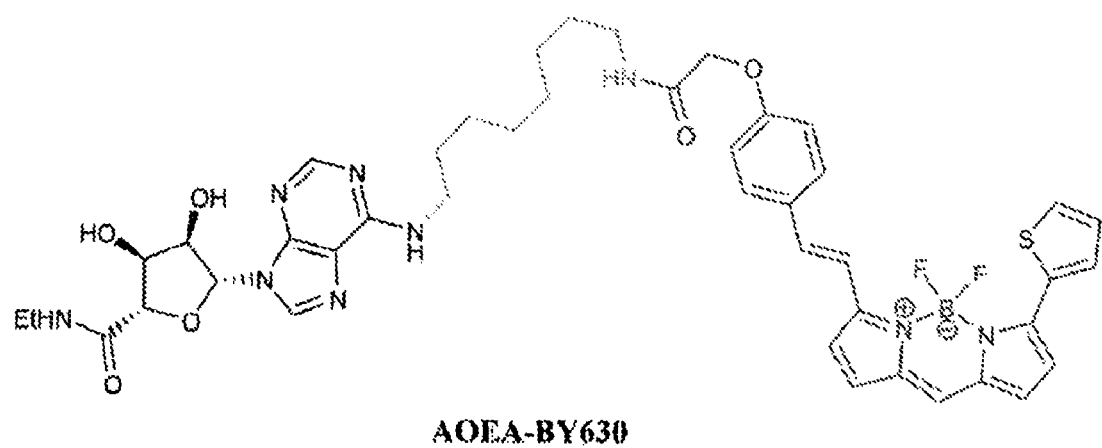
AOEA-BY630
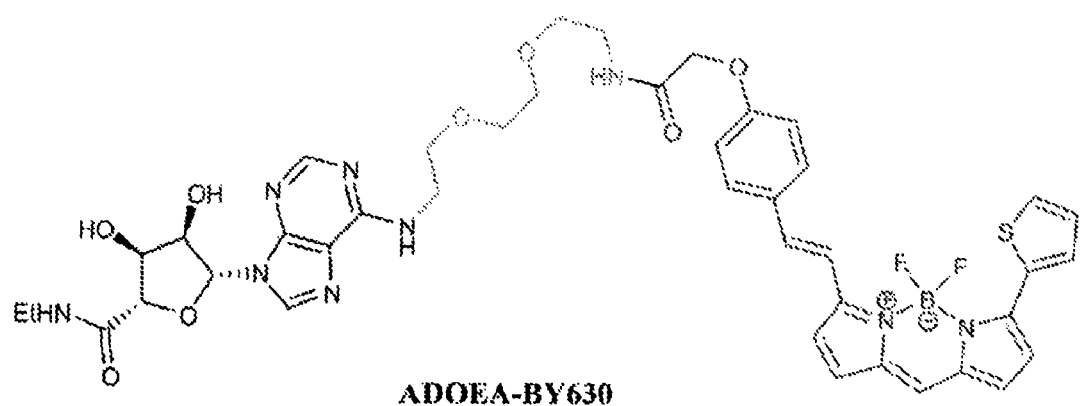
ADOEA-BY630

FIG. 1.5
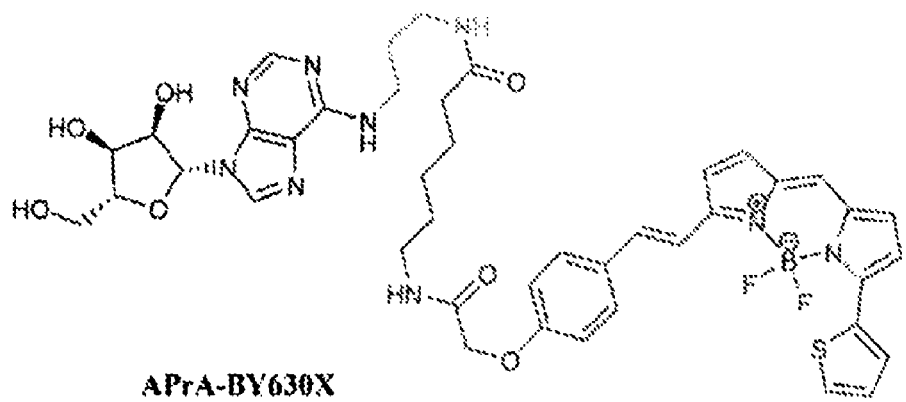
APrA-BY630X
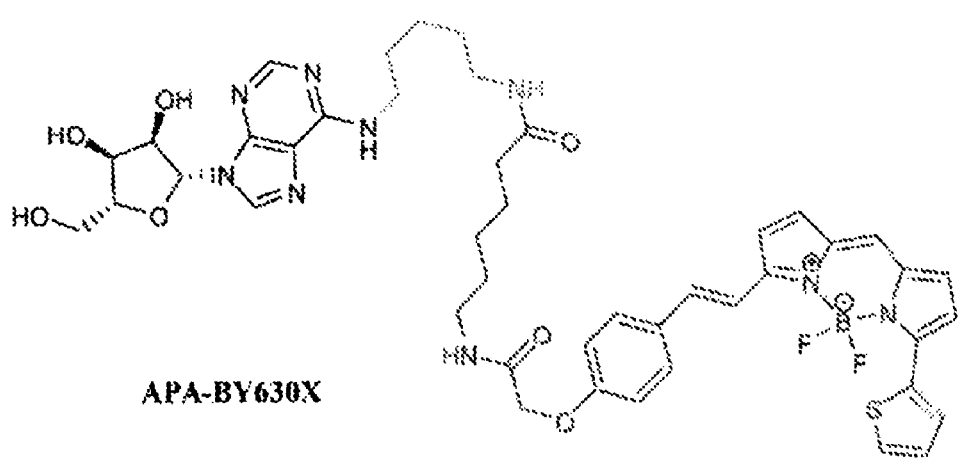
APA-BY630X
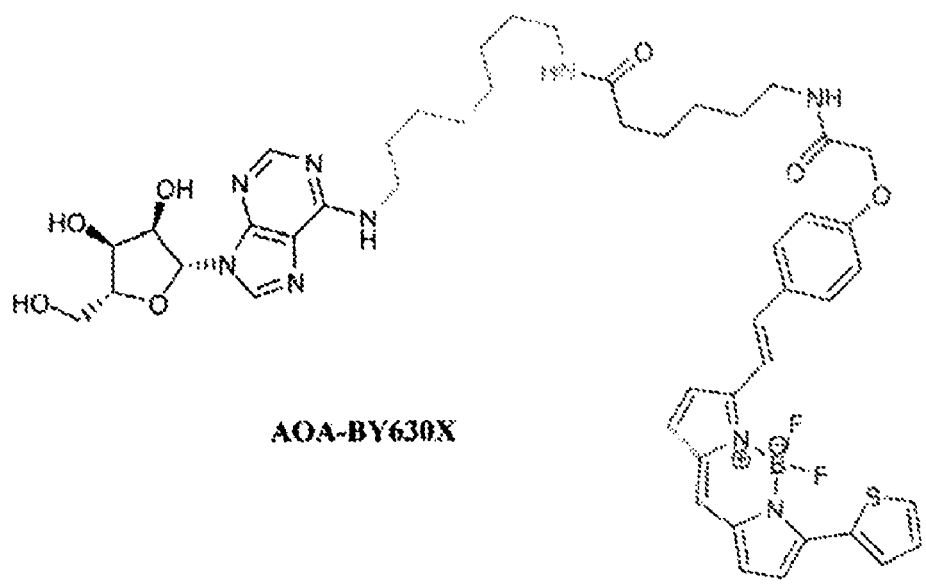
AOA-BY630X

FIG. 1.6
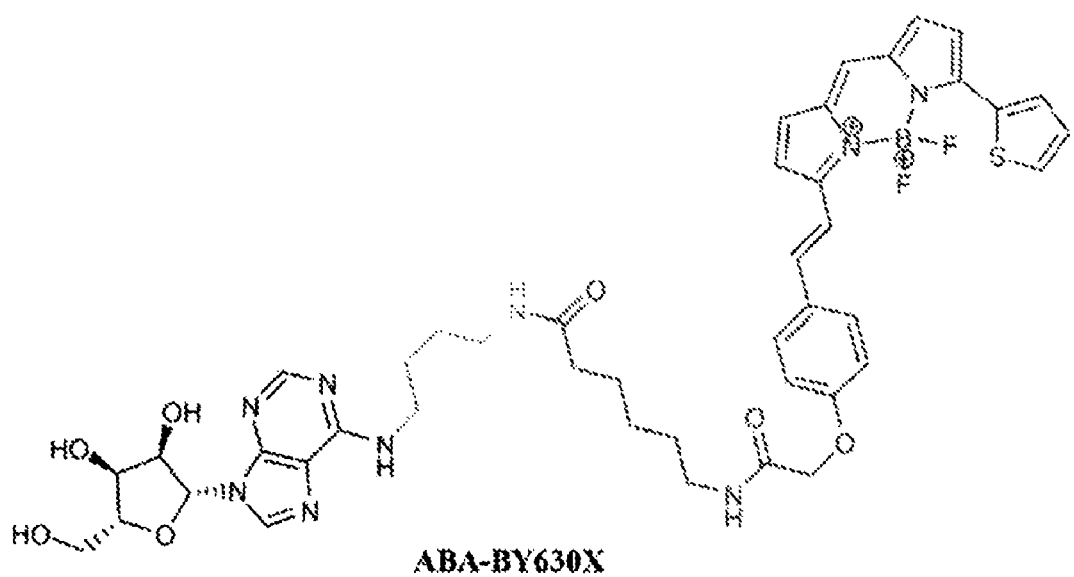
ABA-BY630X
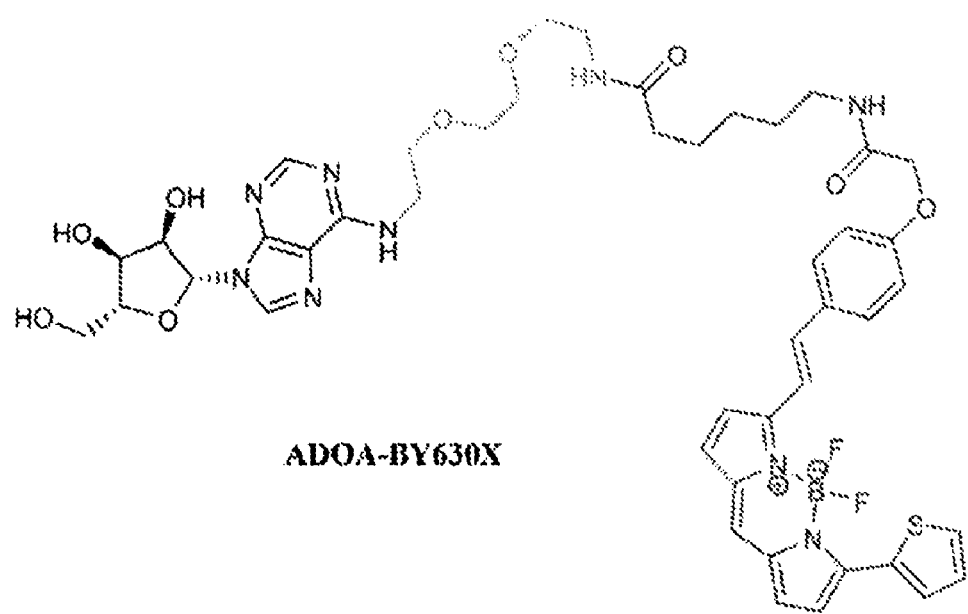
ADOA-BY630X

FIG. 1.7
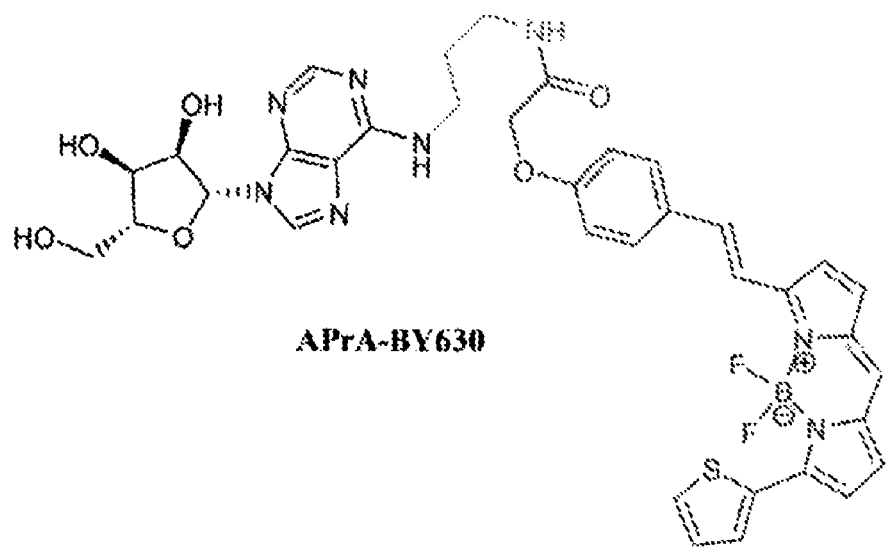
APrA-BY630
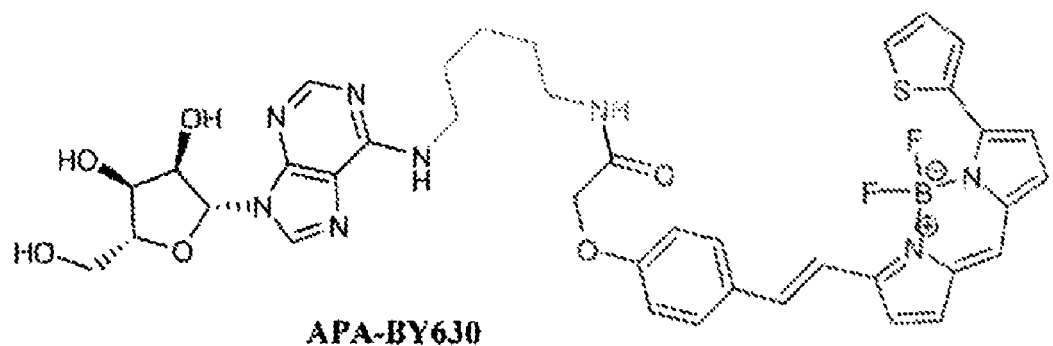
APA-BY630
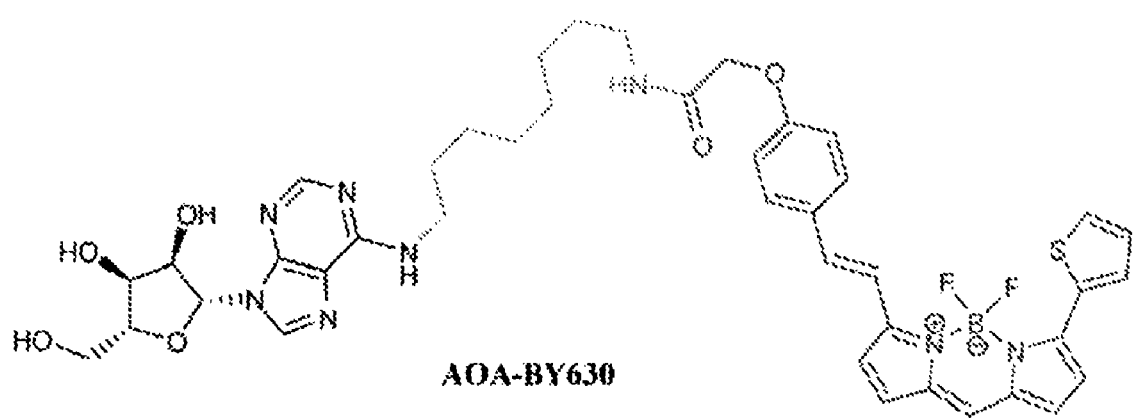
AOA-BY630

FIG. 1.8
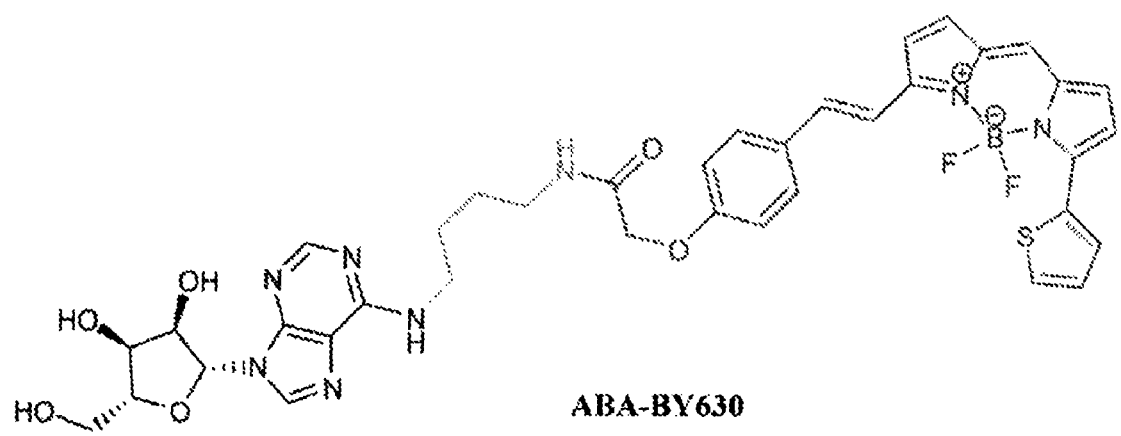
ABA-BY630
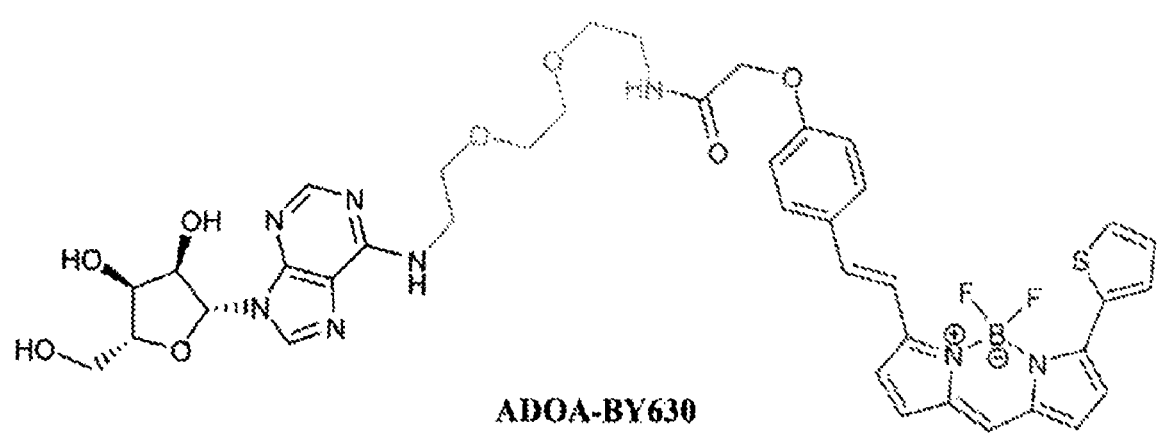
ADOA-BY630

FIG. 1.9
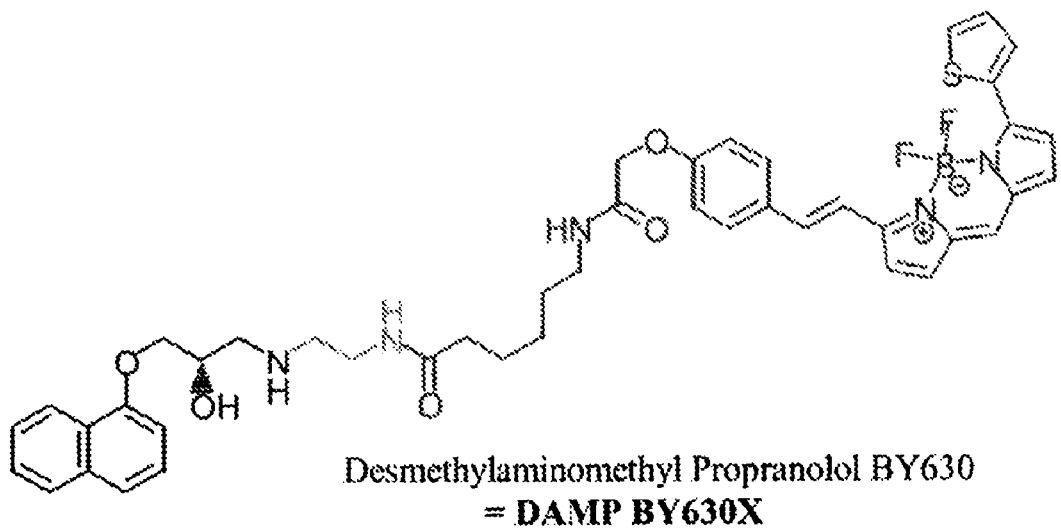
Desmethylaminomethyl Propranolol BY630
= DAMP BY630X
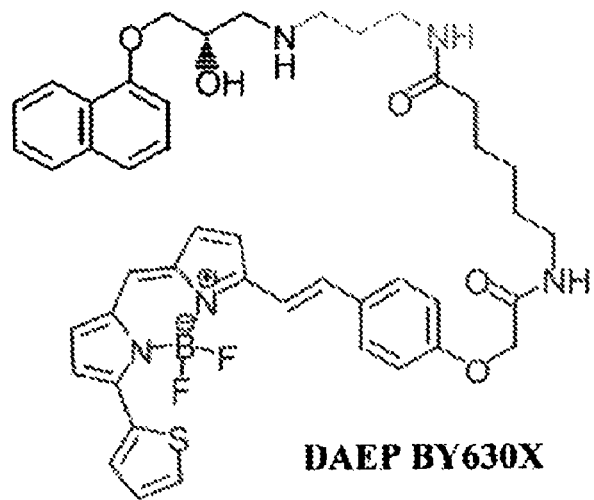
DAEP BY630X
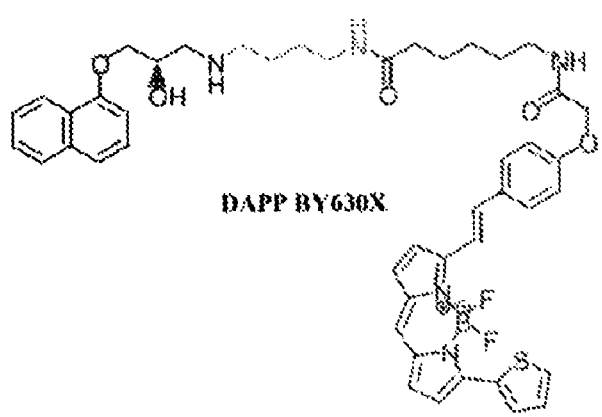
DAPP BY630X

FIG. 1.10
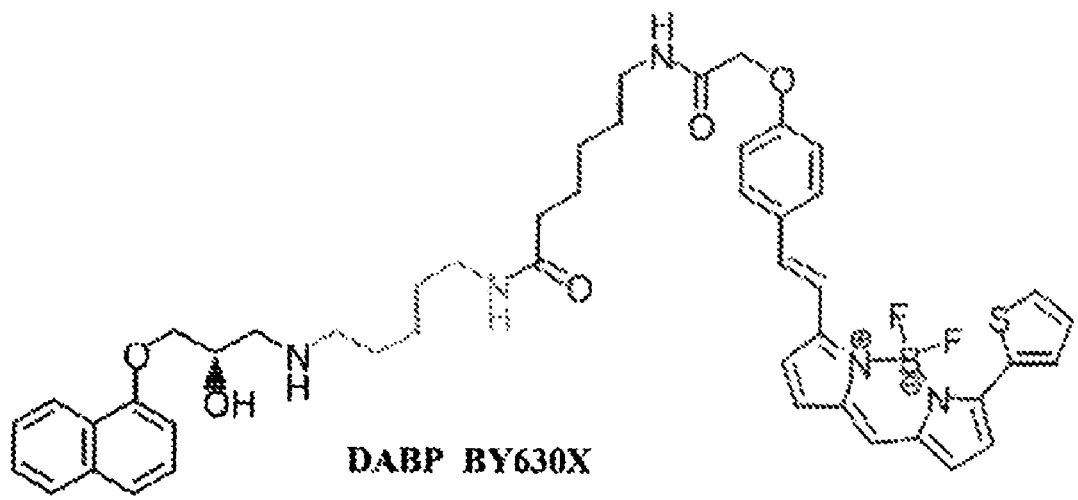
DABP BY630X
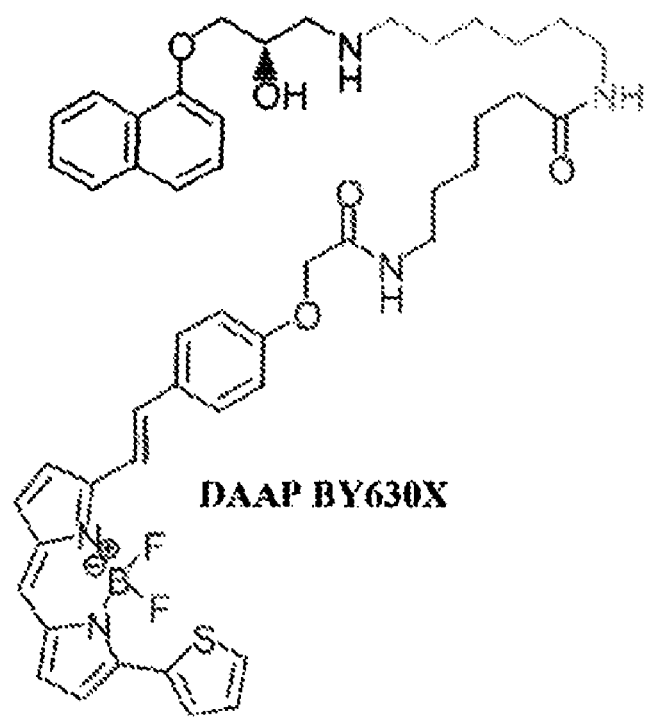
DAAP BY630X

FIG. 1.11
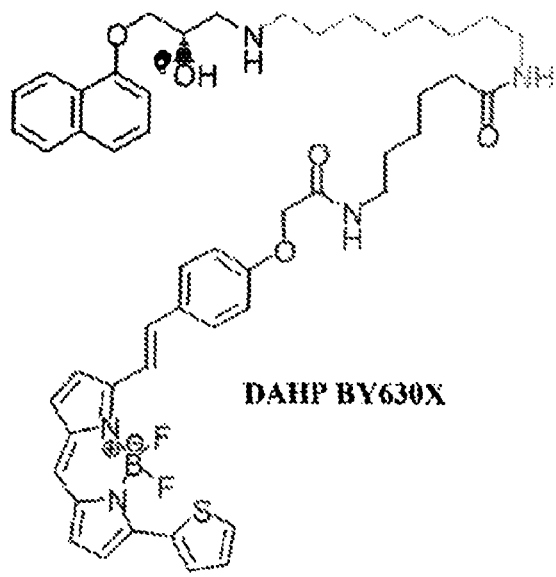
DAHP BY630X
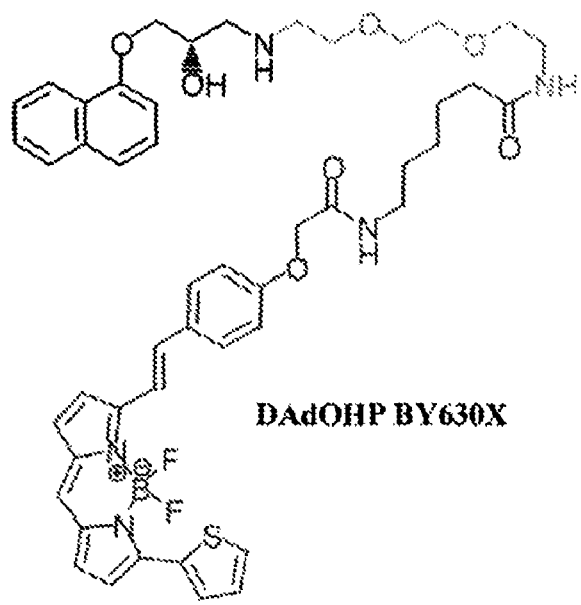
DAdOHP BY630X

FIG. 1.12
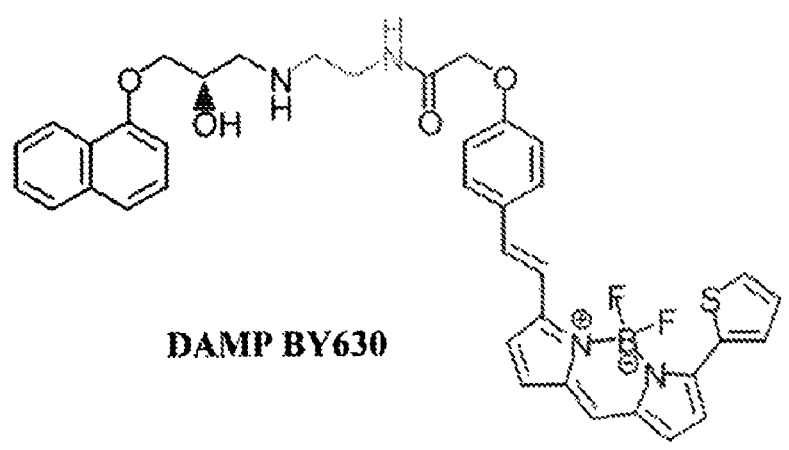
DAMP BY630
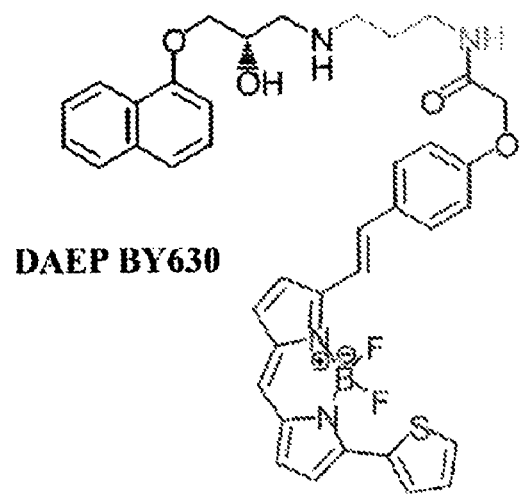
DAEP BY630
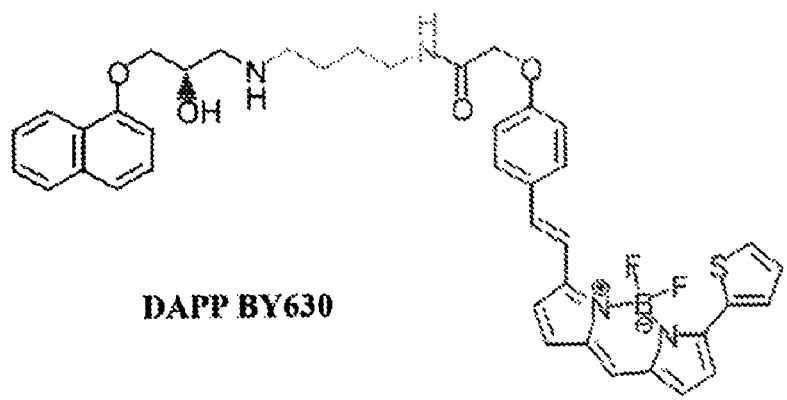
DAPP BY630

FIG. 1.13
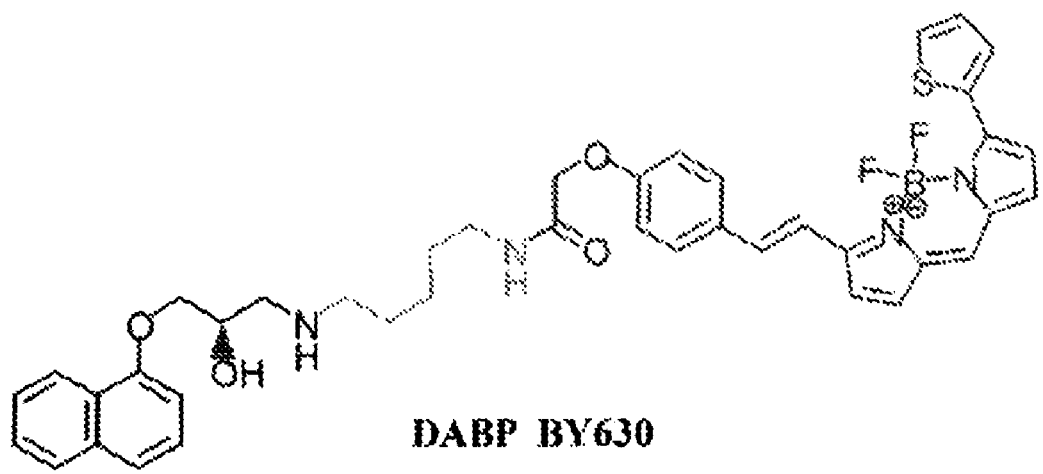
DABP BY630
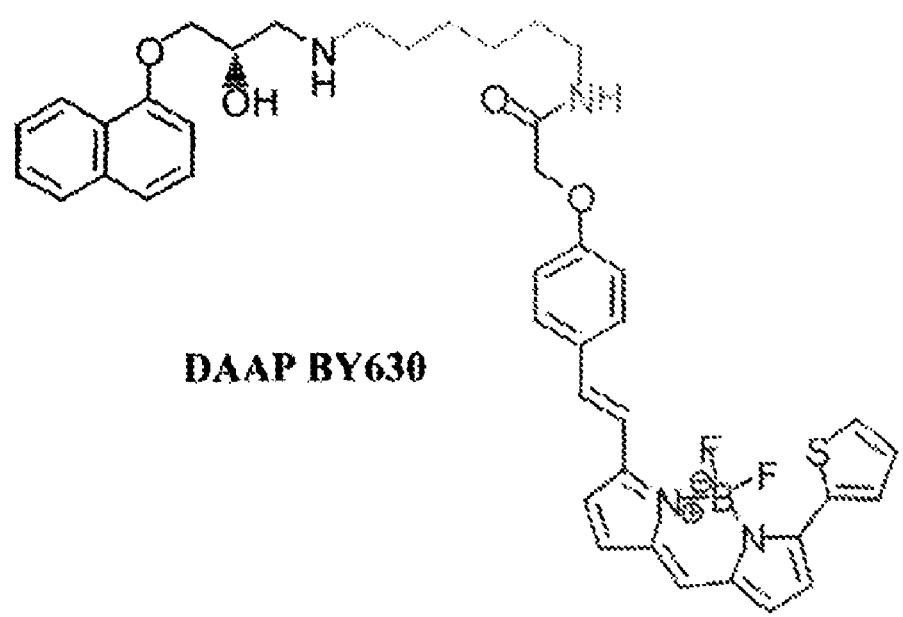
DAAP BY630

FIG. 1.14
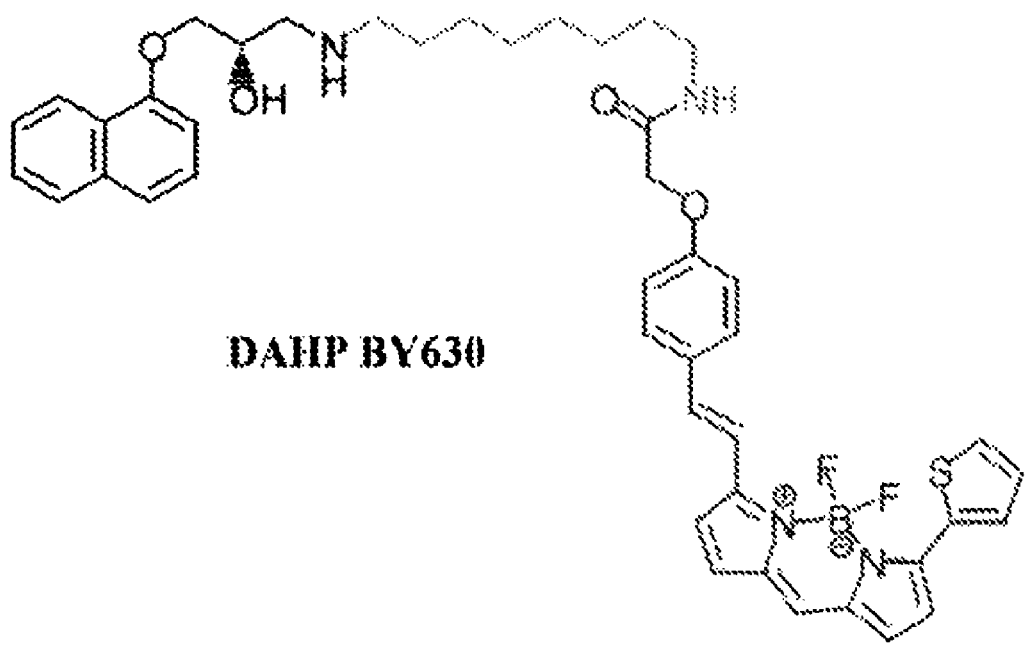
DAHP BY630
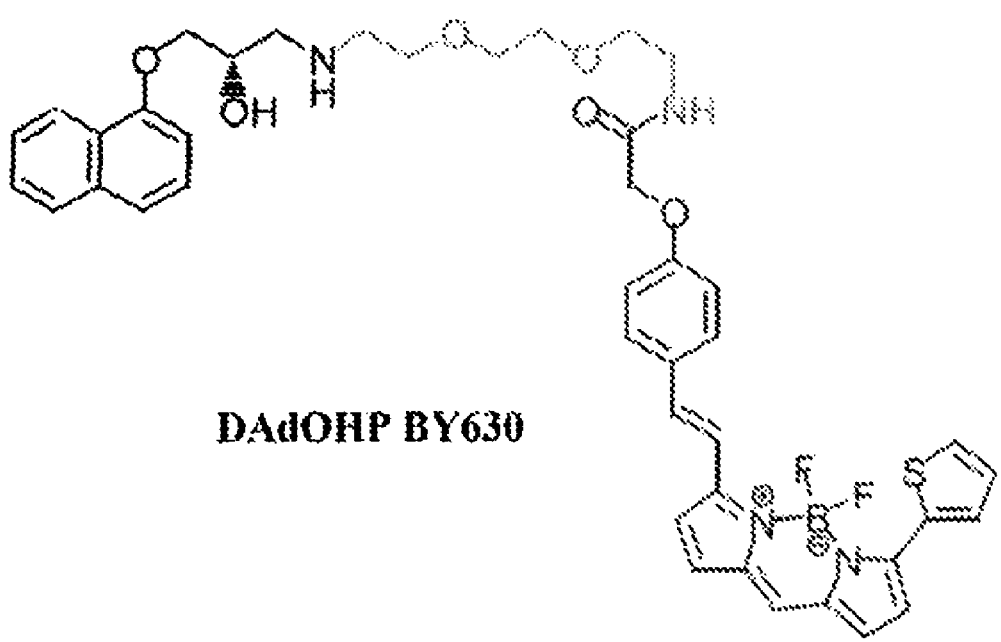
DAdOHP BY630

FIG. 1.15
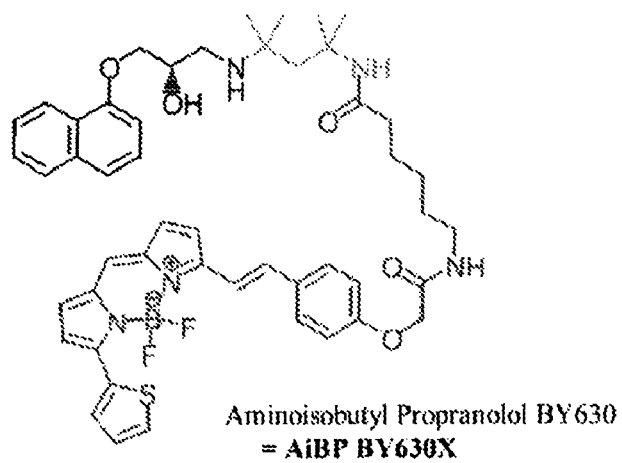
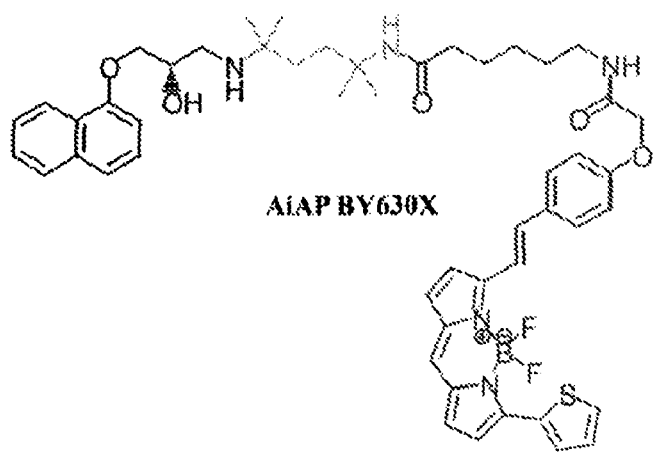
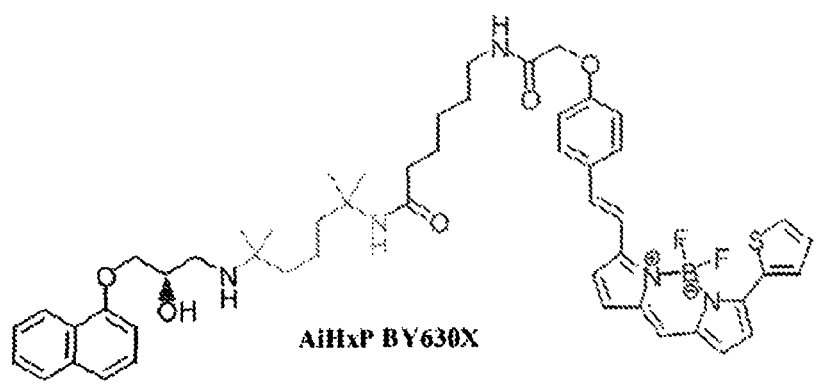

FIG. 1.16
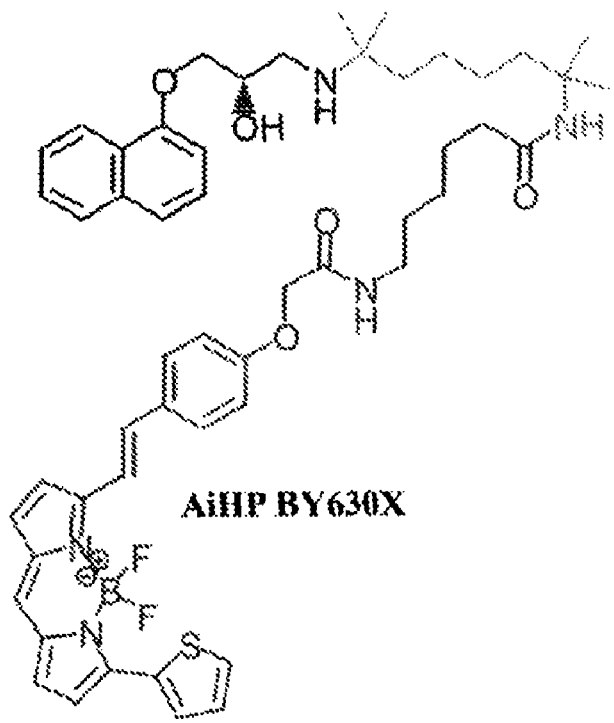
AiHP BY630X
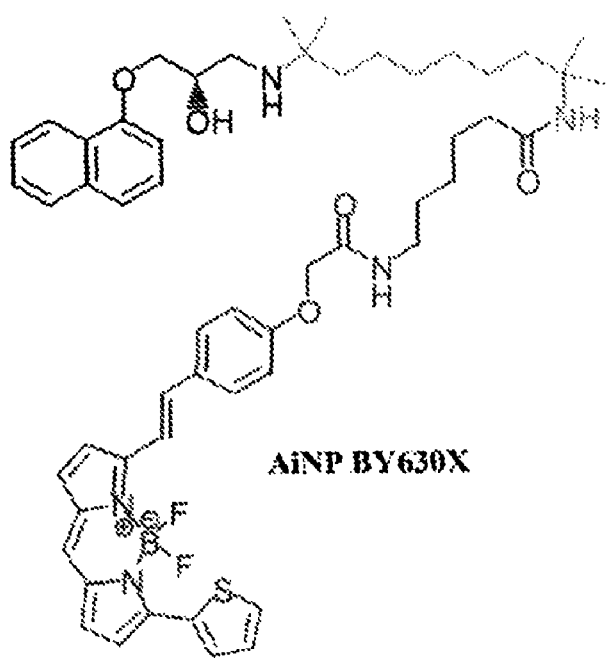
AiNP BY630X

FIG. 1.17
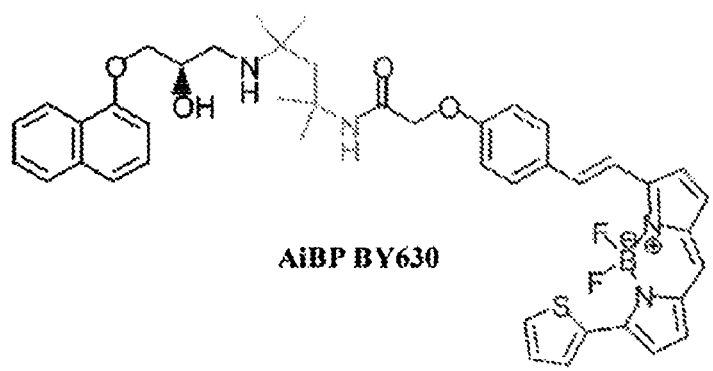
AiBP BY630
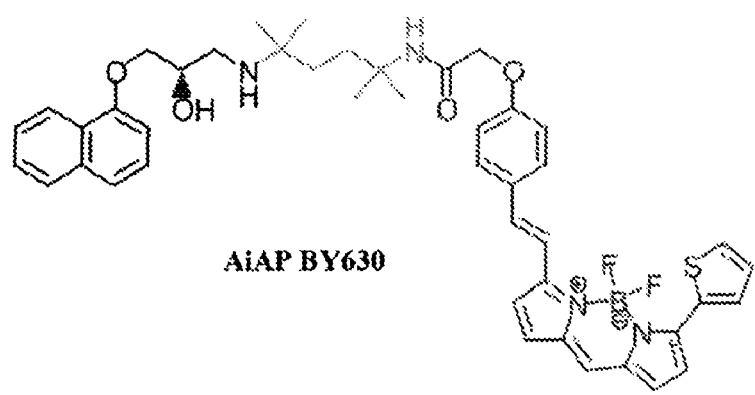
AiAP BY630
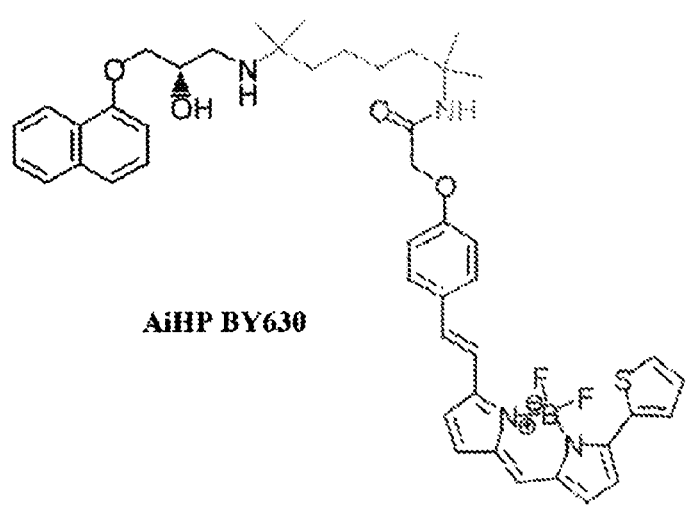
AiHP BY630

FIG. 1.18
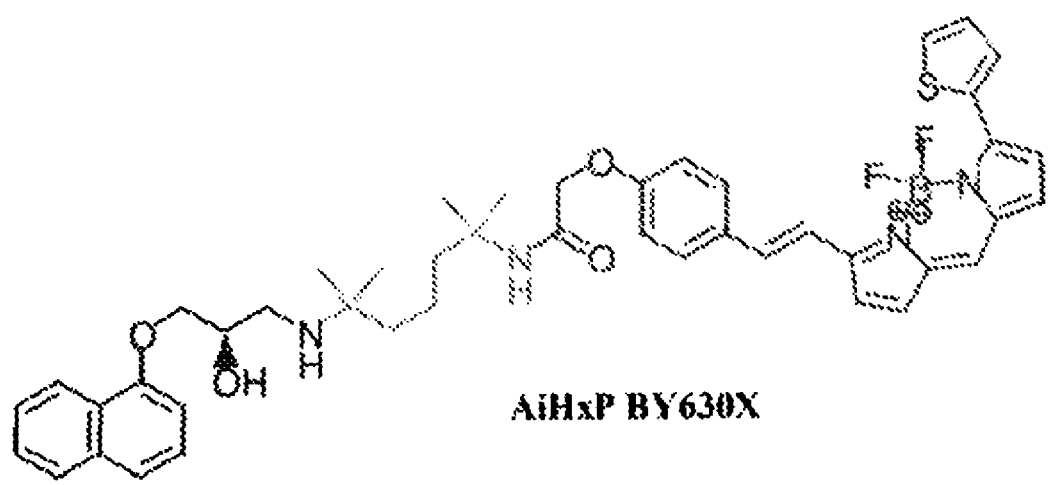
AiHxP BY630X
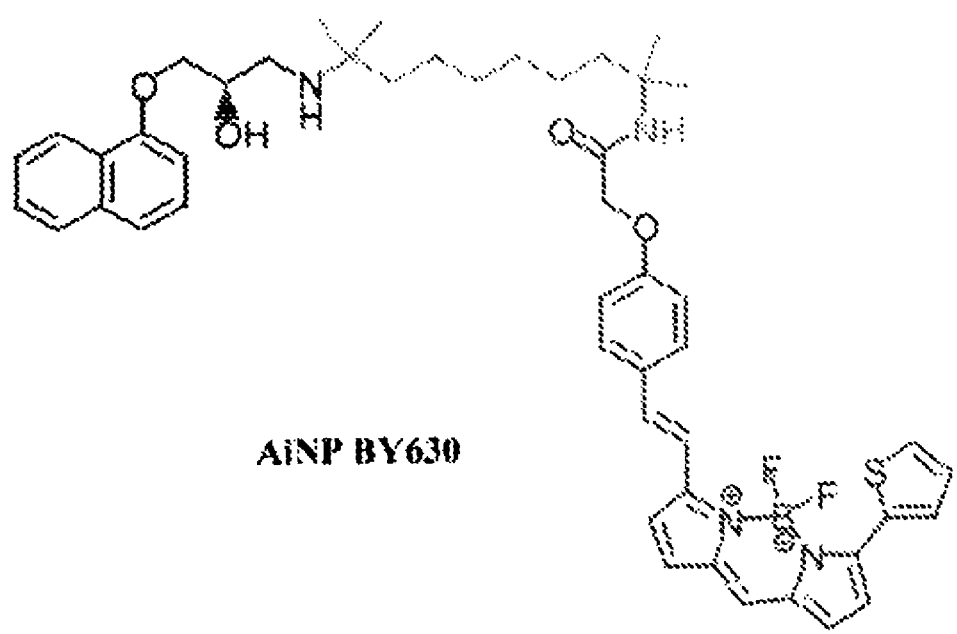
AiNP BY630

FIG. 1.19
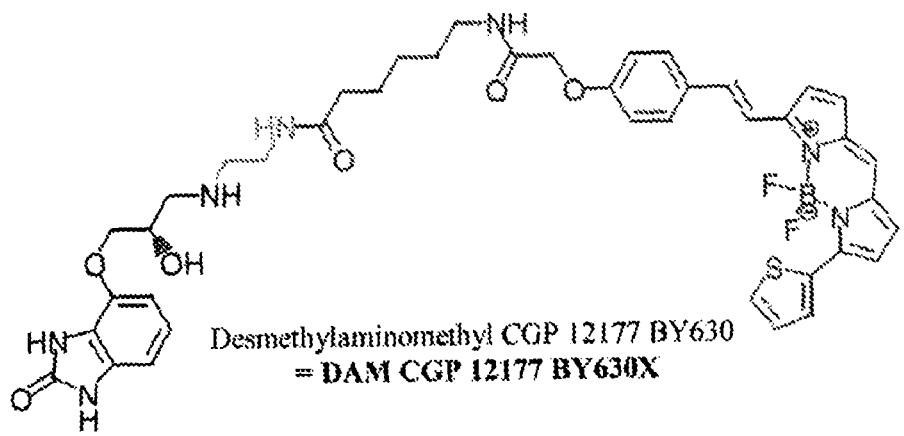
Desmethylaminomethyl CGP 12177 BY630
= DAM CGP 12177 BY630X
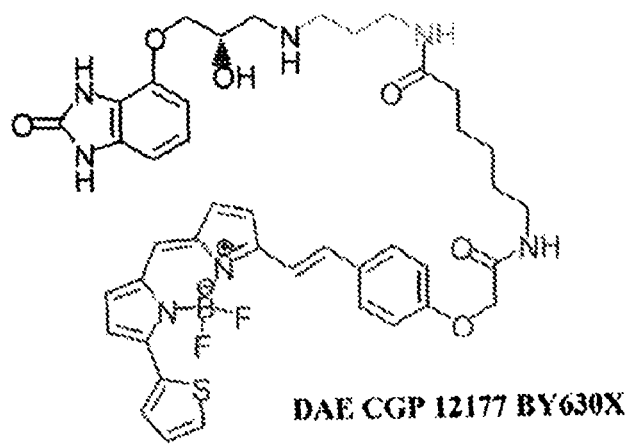
DAE CGP 12177 BY630X
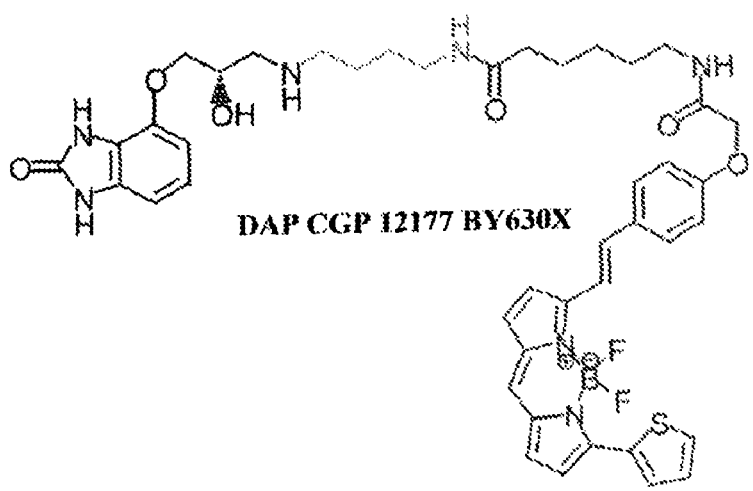
DAP CGP 12177 BY630X FIG. 1.20
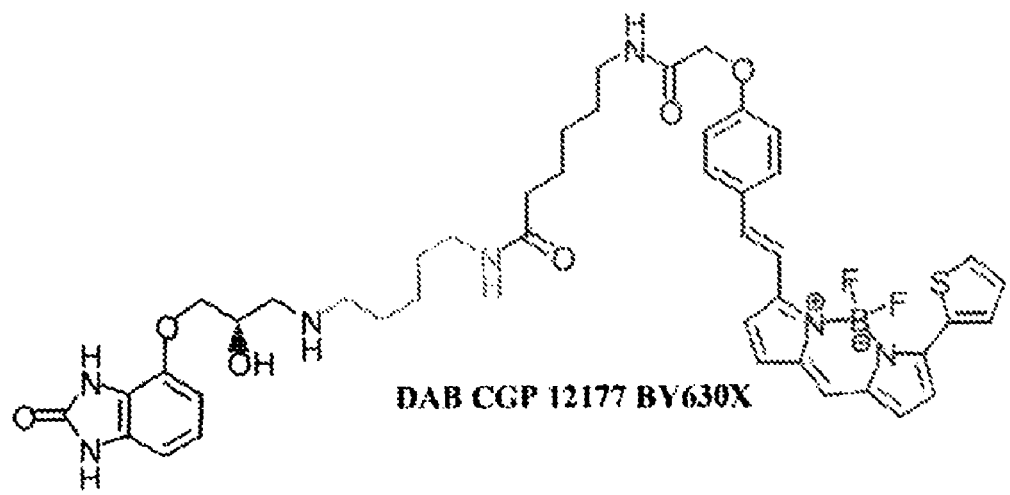
DAB CGP 12177 BY630X
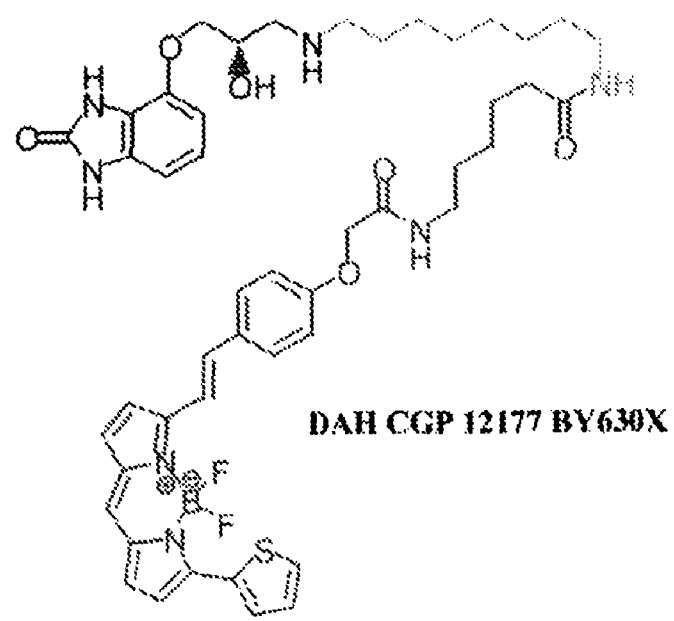
DAH CGP 12177 BY630X FIG. 1.21
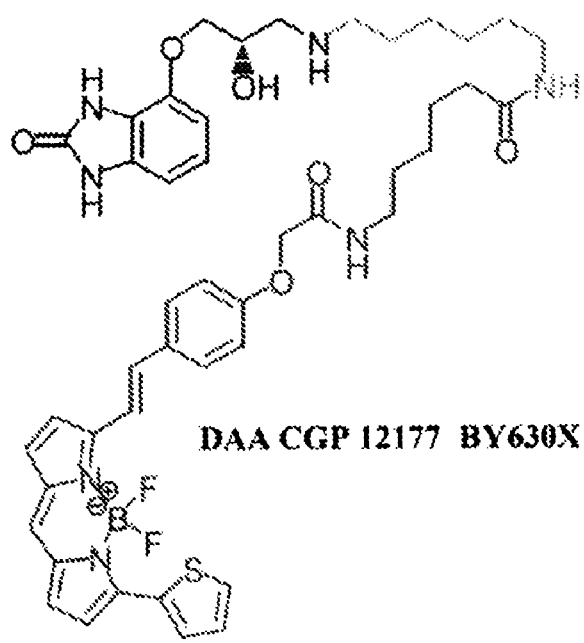
DAA CGP 12177 BY630X
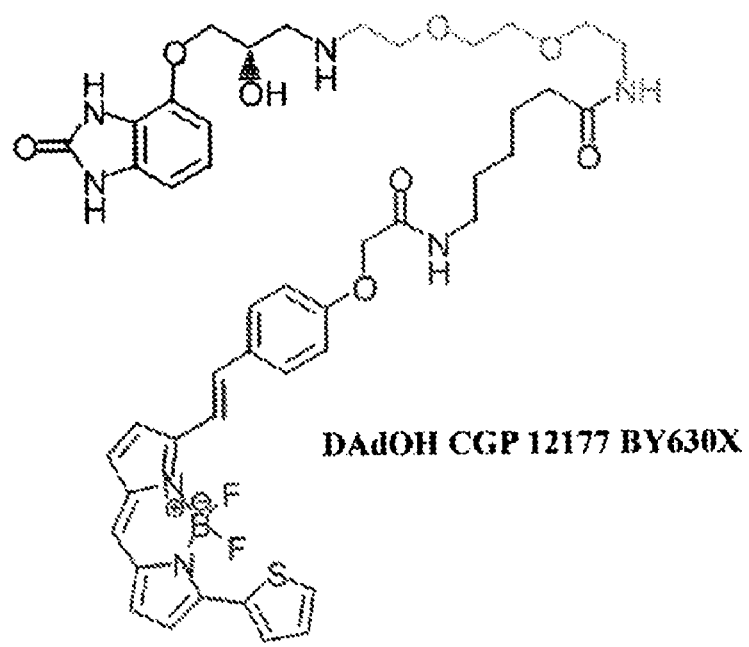
DAdOH CGP 12177 BY630X FIG. 1.22
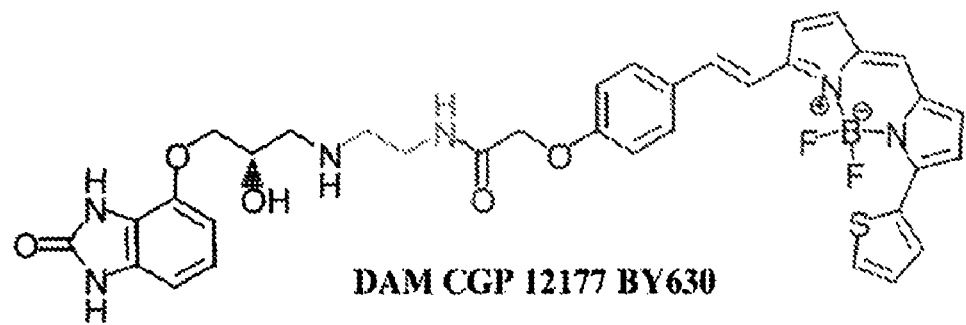
DAM CGP 12177 BY630
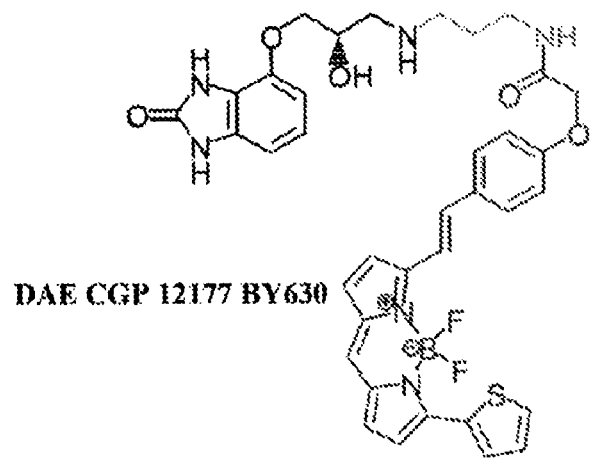
DAE CGP 12177 BY630
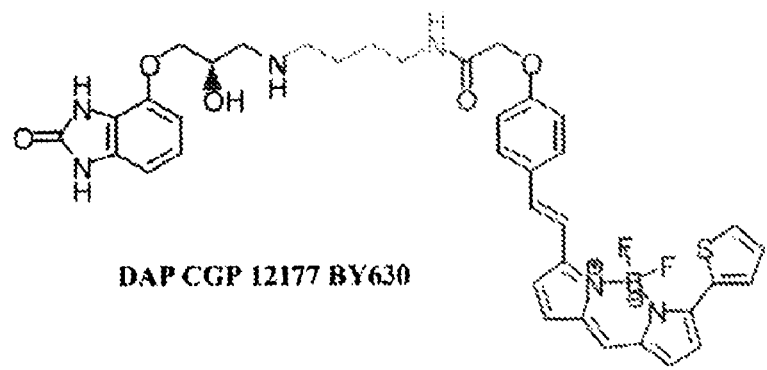
DAP CGP 12177 BY630

FIG. 1.23
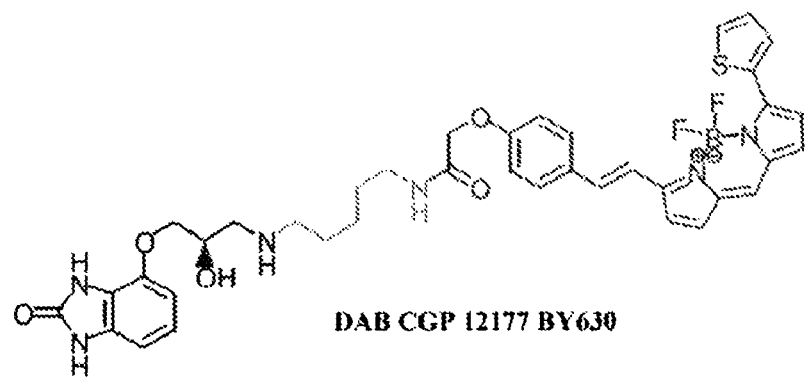
DAB CGP 12177 BY630
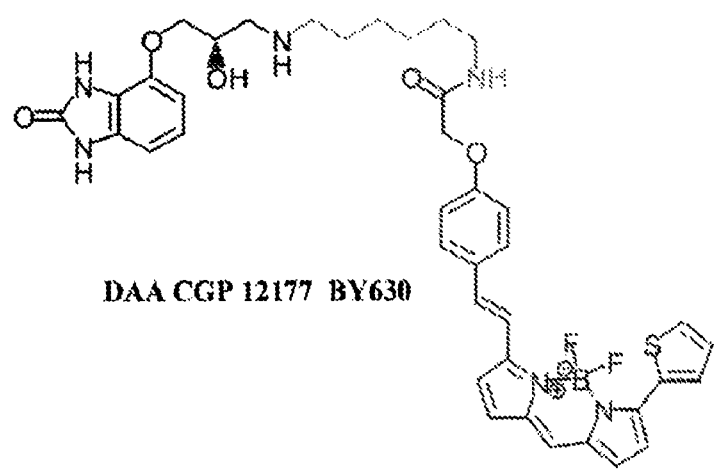
DAA CGP 12177 BY630
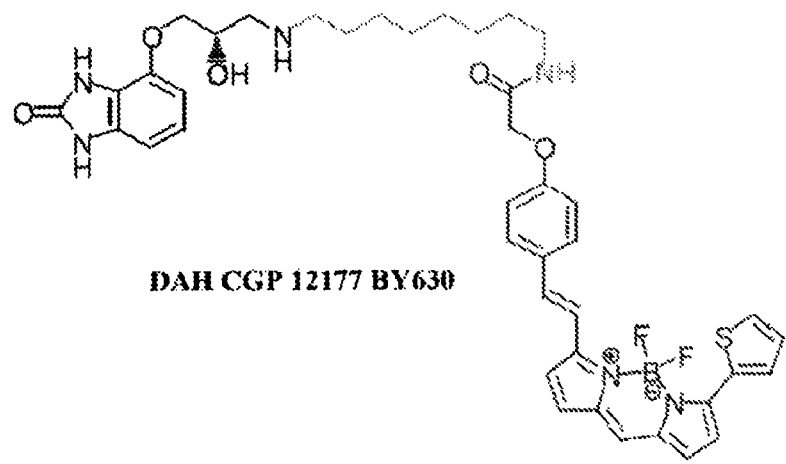
DAH CGP 12177 BY630

FIG. 1.24
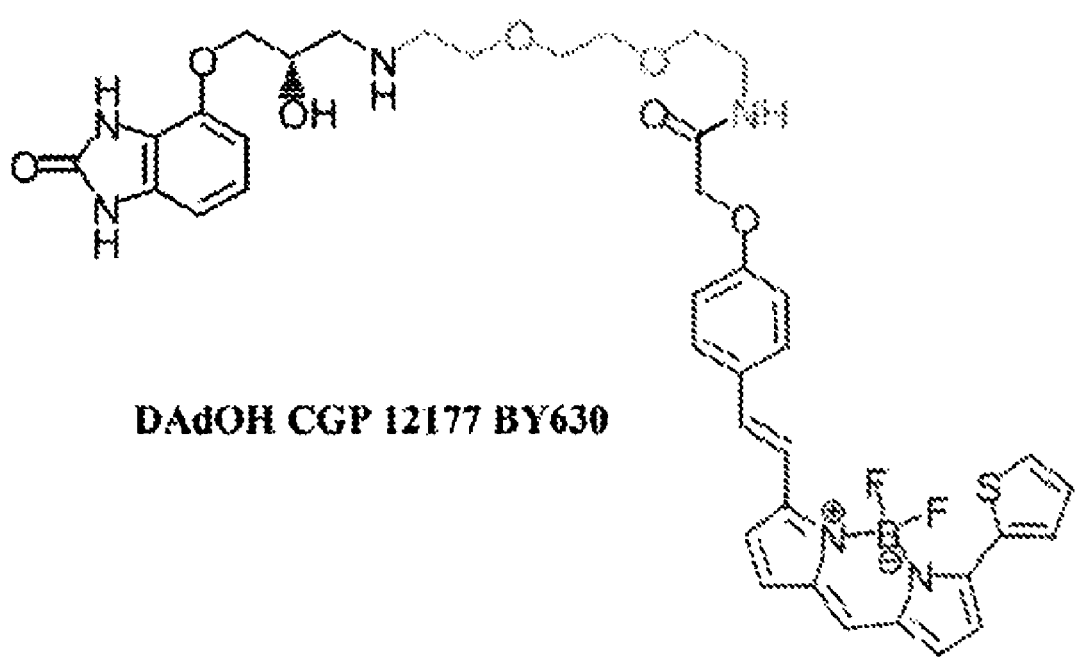
DAdOH CGP 12177 BY630

FIG. 1.25
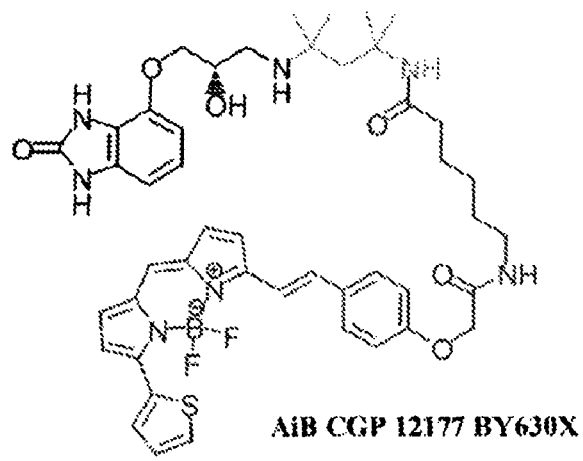
AiB CGP 12177 BY630X
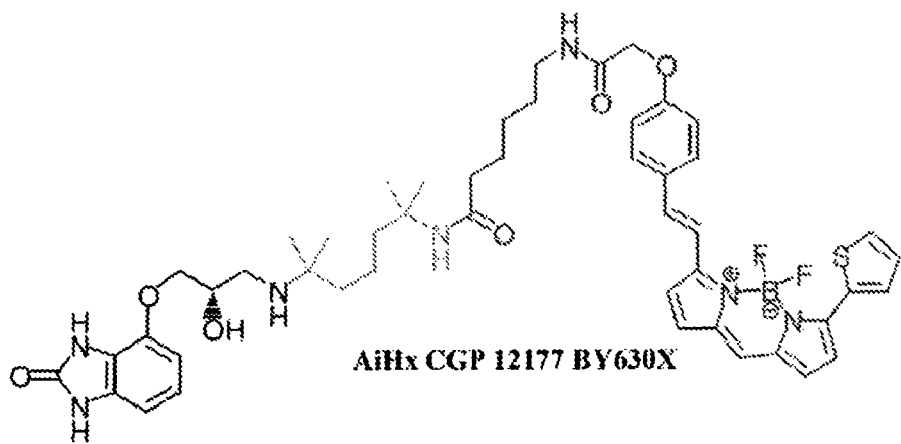
AiHx CGP 12177 BY630X
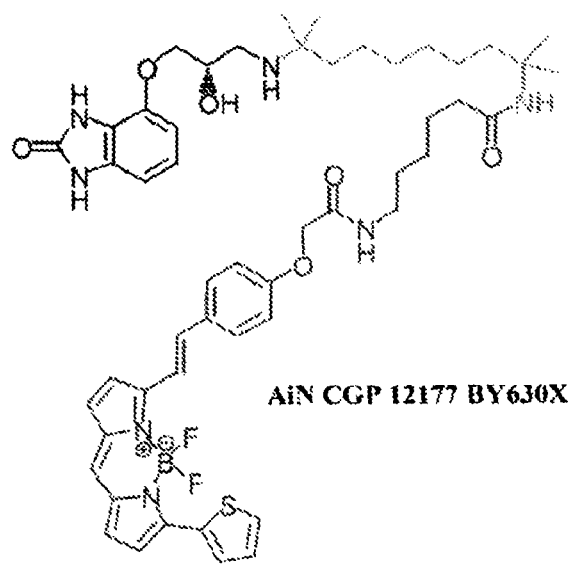
AiN CGP 12177 BY630X

FIG. 1.26
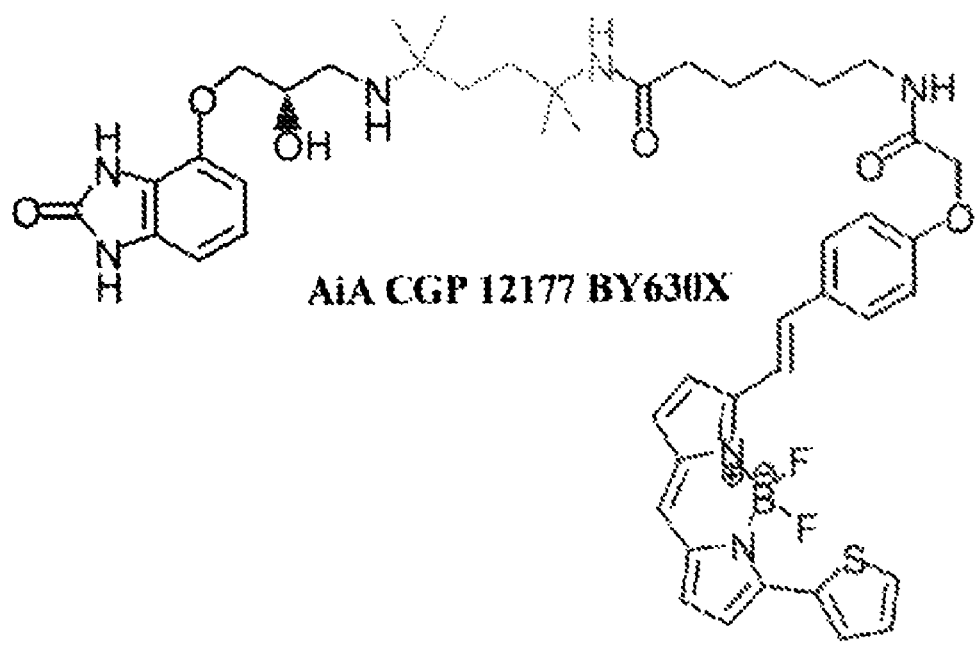
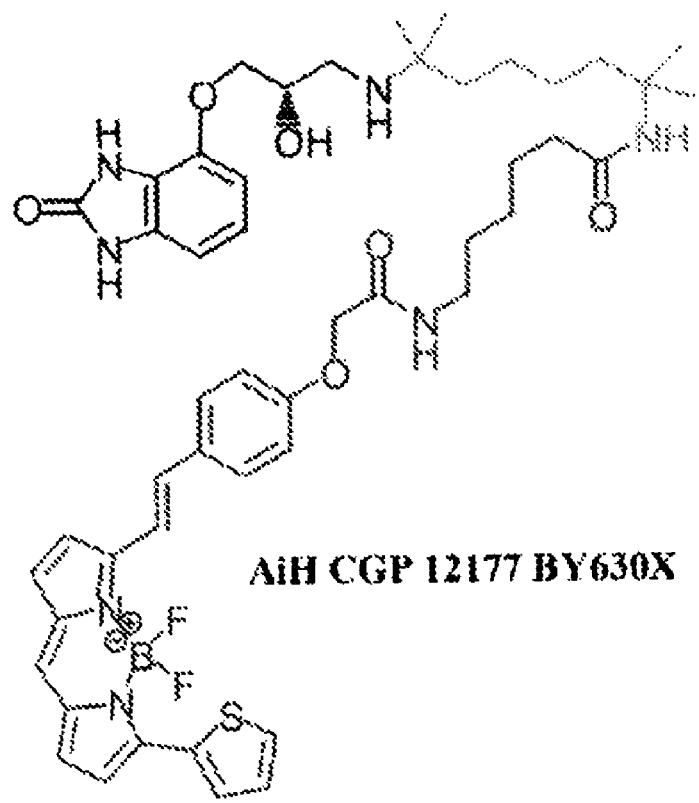

FIG. 1.27
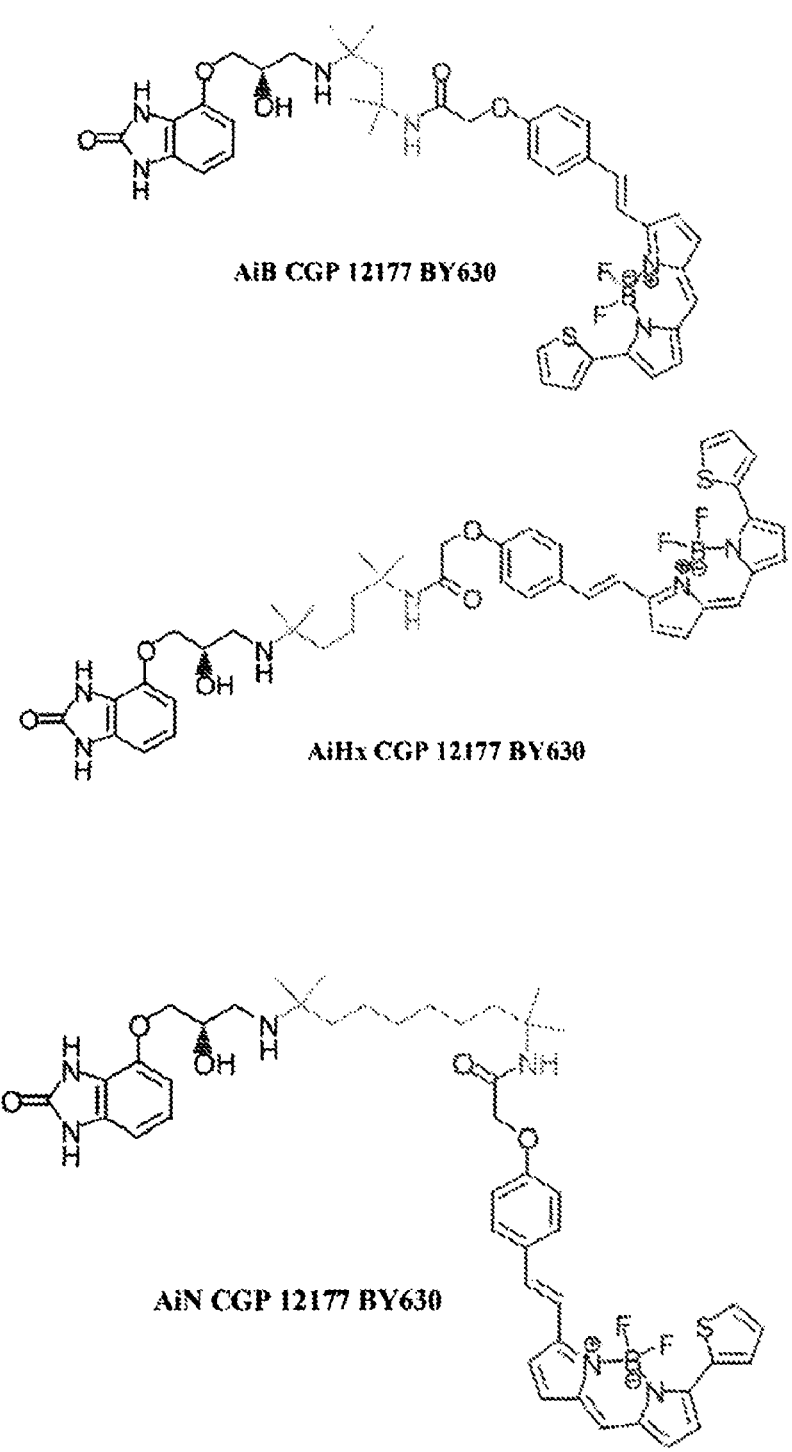

FIG. 1.28
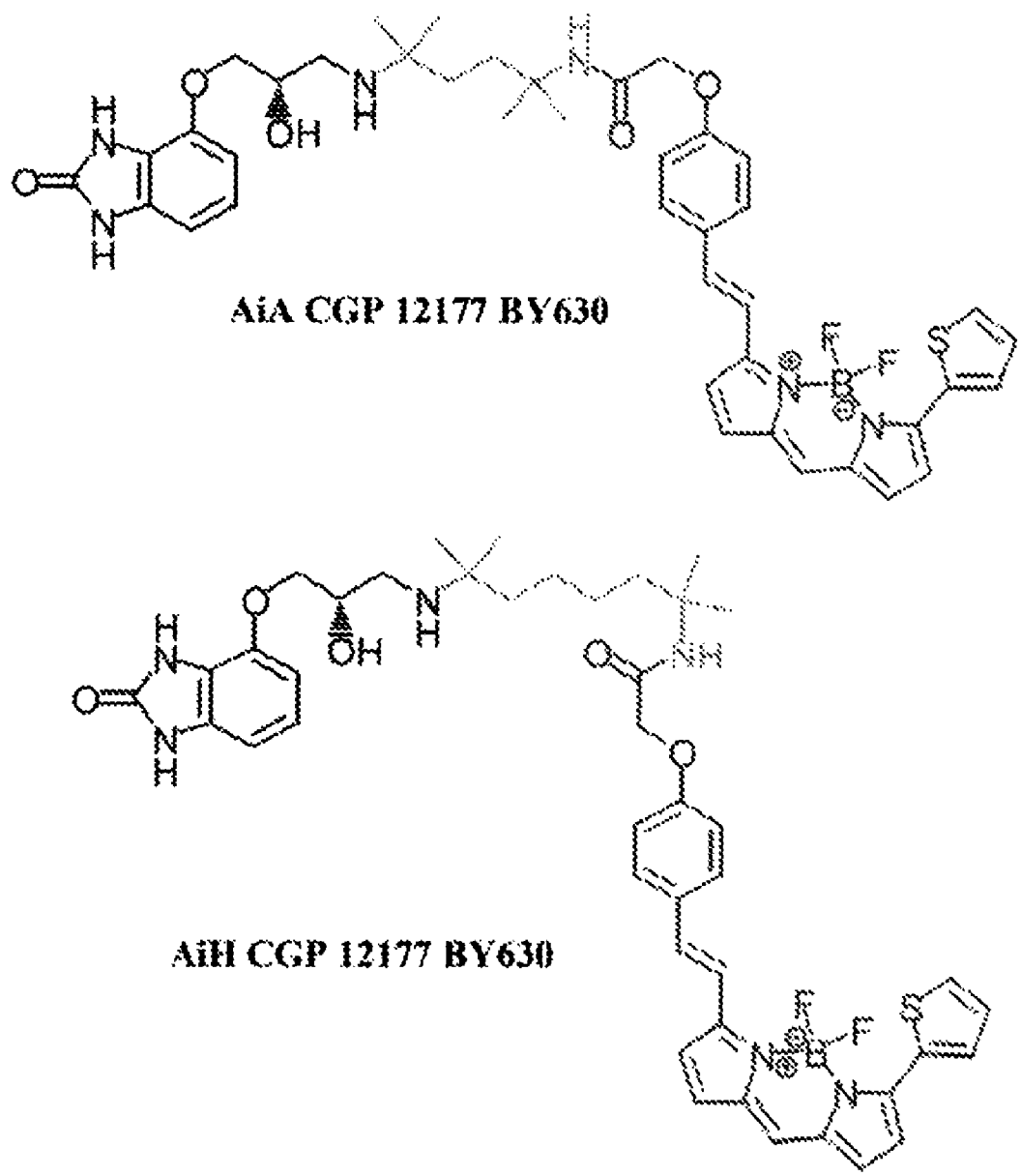

FIG. 1.29
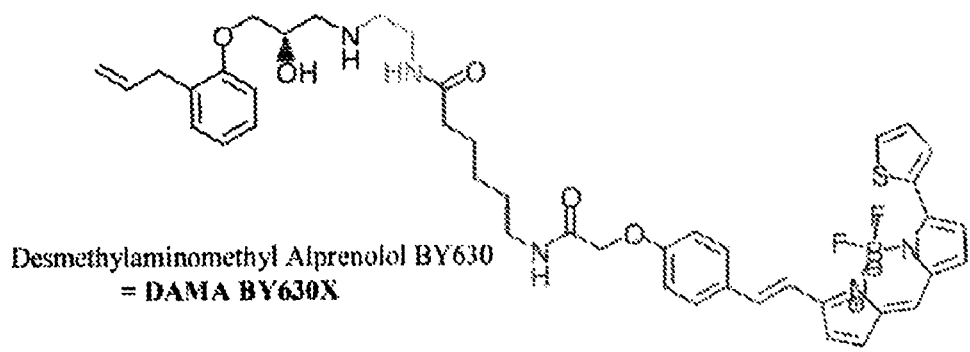
Desmethylaminomethyl Alprenolol BY630
= DAMA BY630X
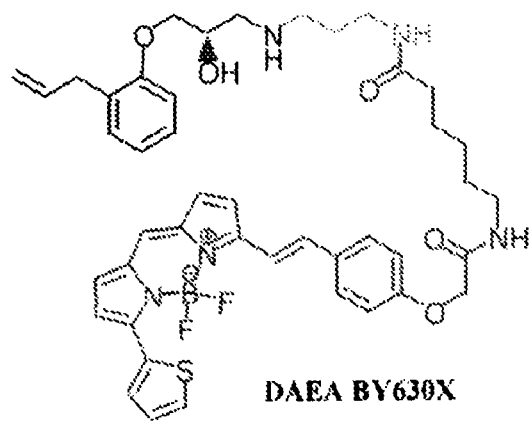
DAEA BY630X
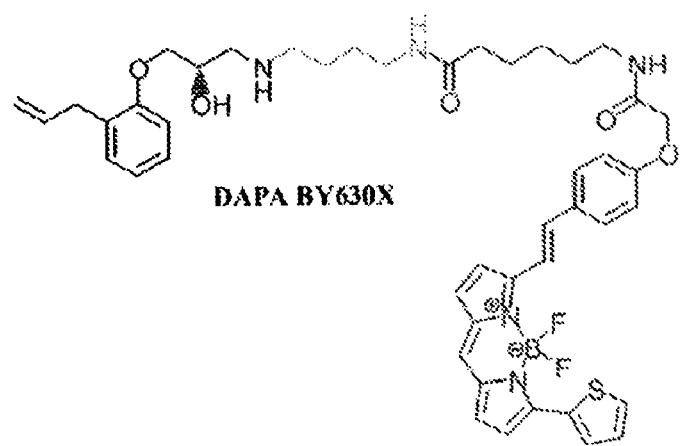
DAPA BY630X FIG. 1.30
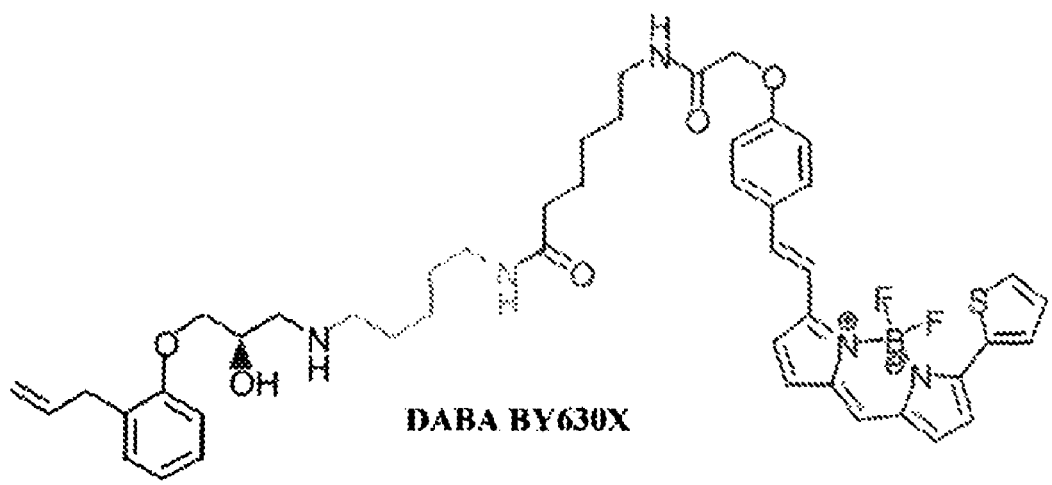
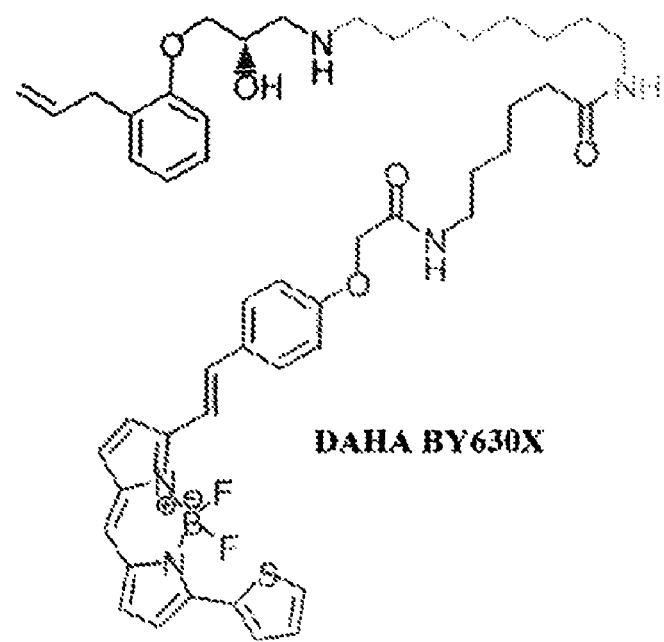

FIG. 1.31
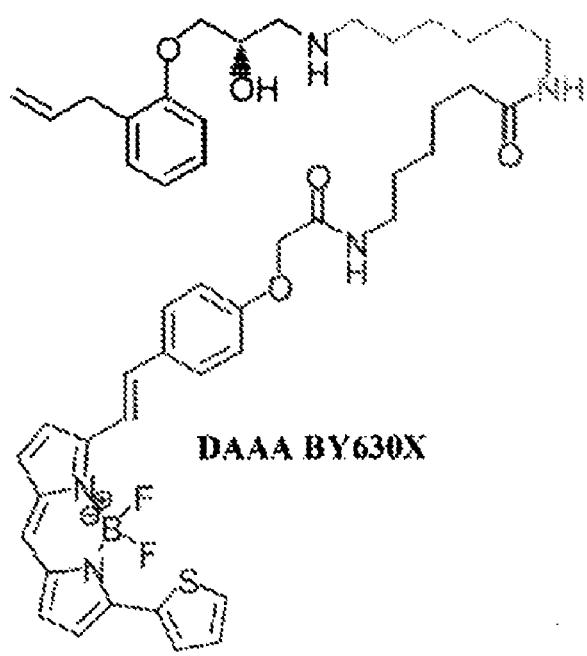
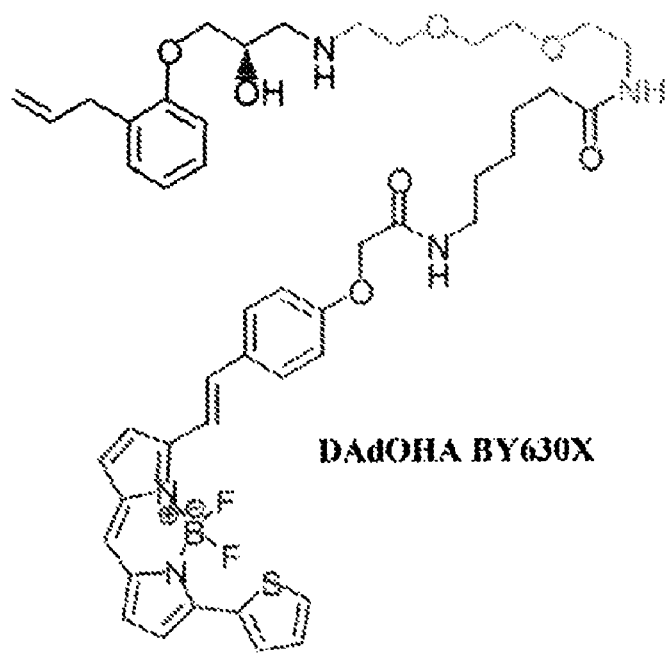

FIG. 1.32
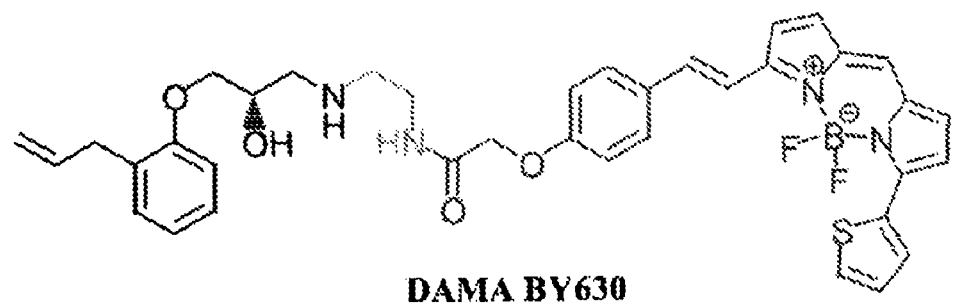
DAMA BY630
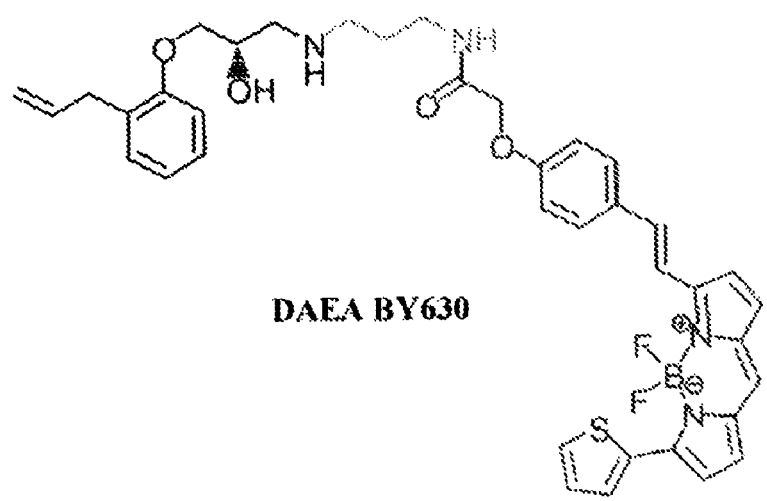
DAEA BY630
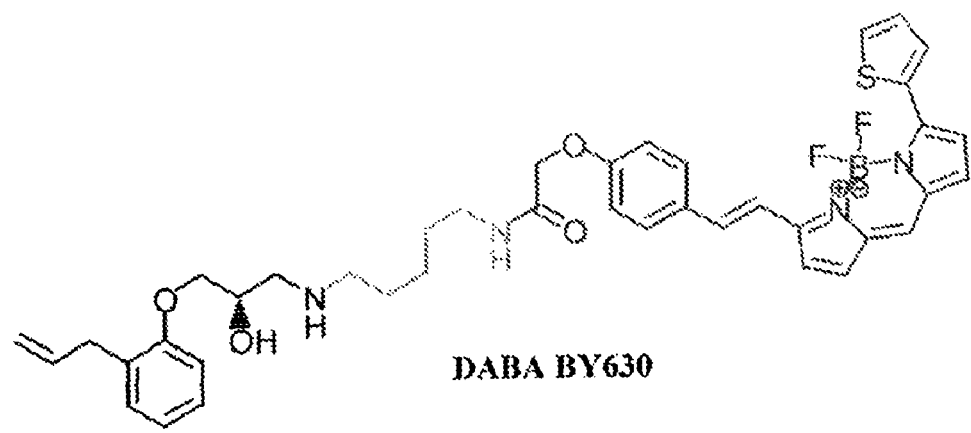
DABA BY630

FIG. 1.33
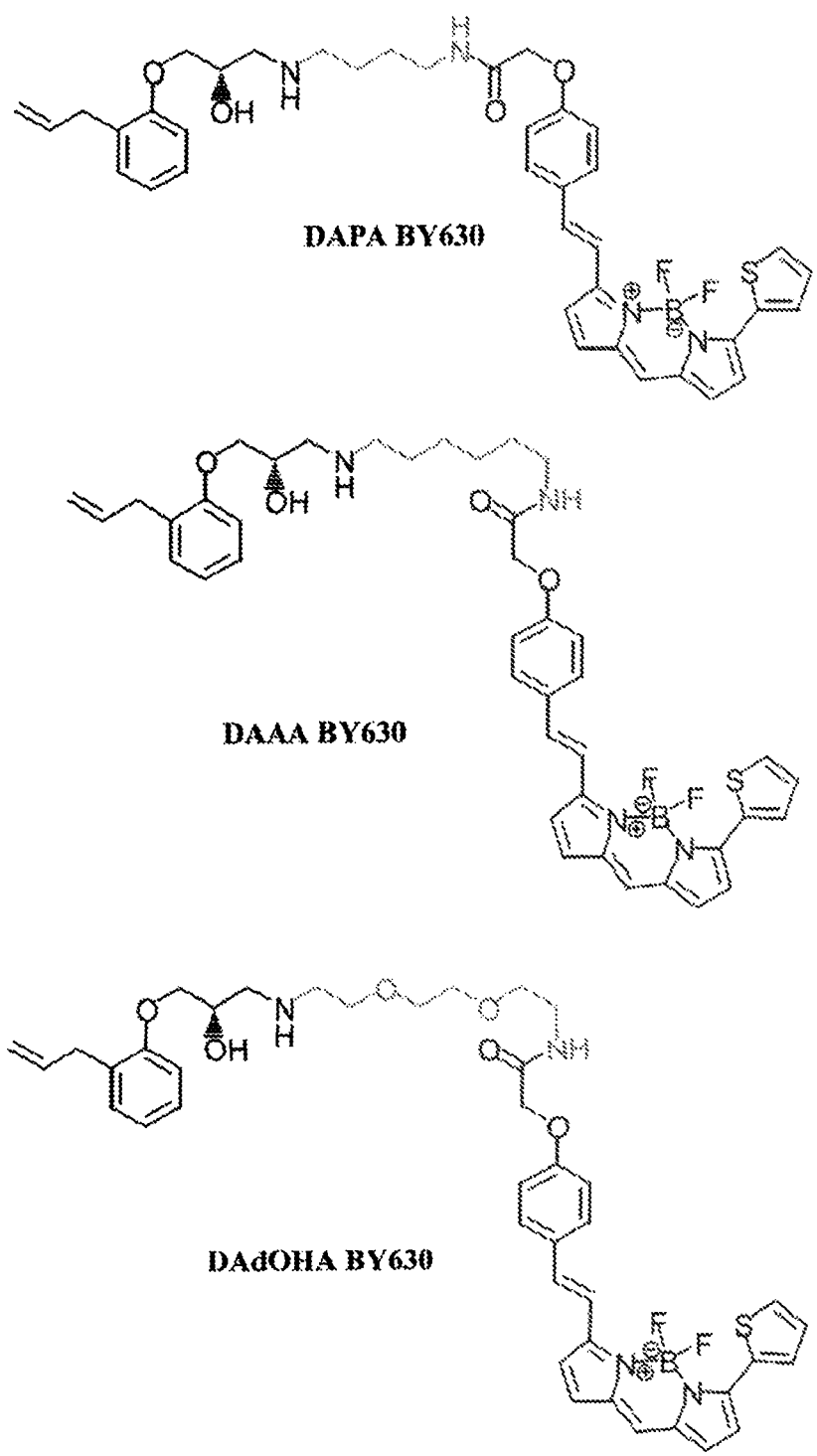

FIG. 1.34
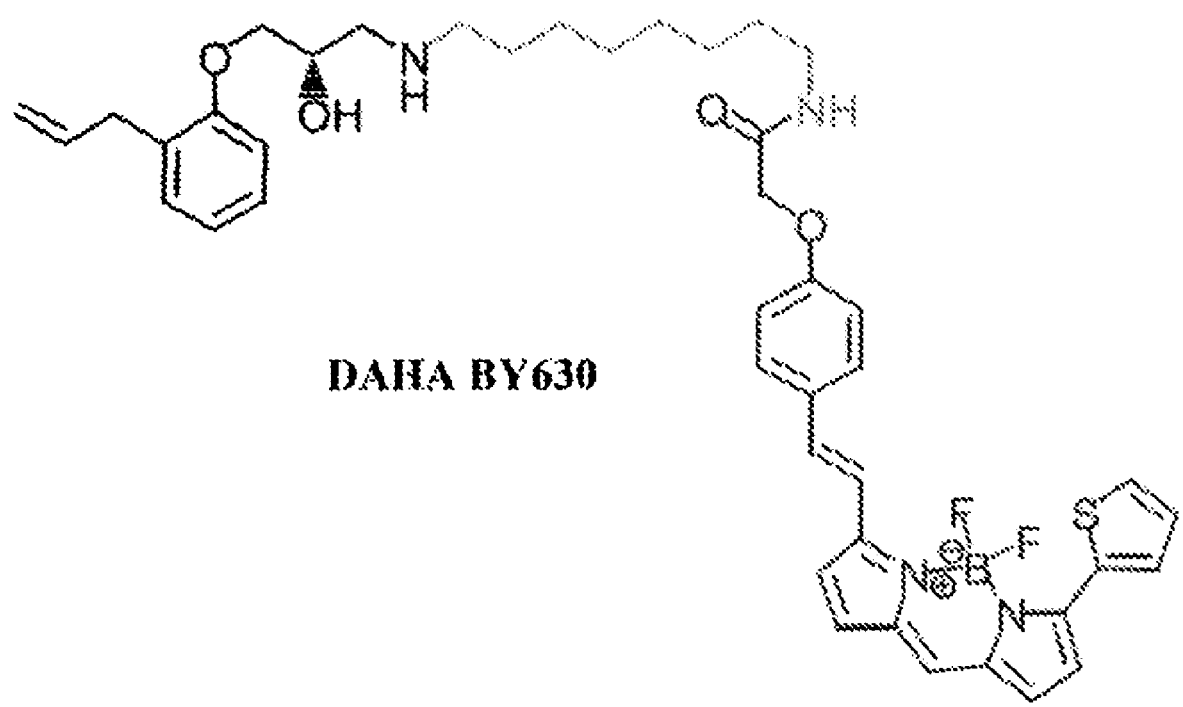
DAHA BY630

FIG. 1.35
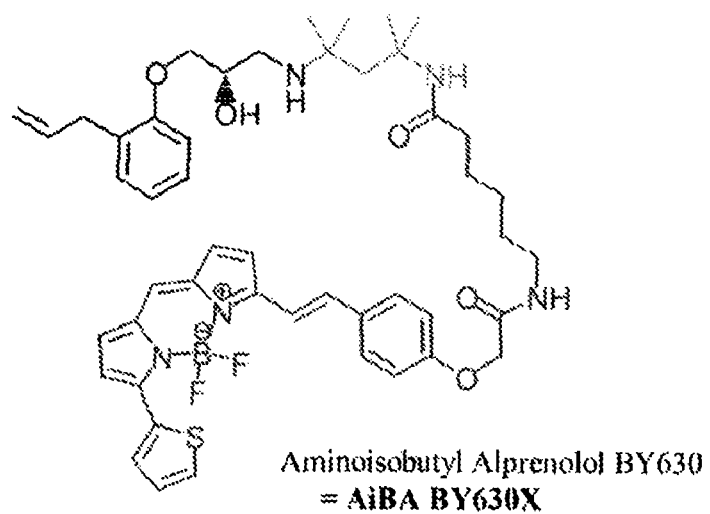
Aminoisobutyl Alprenolol BY630
= AiBA BY630X
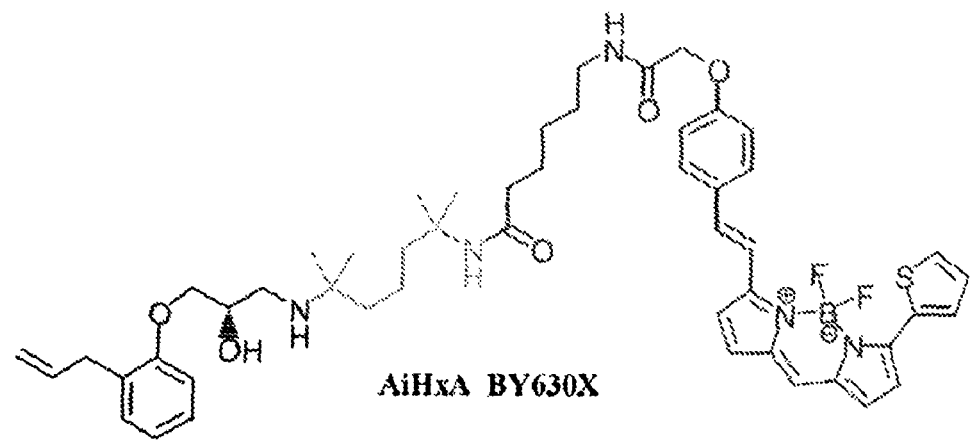
AiHxA BY630X
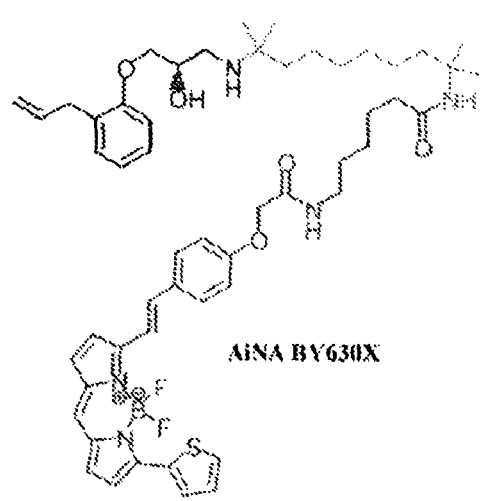
AiNA BY630X FIG. 1.36
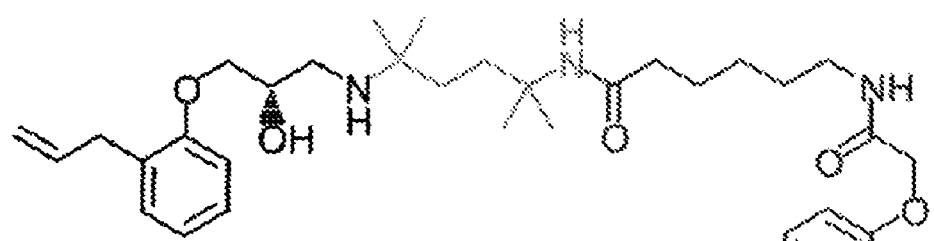
AiAA BY630X
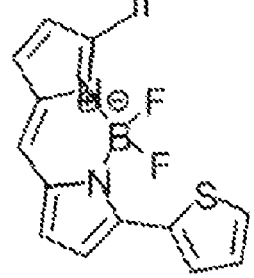
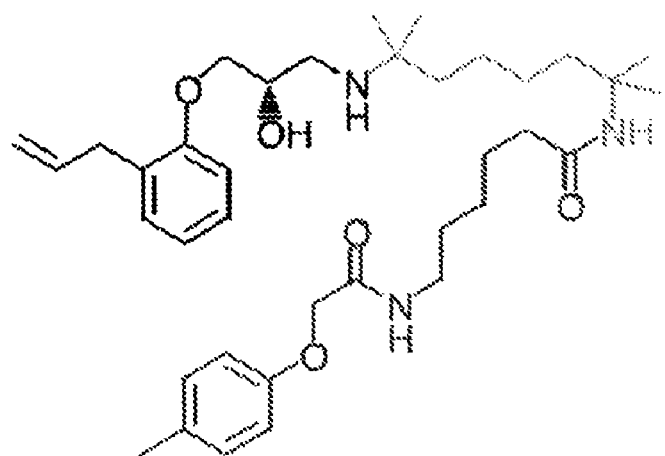
AiHA BY630X
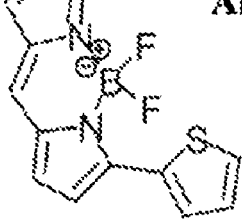

FIG. 1.37
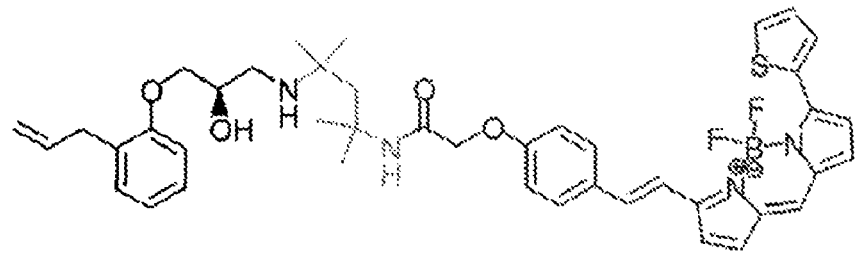
AiBA BY630
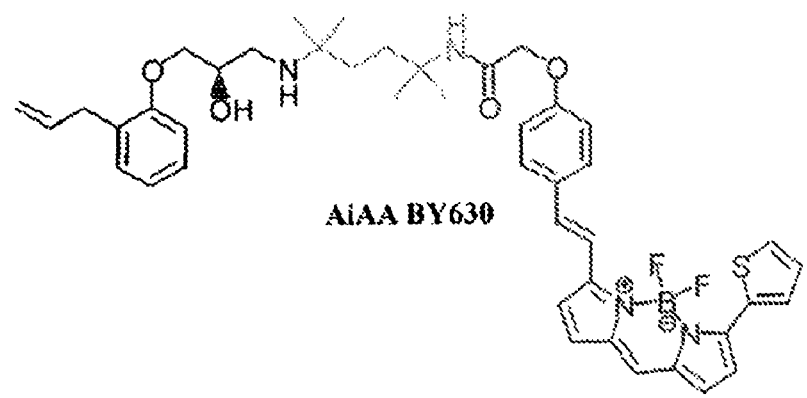
AiAA BY630
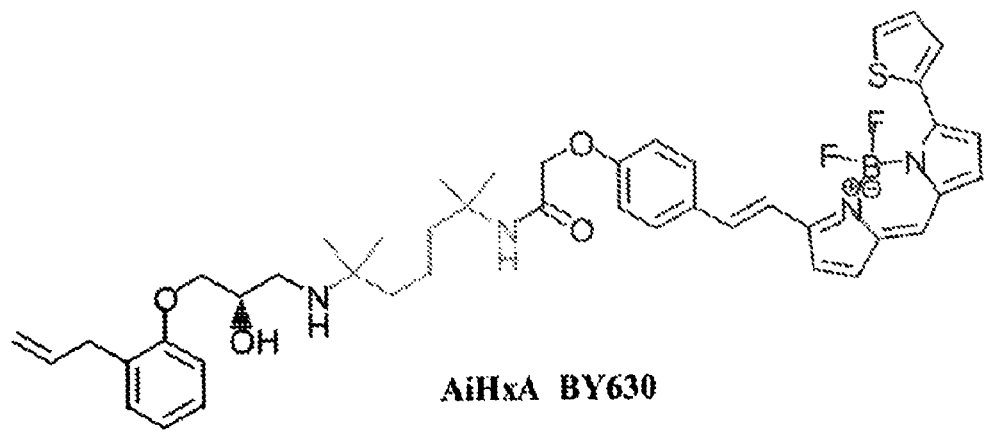
AiHxA BY630

FIG. 1.38
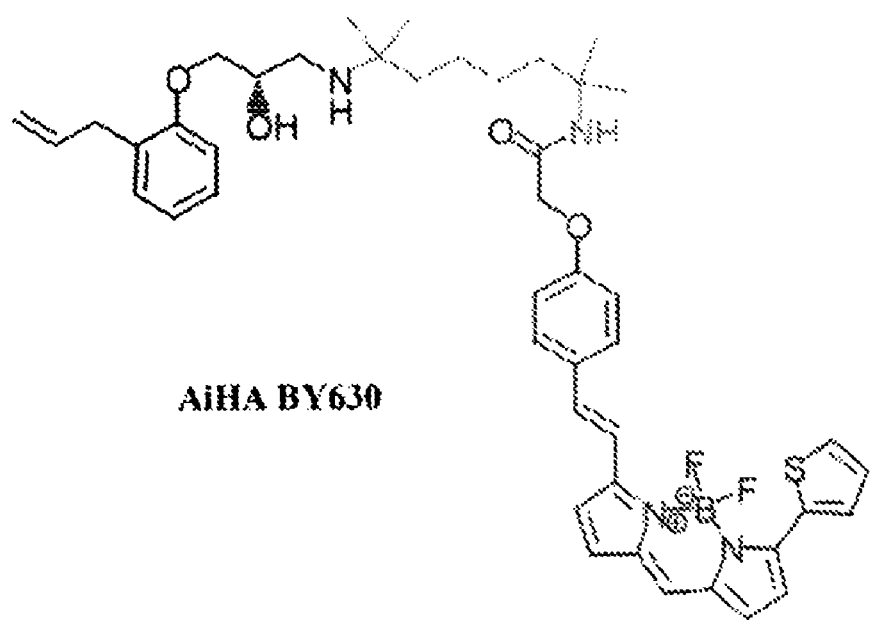
AiHA BY630
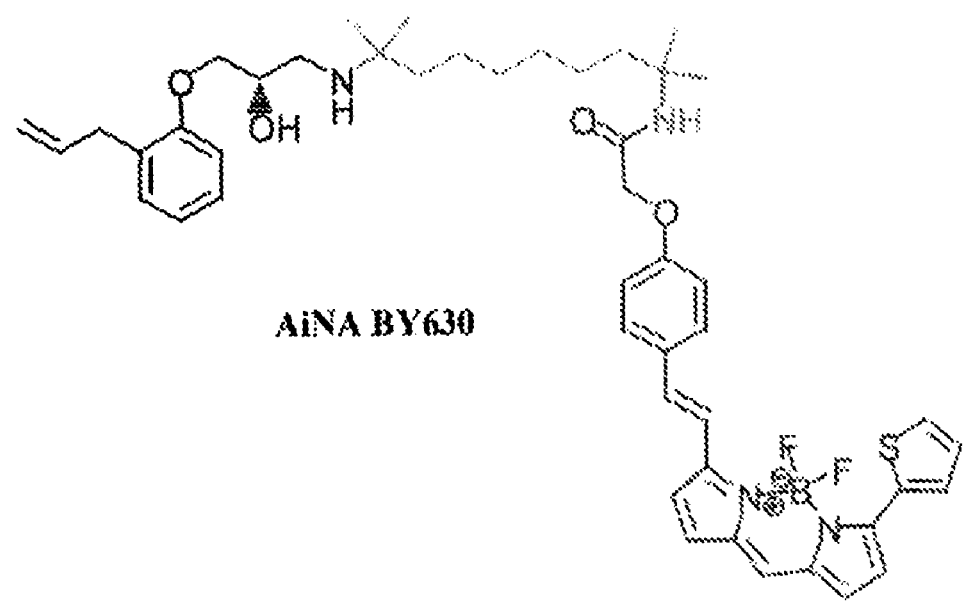
AiNA BY630

FIG. 1.39
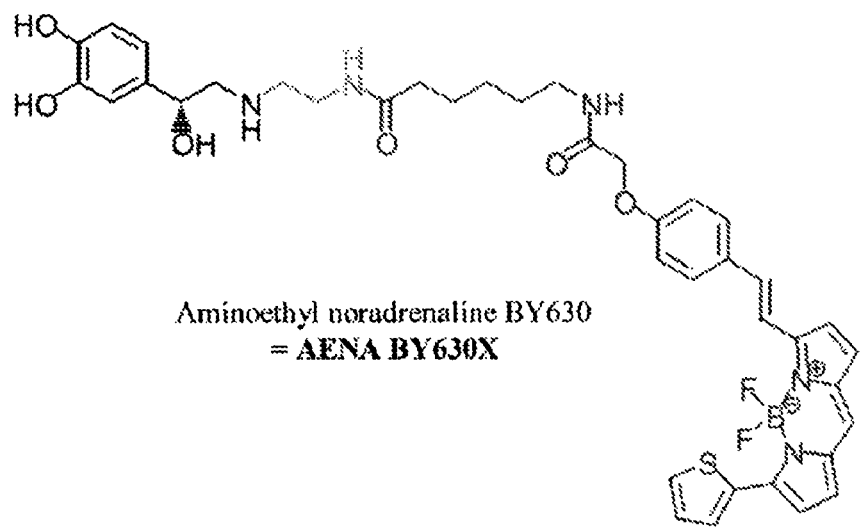
Aminoethyl noradrenaline BY630
= AENA BY630X
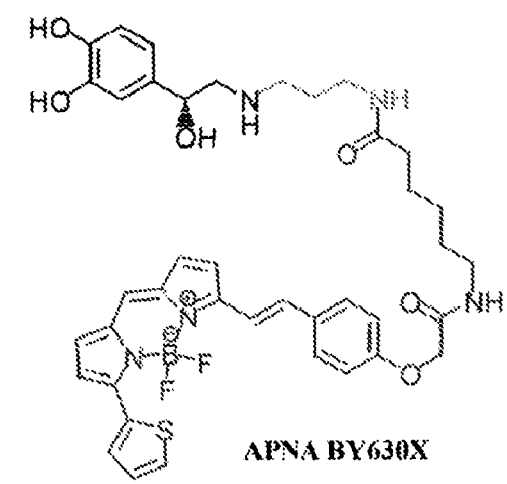
APNA BY630X
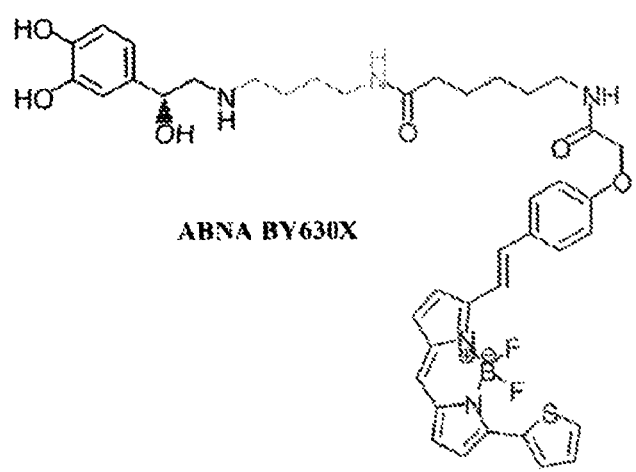
ABNA BY630X FIG. 1.40
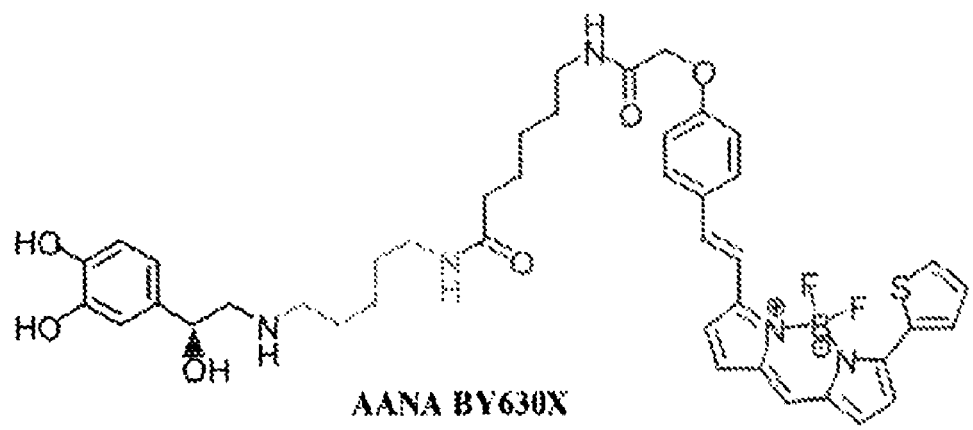
AANA BY630X
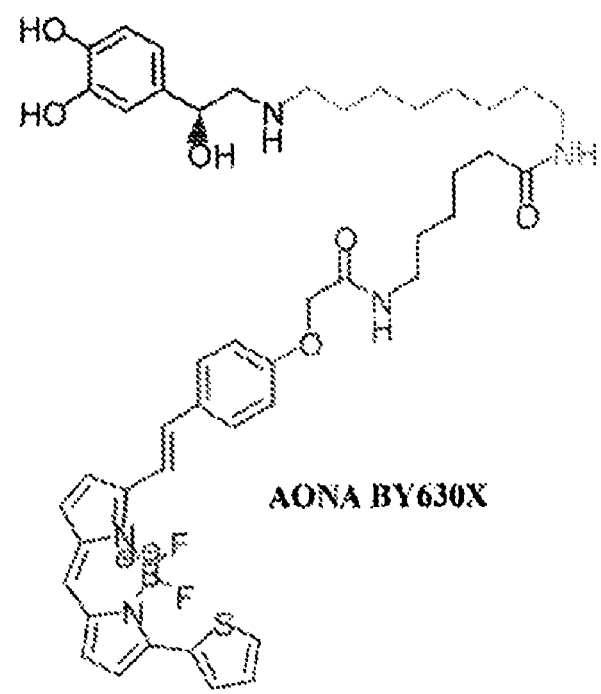
AONA BY630X FIG. 1.41
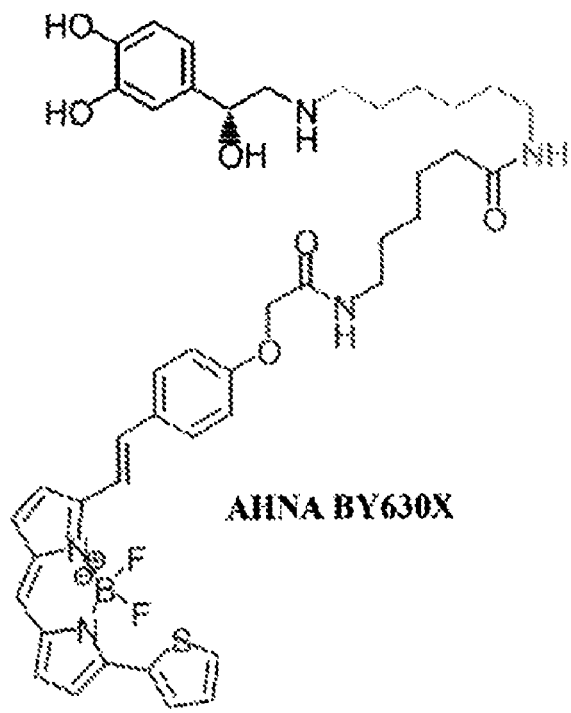
AHNA BY630X
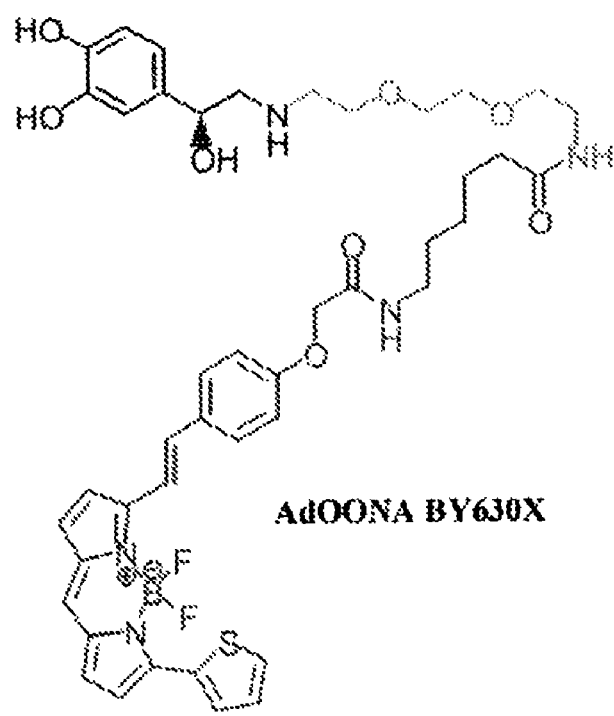
AdOONA BY630X FIG. 1.42
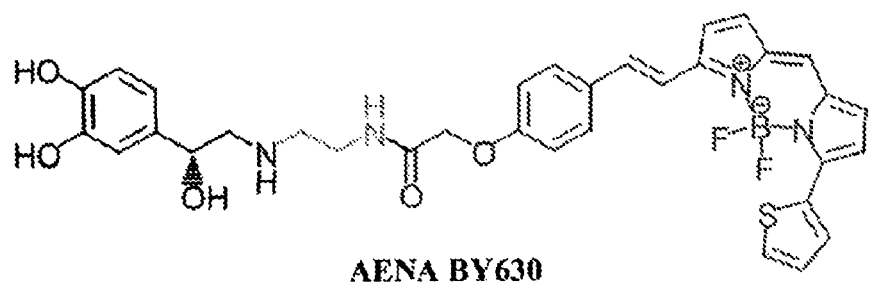
AENA BY630
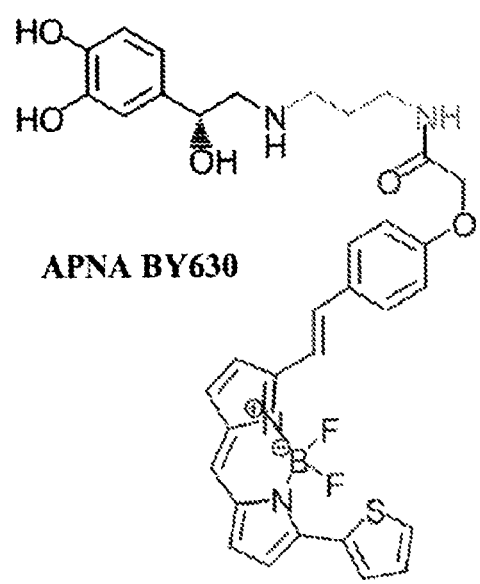
APNA BY630
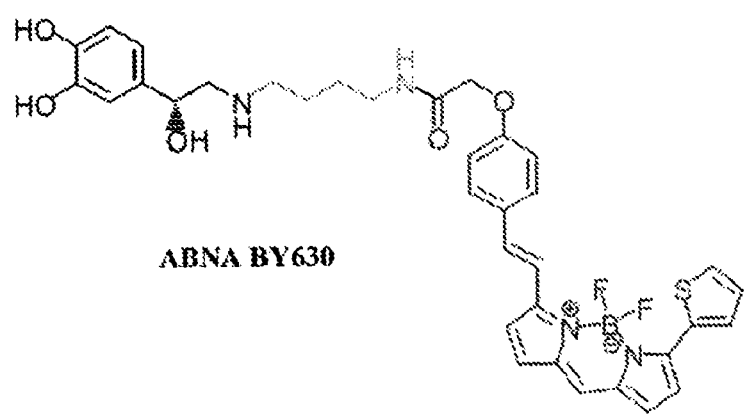
ABNA BY630

FIG. 1.43
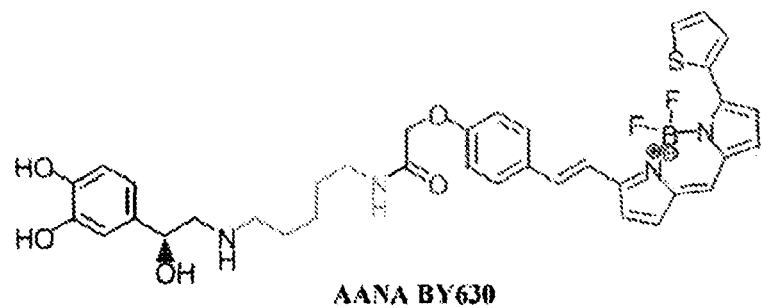
AANA BY630
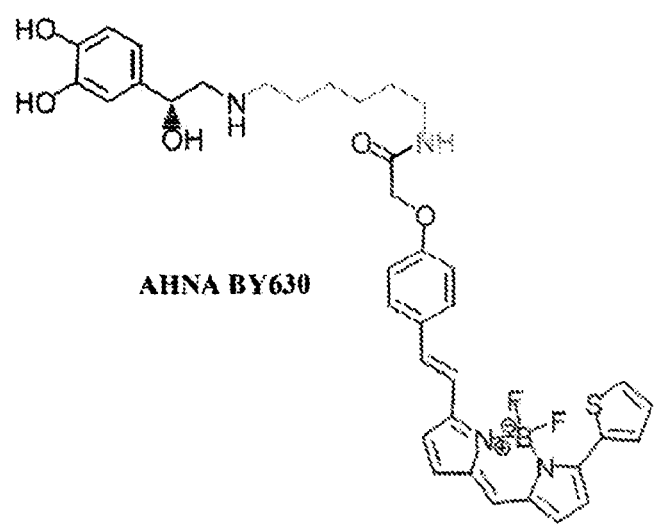
AHNA BY630
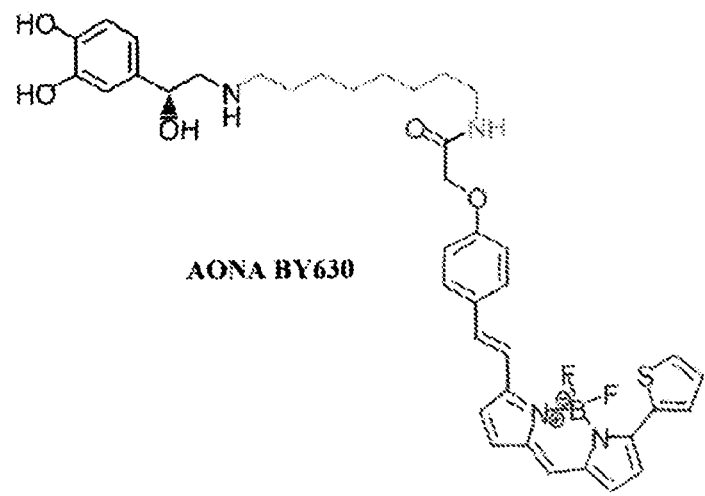
AONA BY630

FIG. 1.44
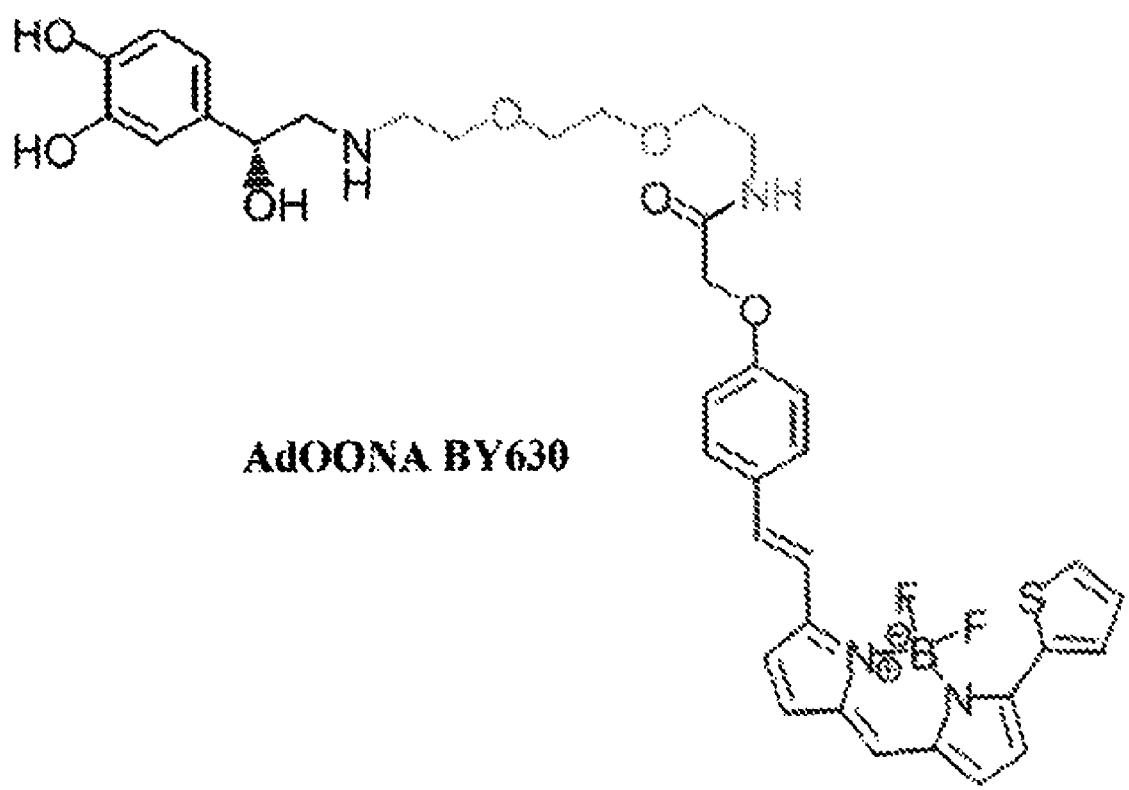
AdOONA BY630

FIG. 1.45
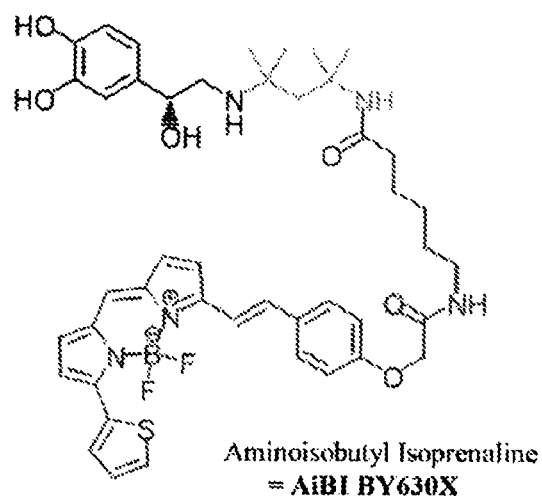
Aminoisobutyl Isoprenaline
= AiBI BY630X
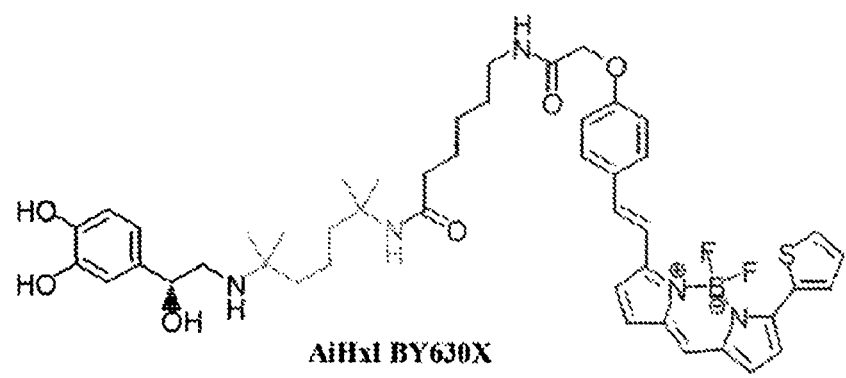
AiHxI BY630X
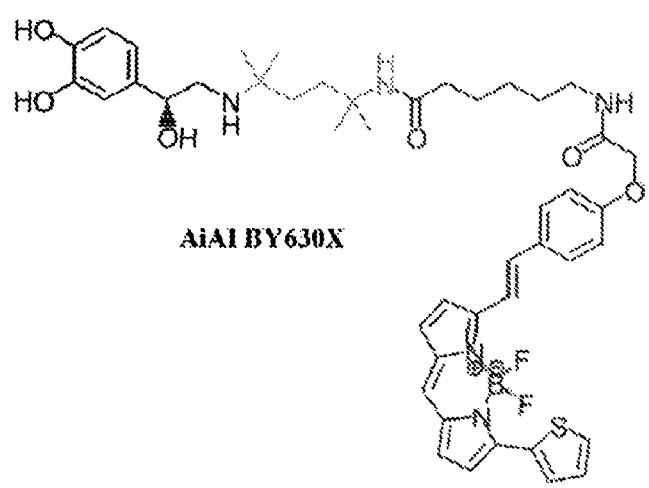
AiAI BY630X FIG. 1.46
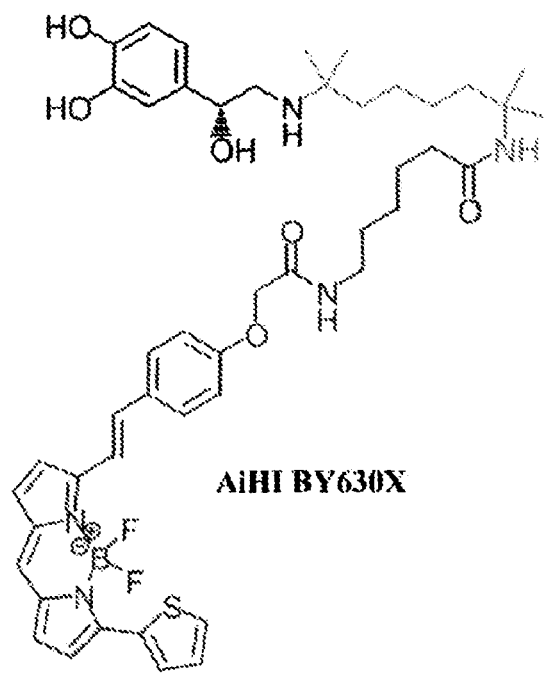
AiHI BY630X
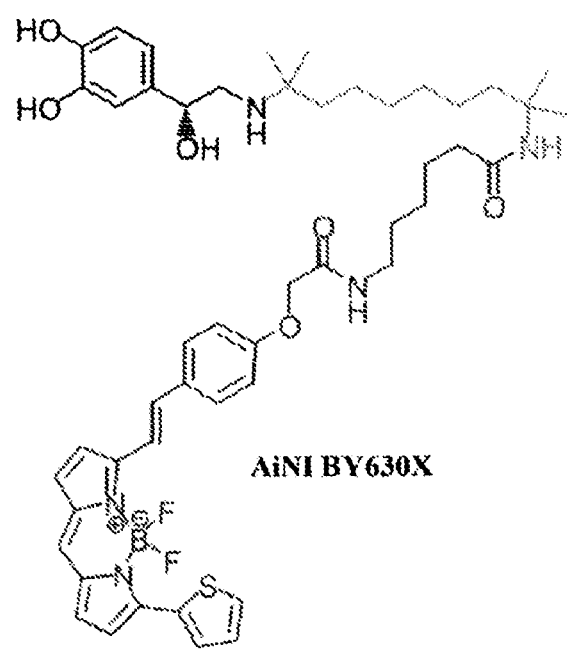
AiNI BY630X FIG. 1.47
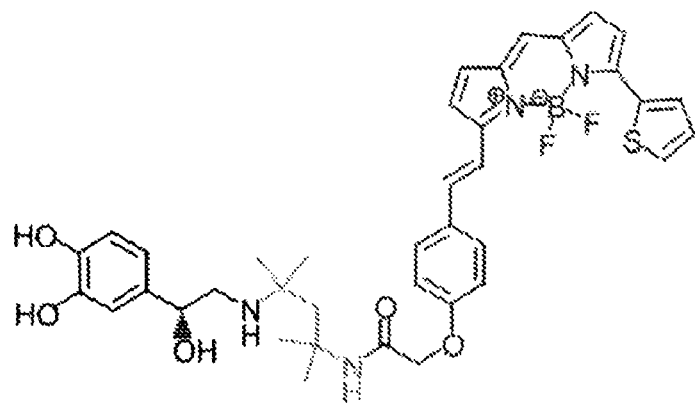
AiBI BY630
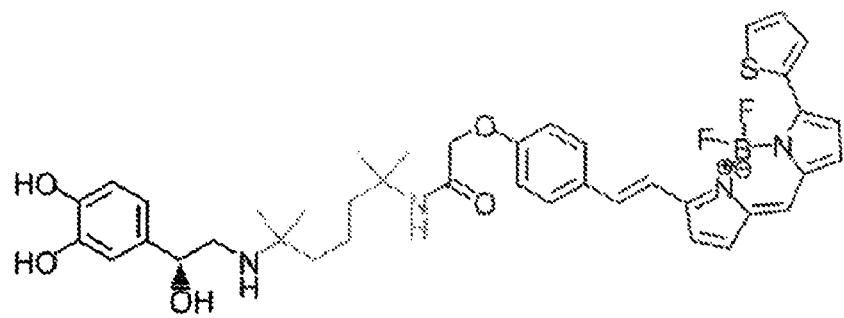
AiHxI BY630
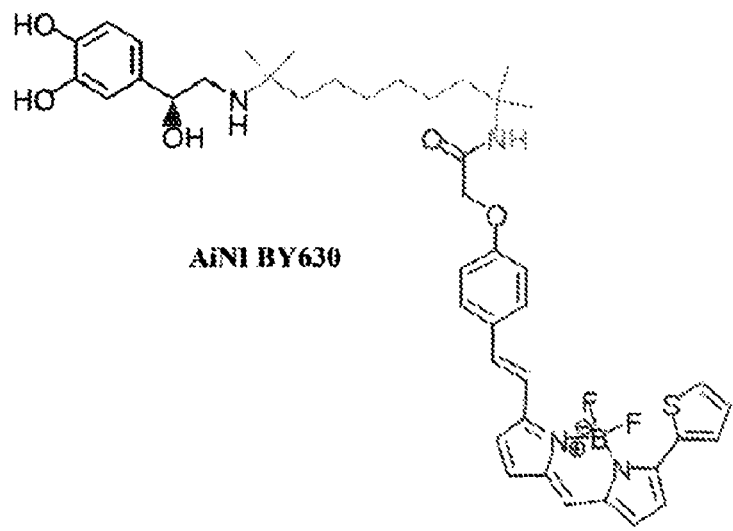
AiNI BY630

FIG. 1.48
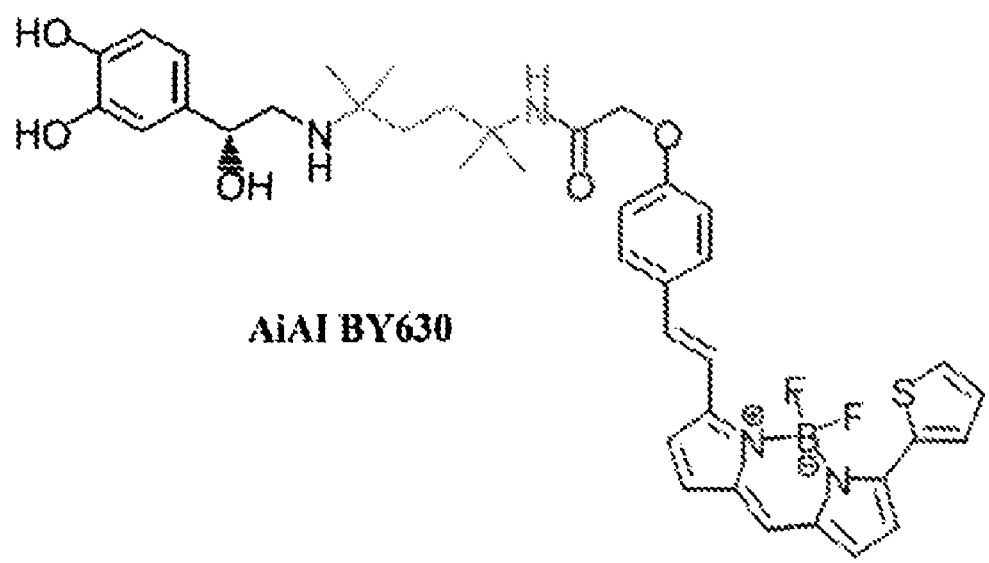
AiAI BY630
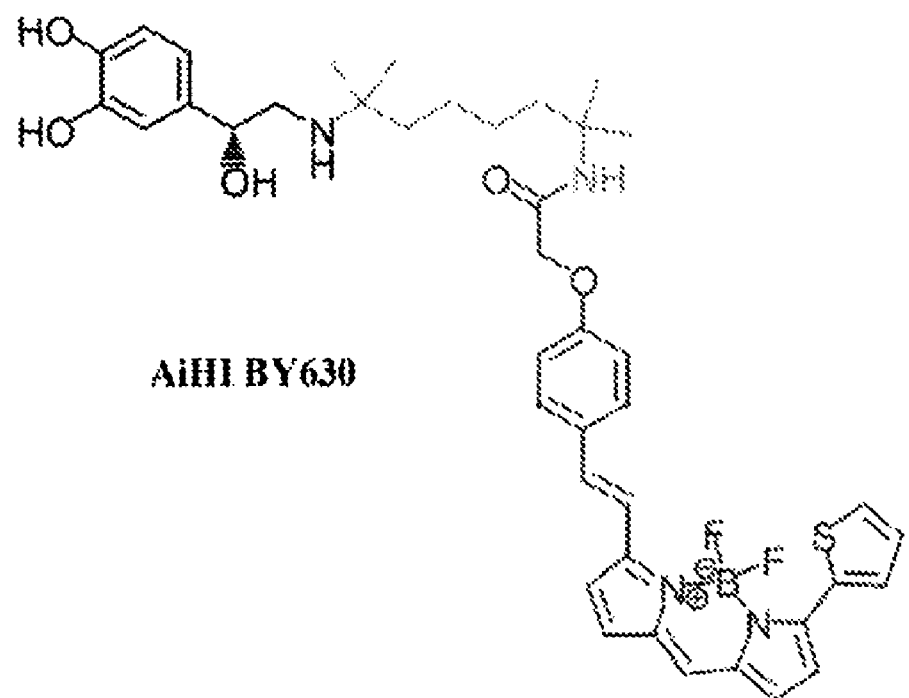
AiHI BY630

FIG. 1.49
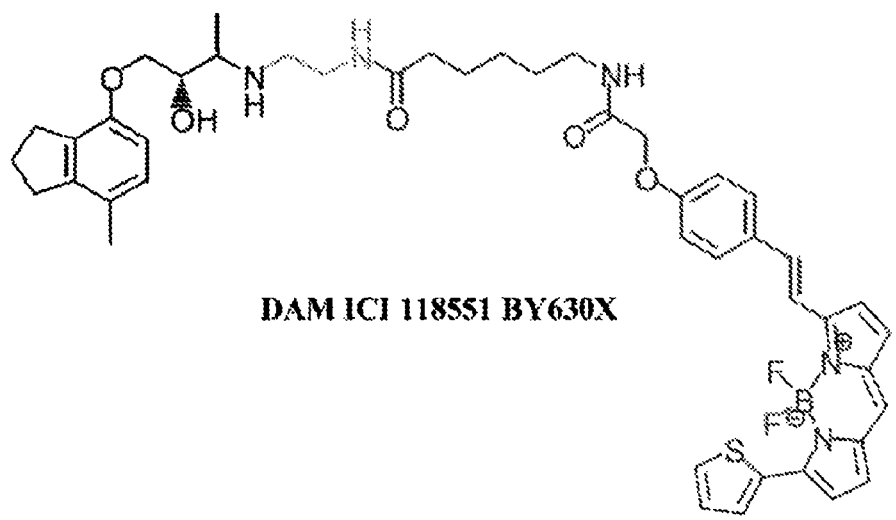
DAM ICI 118551 BY630X
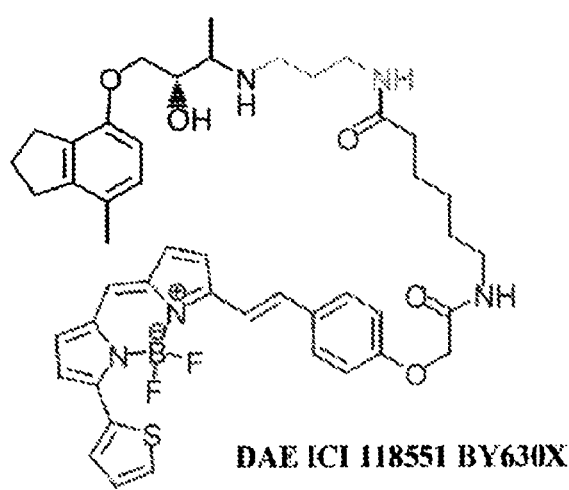
DAE ICI 118551 BY630X
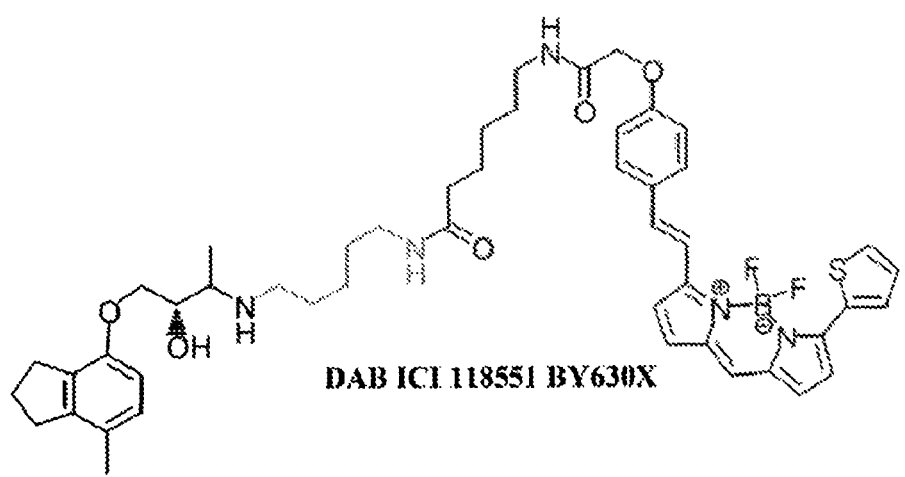
DAB ICI 118551 BY630X

FIG. 1.50
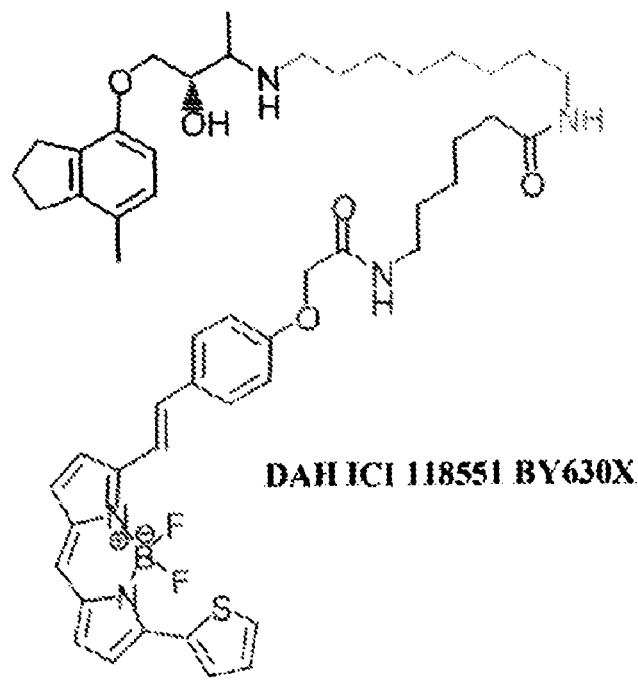
DAH ICI 118551 BY630X
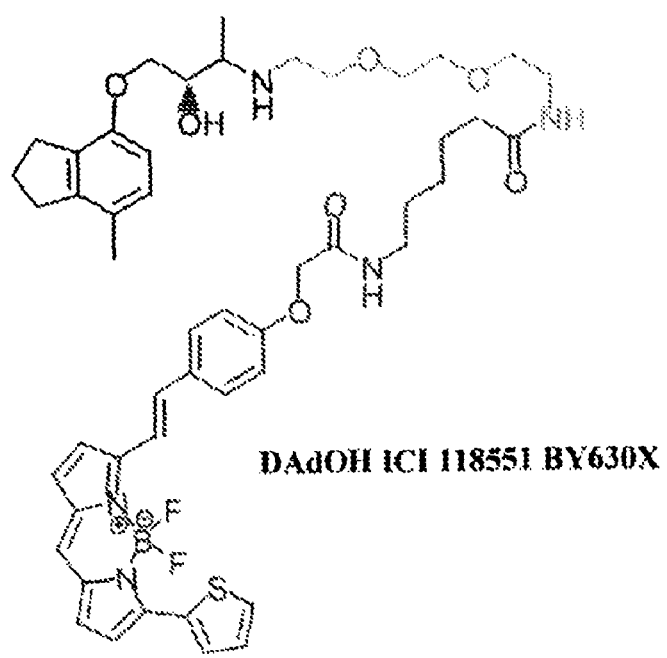
DAdOH ICI 118551 BY630X

FIG. 1.51
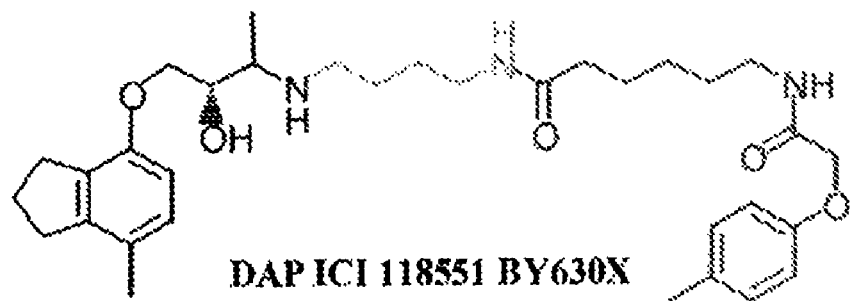
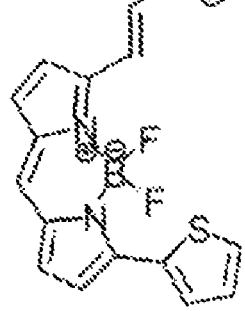
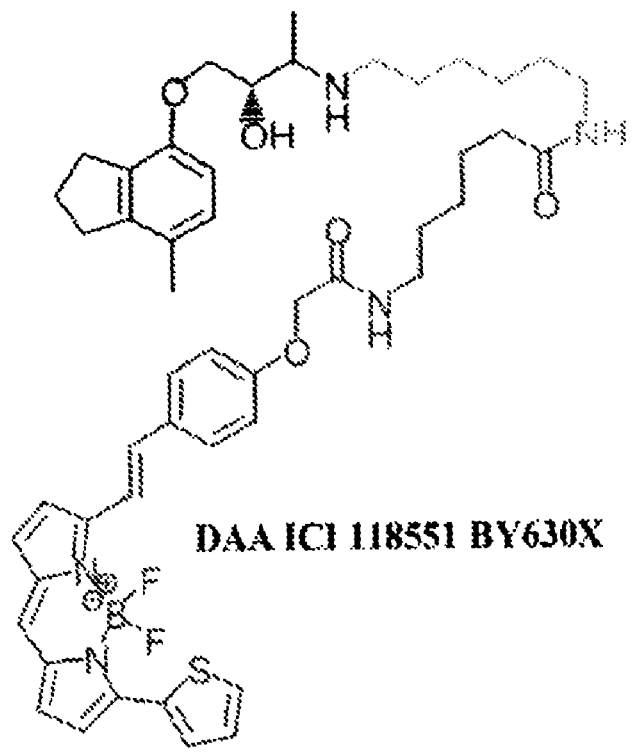

FIG. 1.52
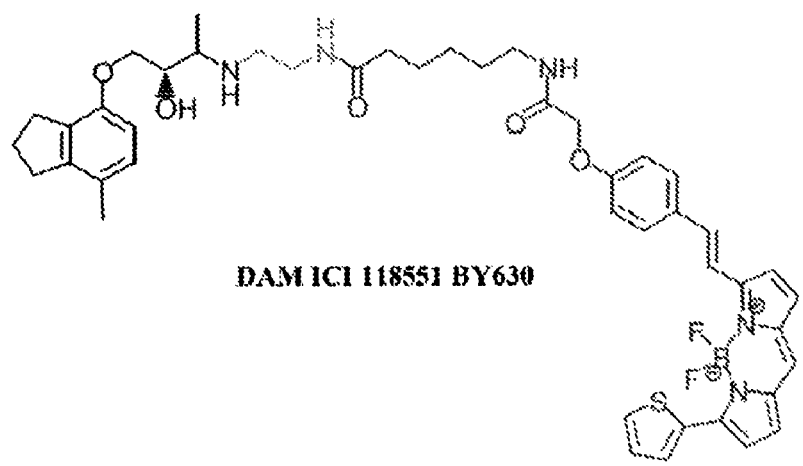
DAM ICI 118551 BY630
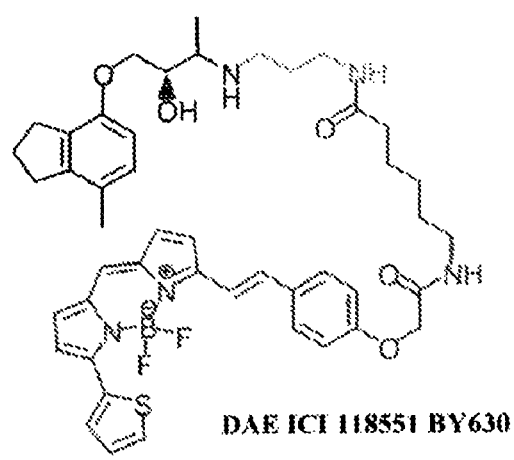
DAE ICI 118551 BY630
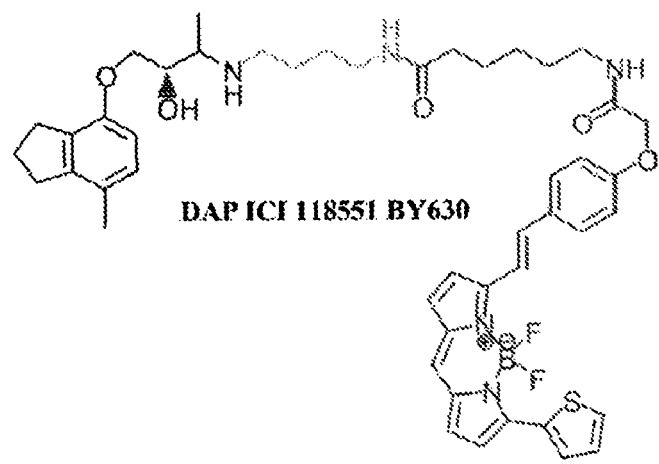
DAP ICI 118551 BY630

FIG. 1.53
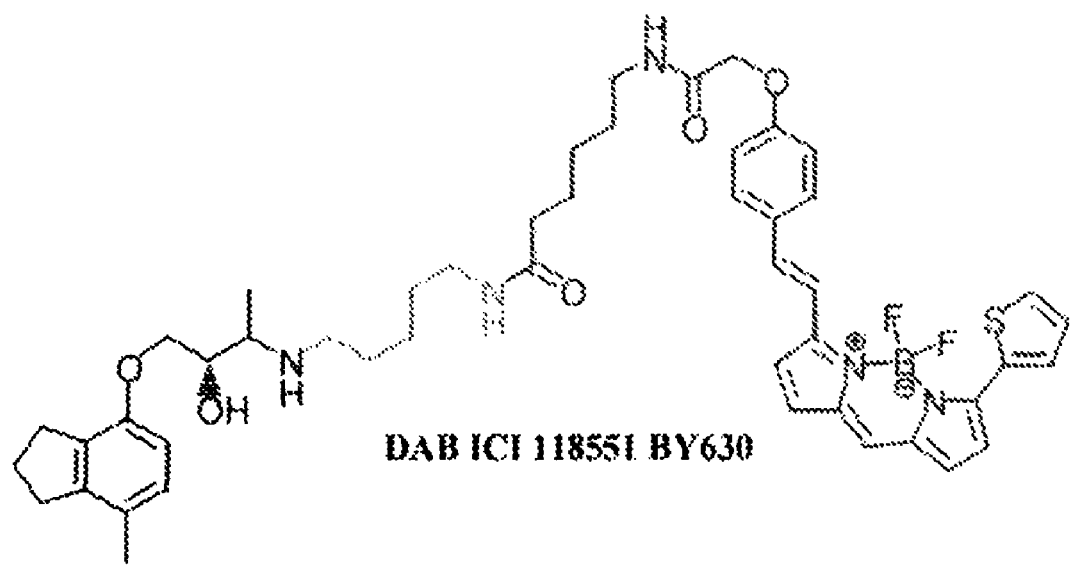
DAB ICI 118551 BY630
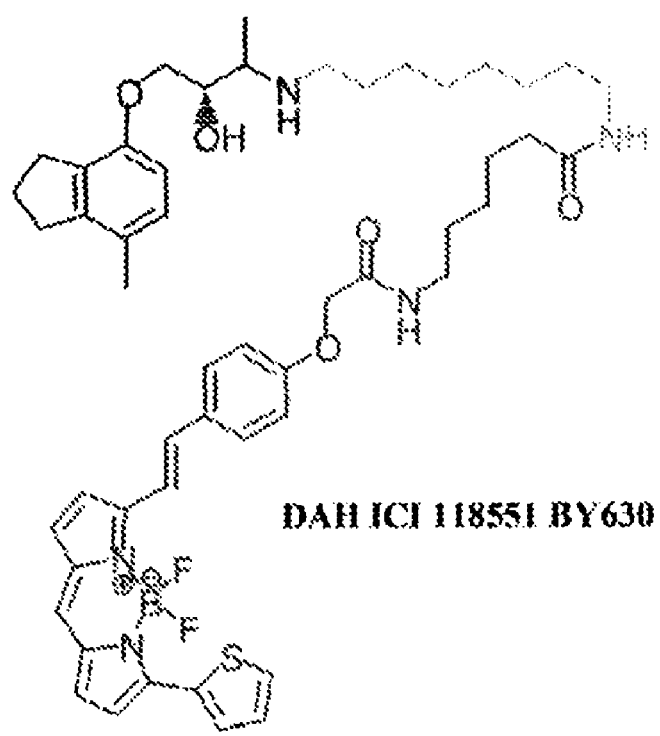
DAH ICI 118551 BY630

FIG. 1.54
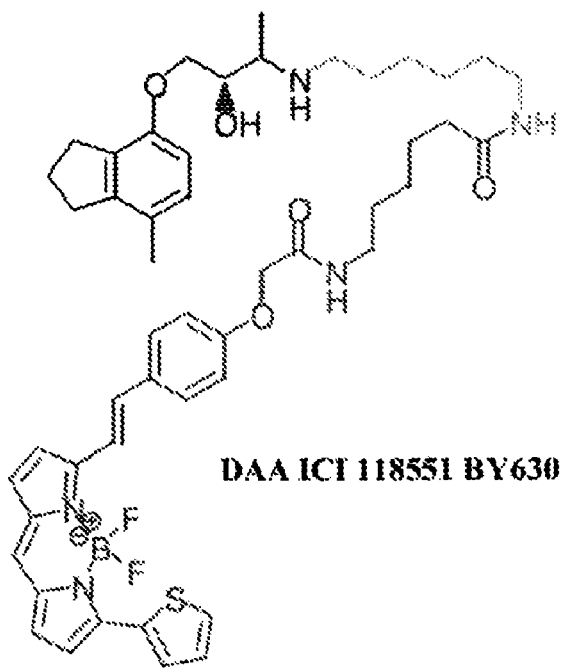
DAA ICI 118551 BY630
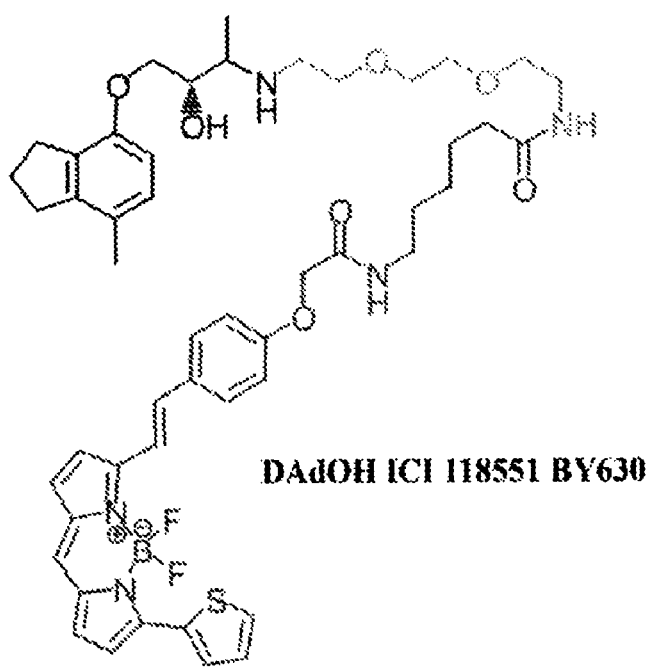
DAdOH ICI 118551 BY630

FIG. 1.55
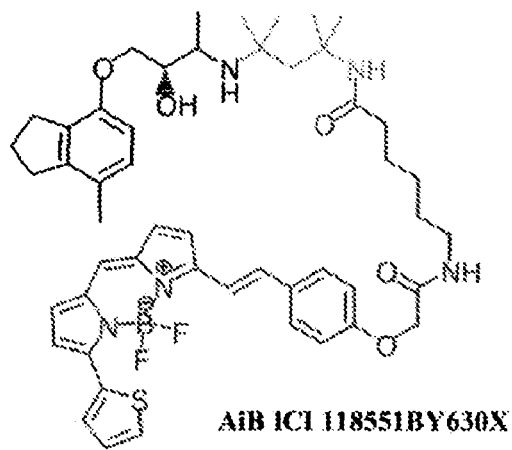
AiB ICI 118551BY630X
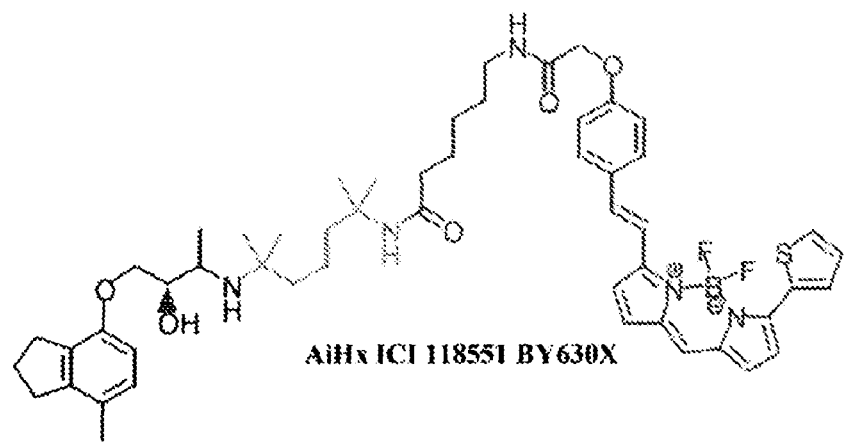
AiHx ICI 118551 BY630X
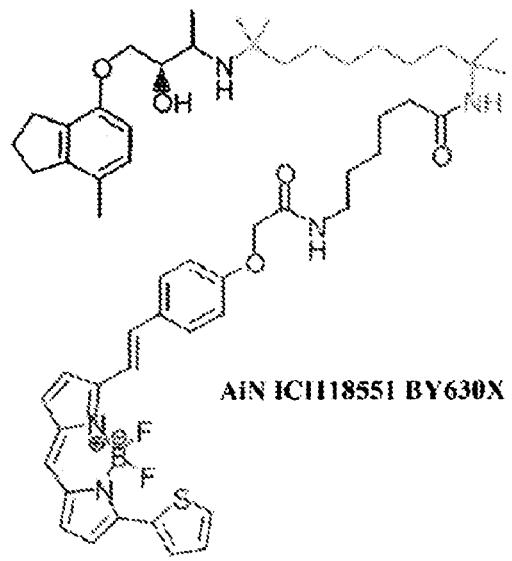
AiN ICI118551 BY630X

FIG. 1.56
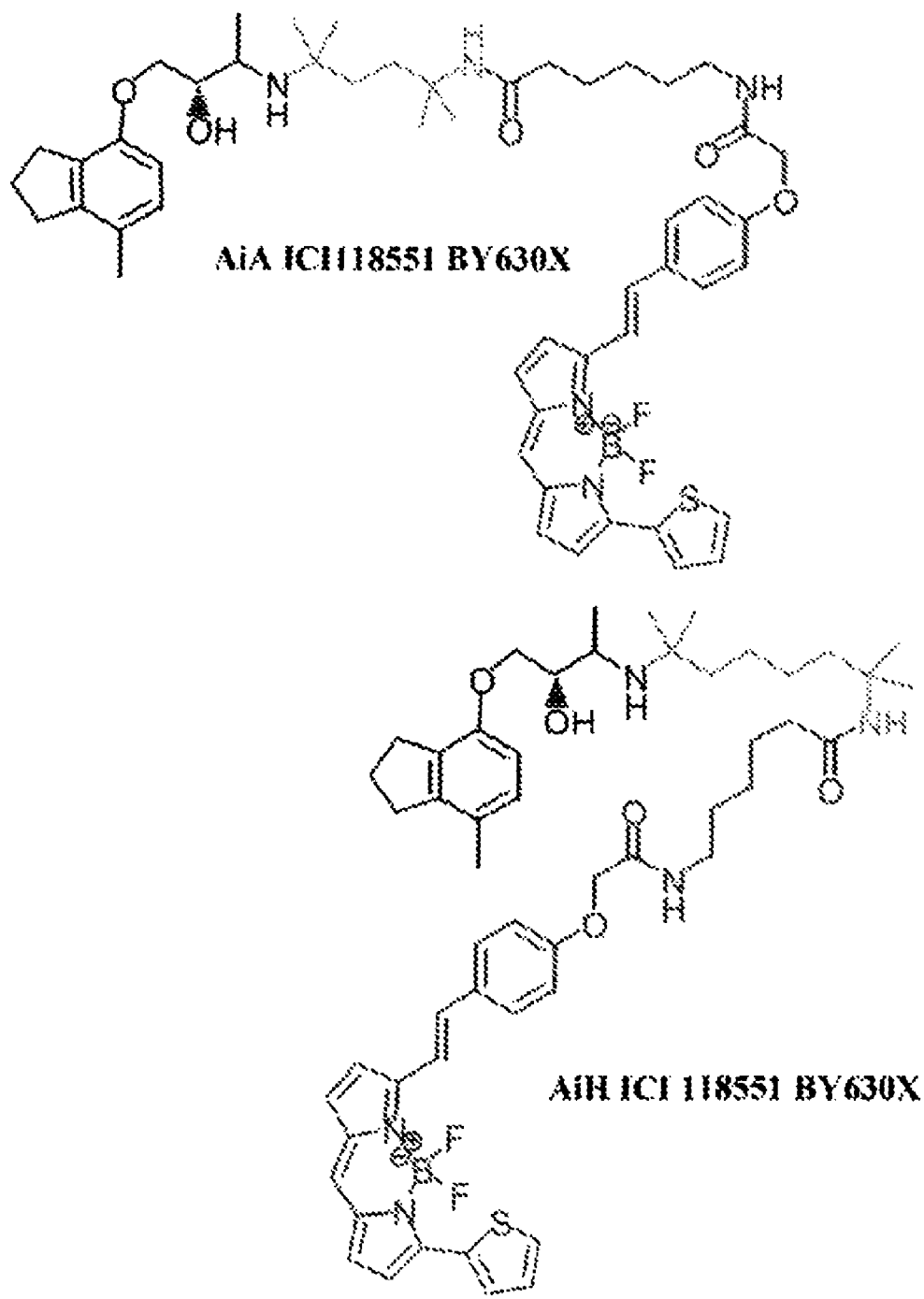

FIG. 1.57
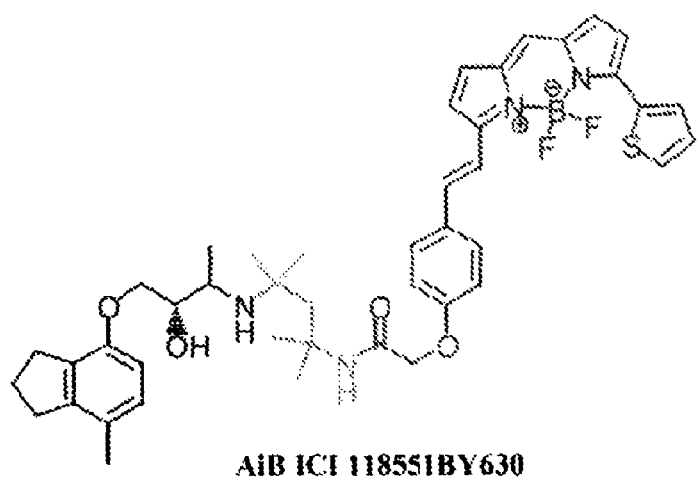
AiB ICI 118551BY630
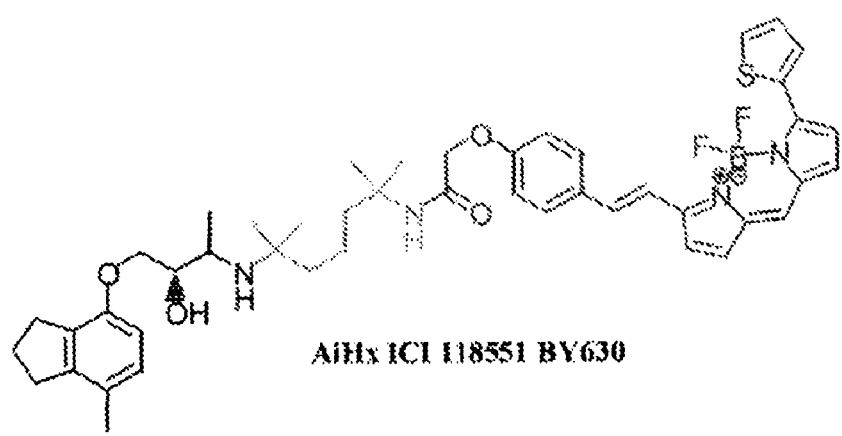
AiHx ICI 118551 BY630
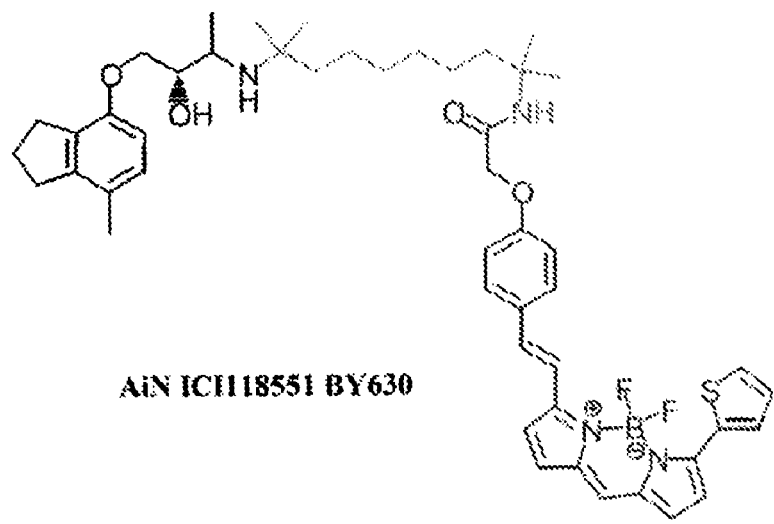
AiN ICI118551 BY630

FIG. 1.58
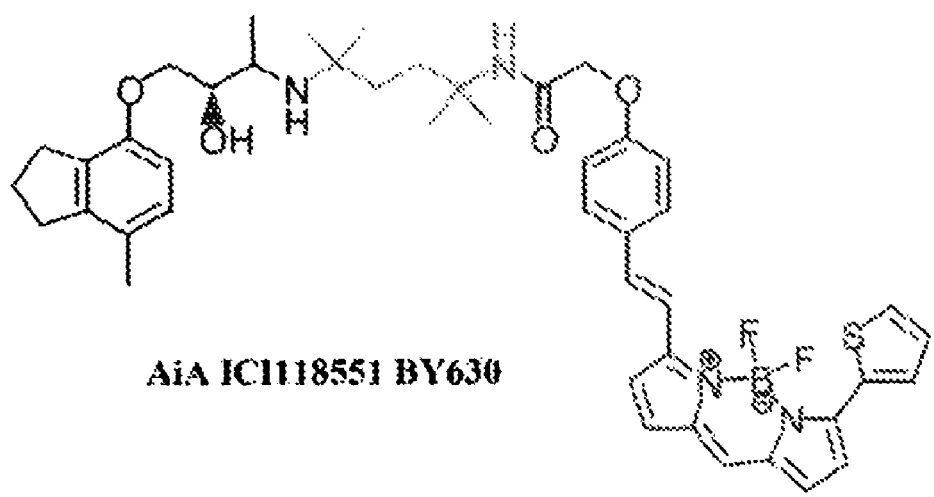
AiA ICI118551 BY630
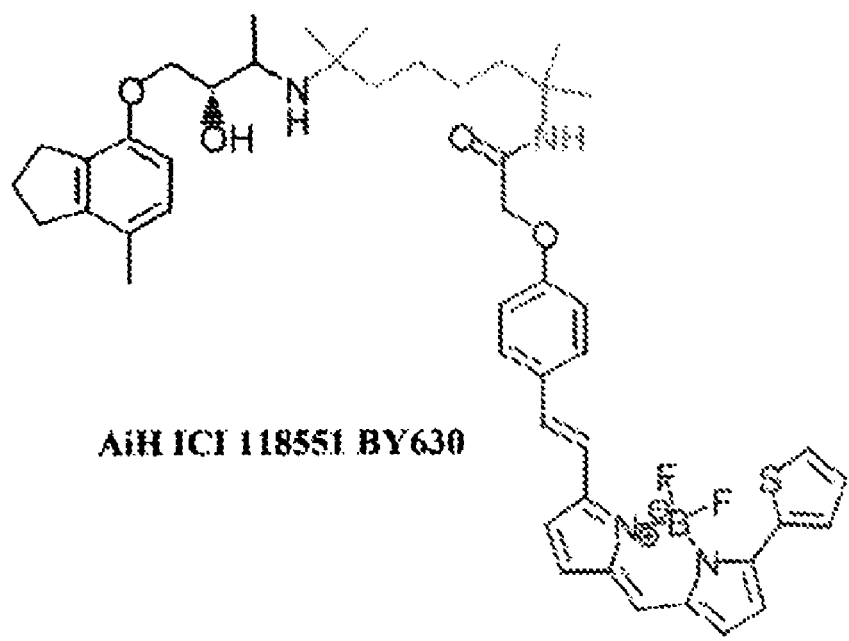
AiH ICI 118551 BY630

FIG. 1.59
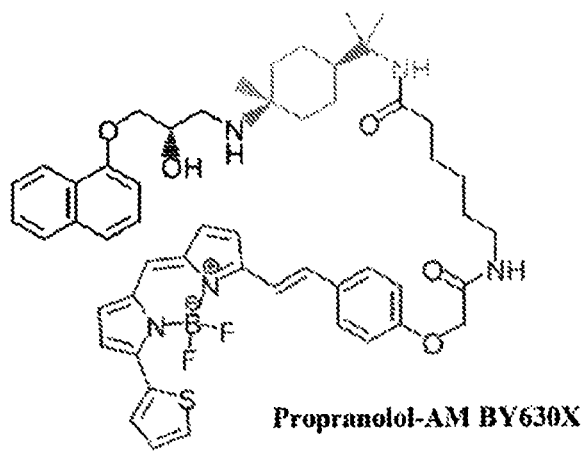
Propranolol-AM BY630X
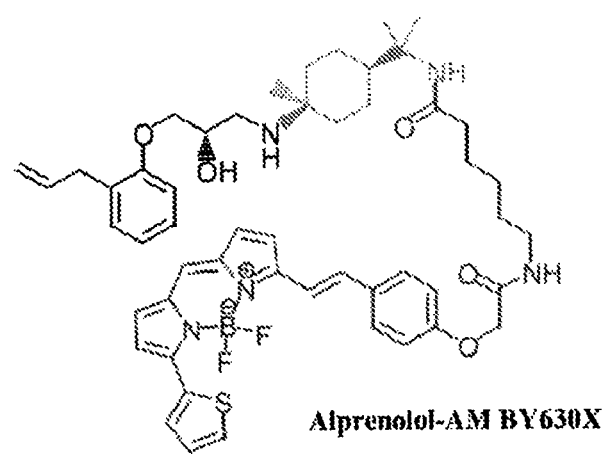
Alprenolol-AM BY630X
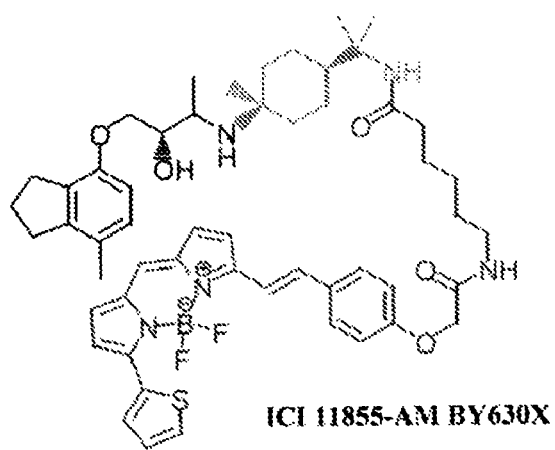
ICI 11855-AM BY630X FIG. 1.60
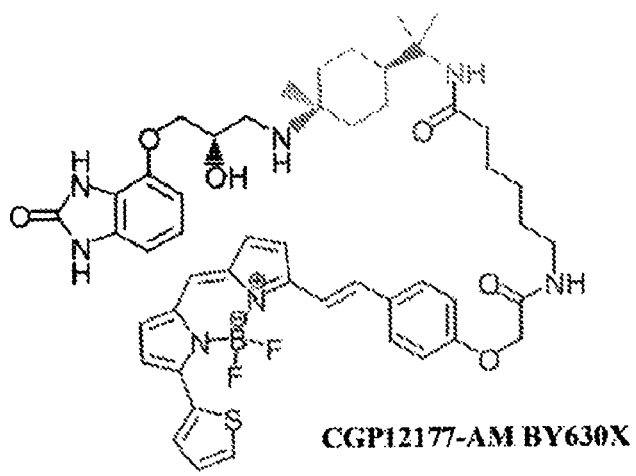
CGP12177-AM BY630X
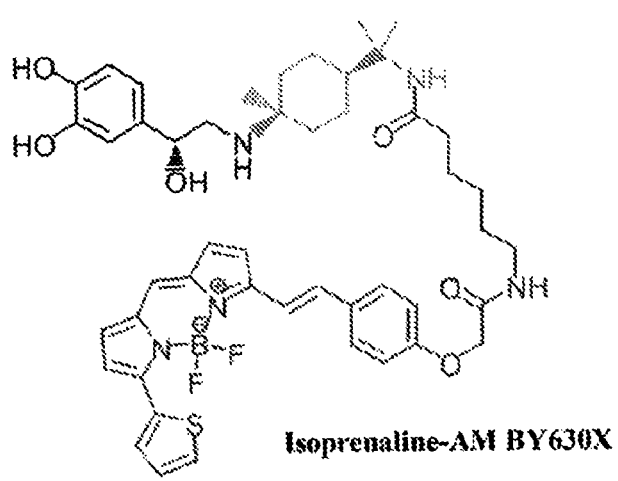
Isoprenaline-AM BY630X
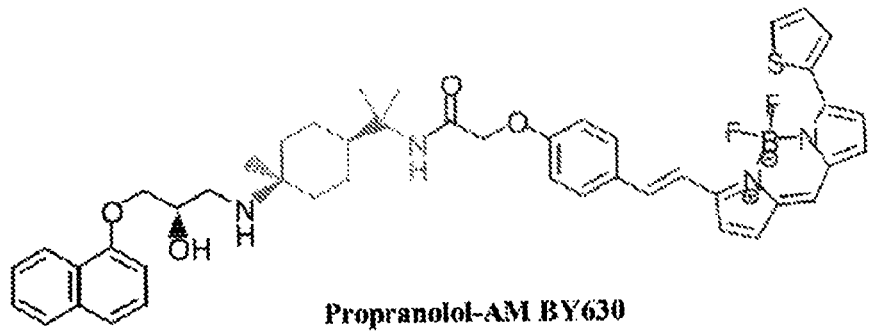
Propranolol-AM BY630

FIG. 1.61
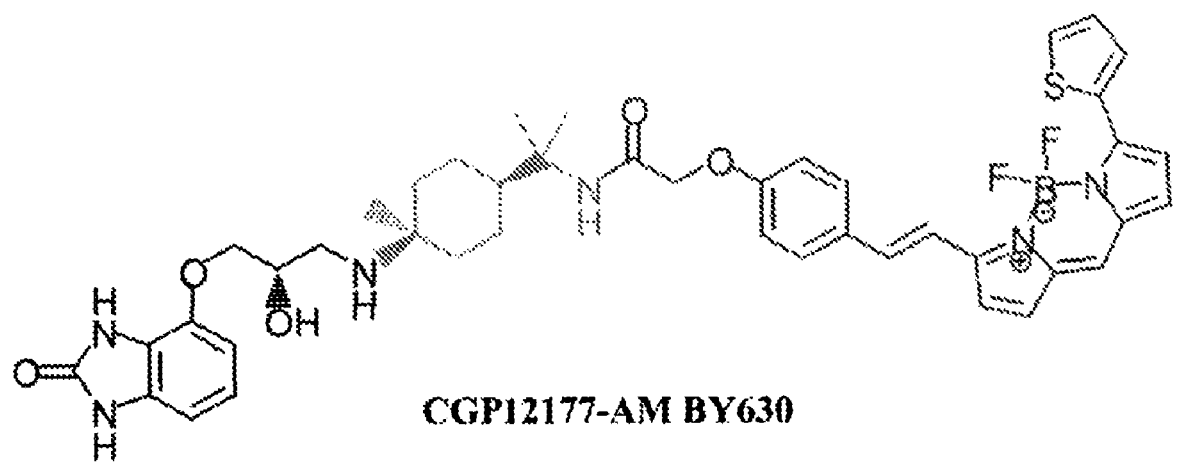
CGP12177-AM BY630
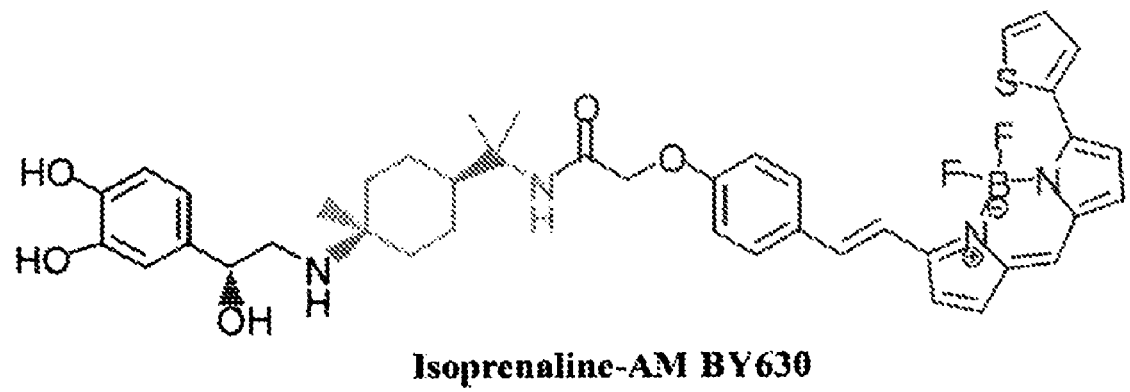
Isoprenaline-AM BY630

FIG. 1.62
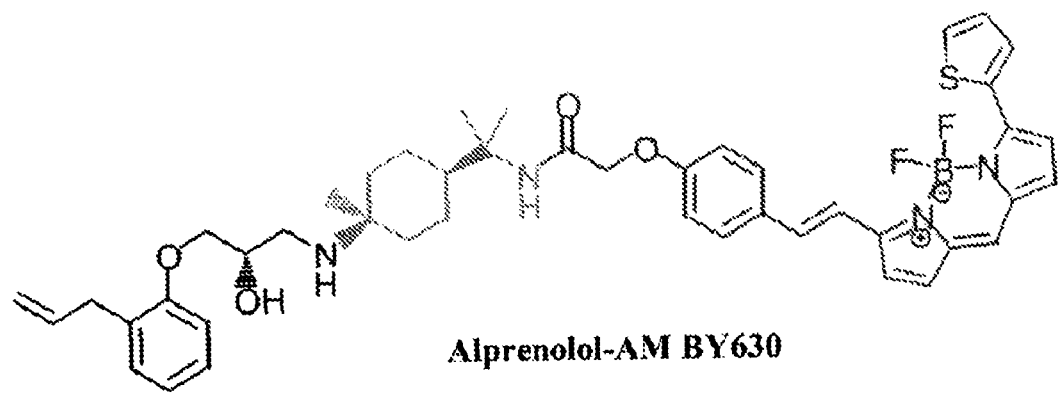
Alprenolol-AM BY630
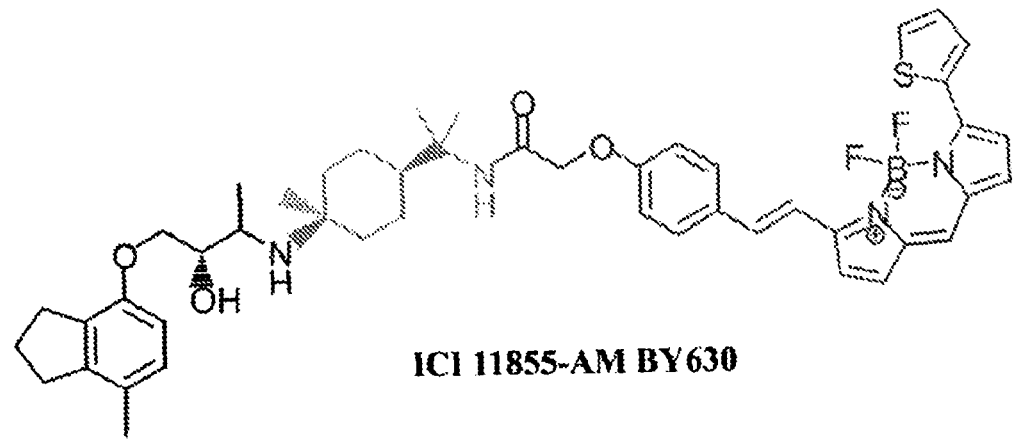
ICI 11855-AM BY630

FIG. 1.63
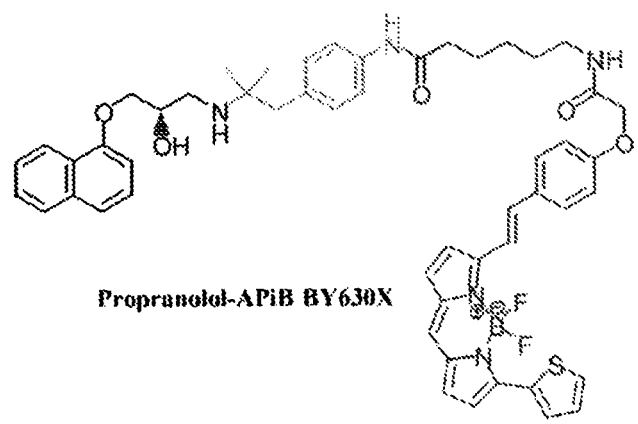
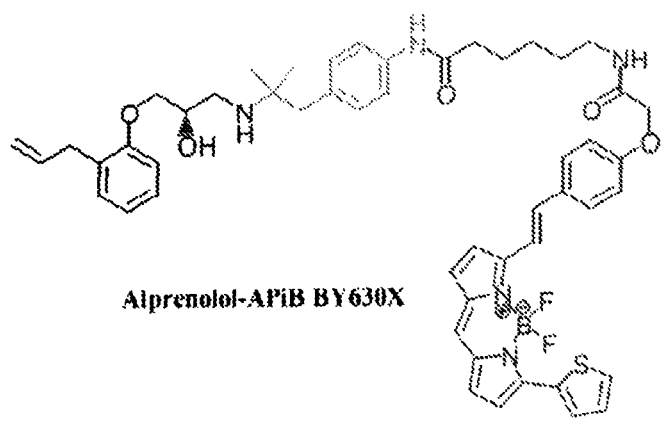
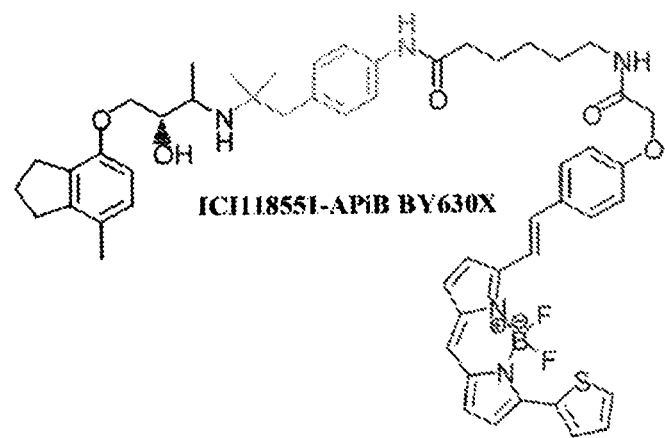

FIG. 1.64
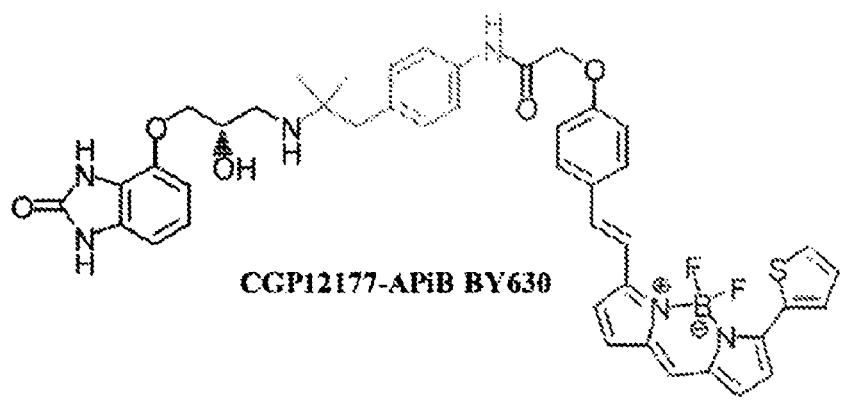
CGP12177-APiB BY630
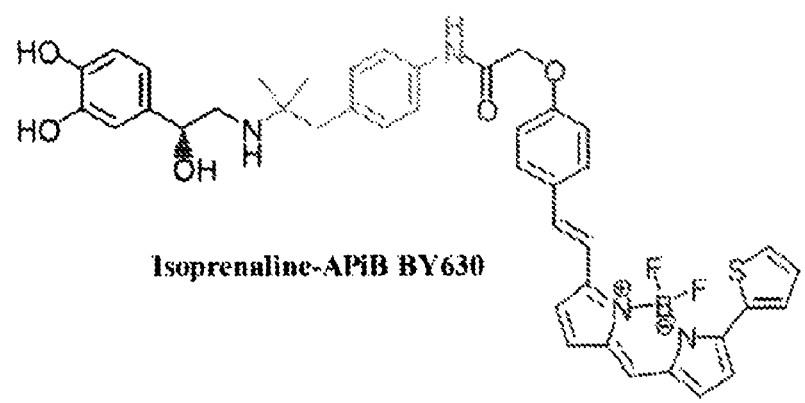
Isoprenaline-APiB BY630
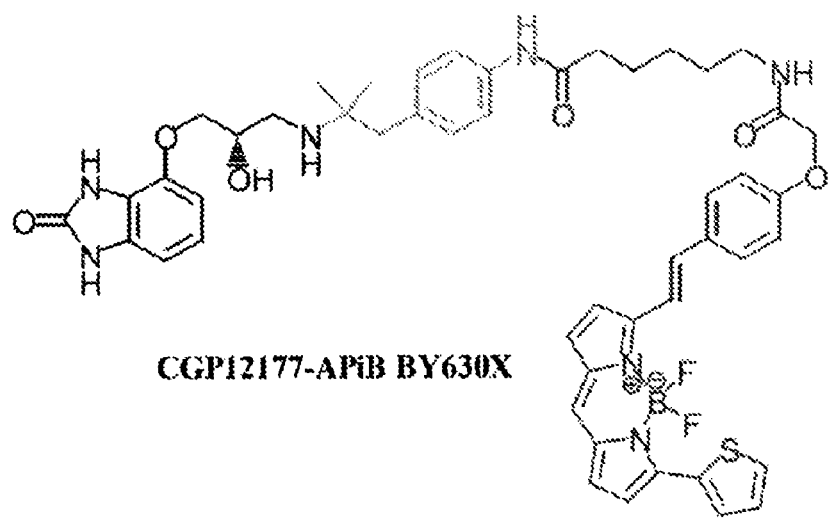
CGP12177-APiB BY630X FIG. 1.65
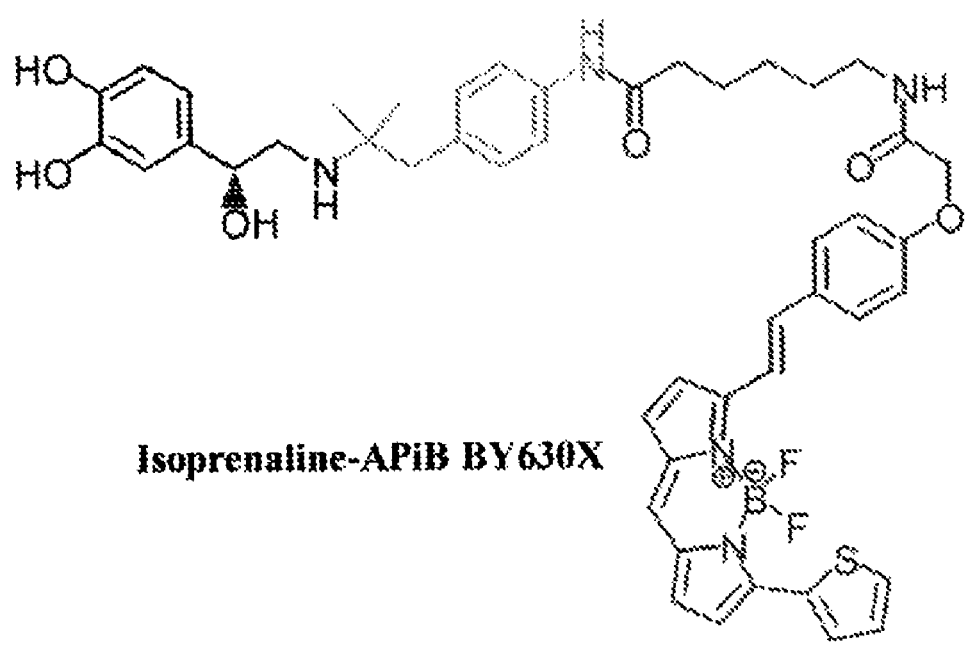
Isoprenaline-APiB BY630X
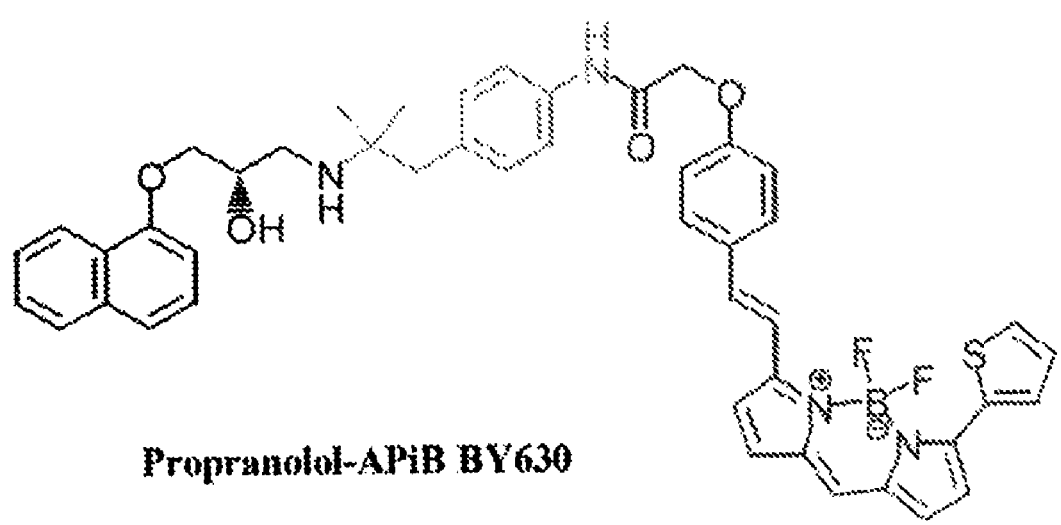
Propranolol-APiB BY630

FIG. 1.66
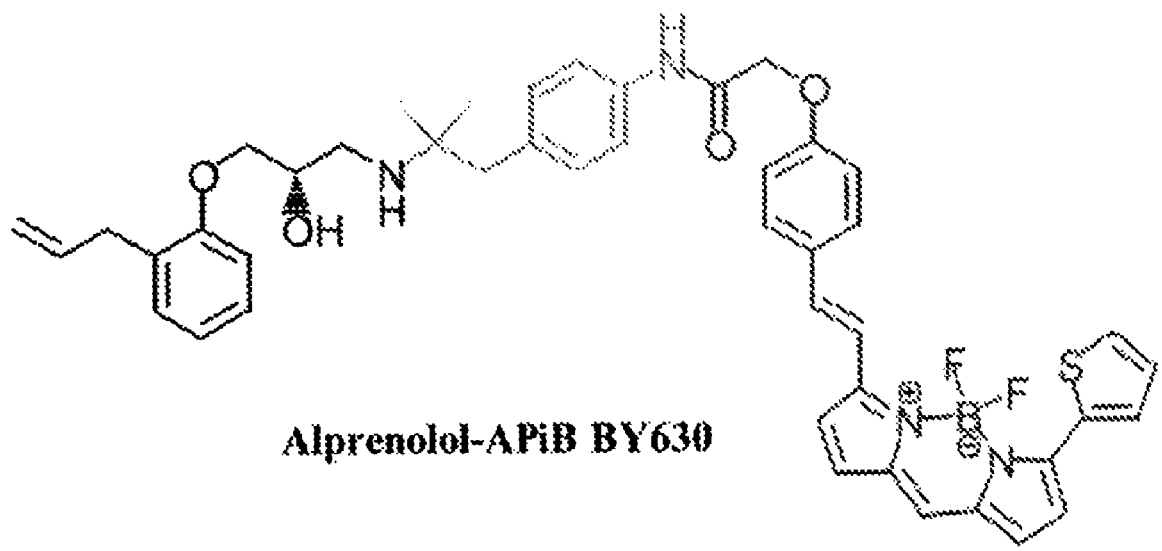
Alprenolol-APiB BY630
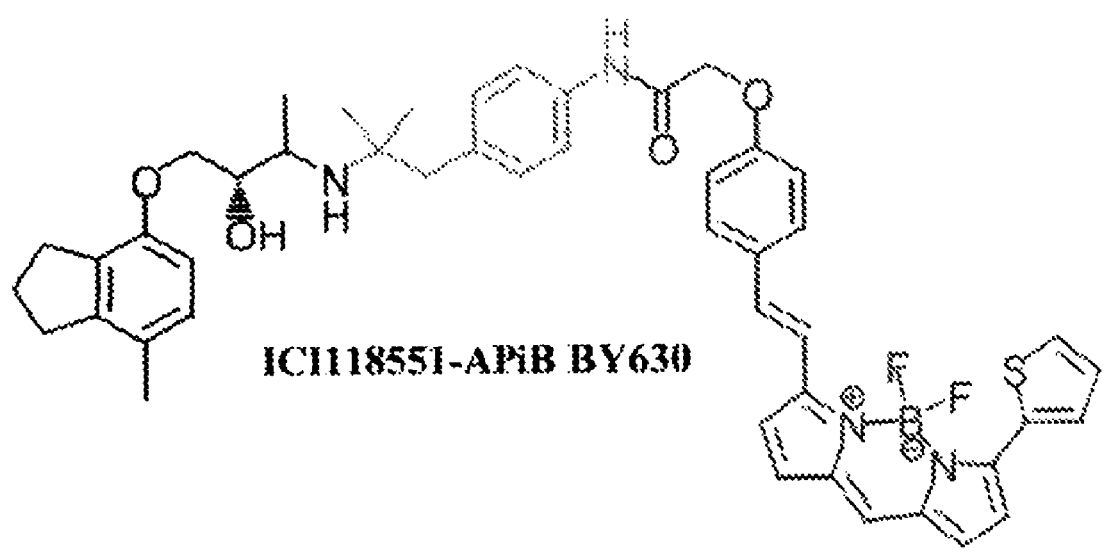
ICI118551-APiB BY630

Fig 1.67
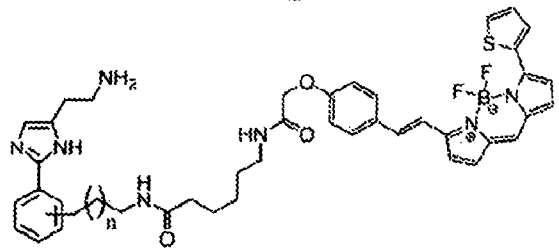
n = 0; 2-(2,3 or 4-aminoethylphenyl)histamine BODIPY 630/650X (AEPH BY630X)
n = 1; APrPH BY630X
n = 2; ABPH BY630X
n = 3; APPH BY630X
n = 4; AHxPH BY630X
n = 5; AHPH BY630X
n = 6; AOPH BY630X
n = 7; ANPH BY630X
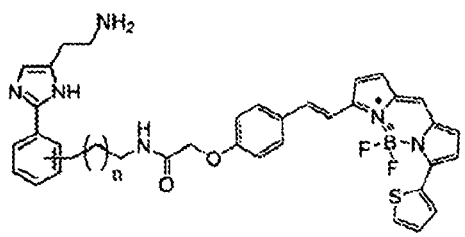
n = 0; 2-(2,3 or 4-aminoethylphenyl)histamine BODIPY 630/650 (AEPH BY630)
n = 1; APrPH BY630
n = 2; ABPH BY630
n = 3; APPH BY630
n = 4; AHxPH BY630
n = 5; AHPH BY630
n = 6; AOPH BY630
n = 7; ANPH BY630
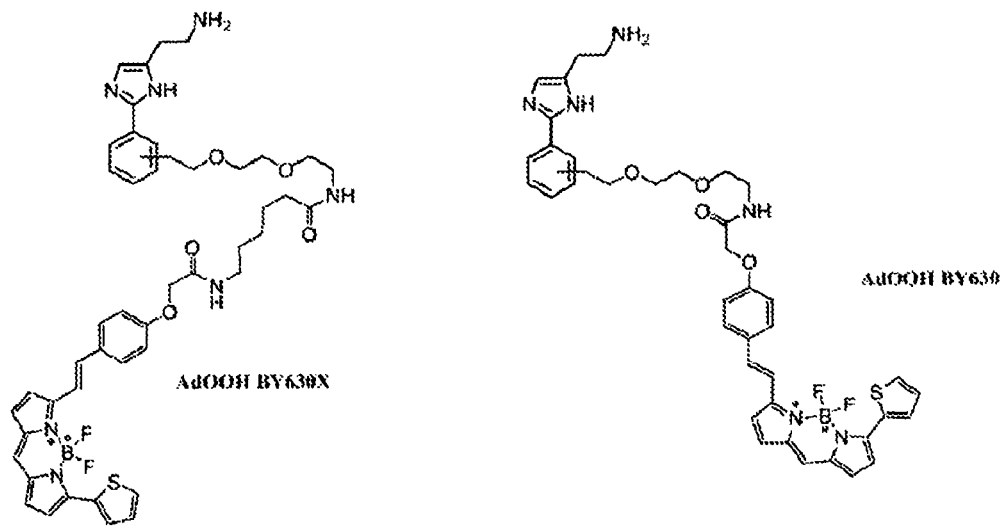
AdOOH BY630X
AdOOH BY630

Fig 1.68
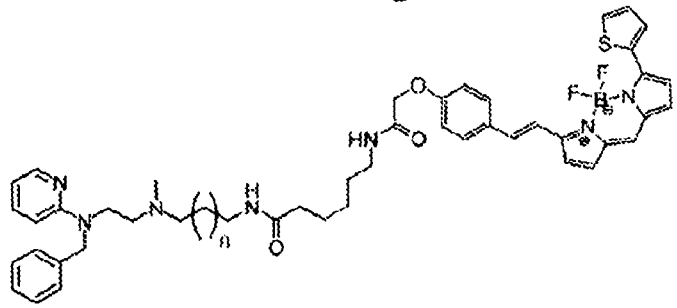
n = 0; Desmethylaminoethyl Mepyramine BODIPY 630/650X (DMAEM BY603X)
n = 1; DMAPrM BY630X
n = 2; DMABM BY630X
n = 3; DMAPM BY630X
n = 4; DMAHxM BY630X
n = 5; DMAHM BY630X
n = 6; DMAOM BY630X
n = 7; DMANM BY630X
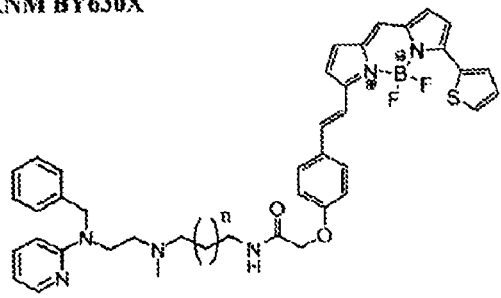
n = 0; Desmethylaminoethyl Mepyramine BODIPY 630/650X (DMAEM BY603)
n = 1; DMAPrM BY630
n = 2; DMABM BY630
n = 3; DMAPM BY630
n = 4; DMAHxM BY630
n = 5; DMAHM BY630
n = 6; DMAOM BY630
n = 7; DMANM BY630
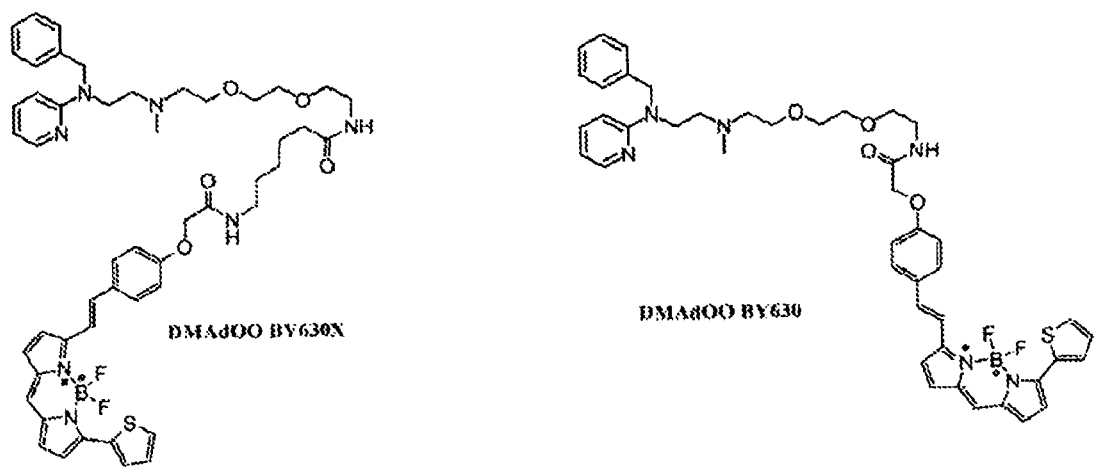
DMAdOO BY630X
DMAdOO BY630

Fig 1.69
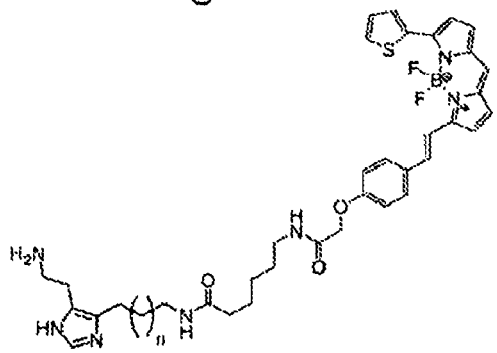
n = 0; 4-aminoethylhistamine BODIPY 630/650X (AEH BY603X)
n = 1; APrH BY630X
n = 2; ABH BY630X
n = 3; APH BY630X
n = 4; AHxH BY630X
n = 5; AHH BY630X
n = 6; AOH BY630X
n = 7; ANH BY630X
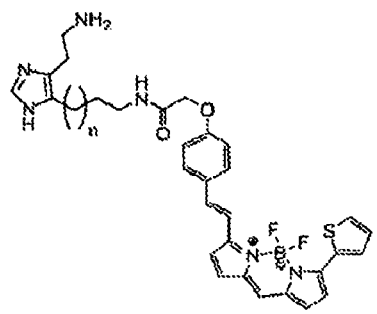
n = 0; 4-aminoethylhistamine BODIPY 630/650X (AEH BY603)
n = 1; APrH BY630
n = 2; ABH BY630
n = 3; APH BY630
n = 4; AHxH BY630
n = 5; AHH BY630
n = 6; AOH BY630
n = 7; ANH BY630
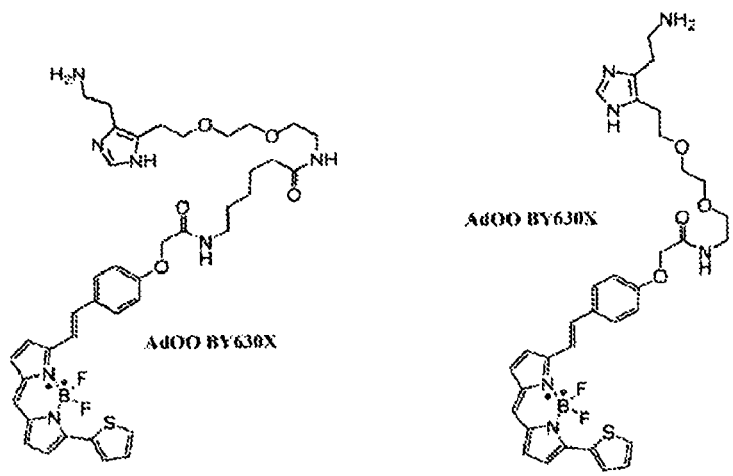
AdOO BY630X
AdOO BY630X Fig 1.70
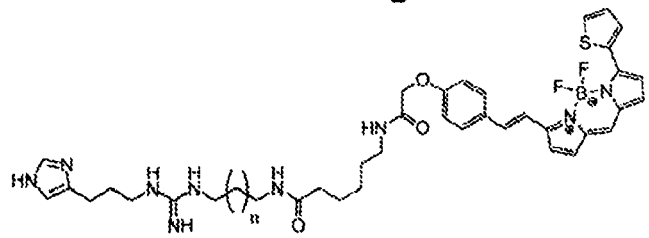
n = 0; 1-(3-(1H-imidazol-4-yl)propyl)-3-aminoethyl guanidine BODIPY 630/650X (IPAEG BY603X)
n = 1; IPAPrG BY630X
n = 2; IPABG BY630X
n = 3; IPAPG BY630X
n = 4; IPAHxG BY630X
n = 5; IPAHG BY630X
n = 6; IPAOG BY630X
n = 7; IPANG BY630X
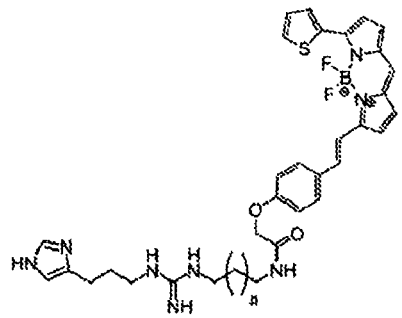
n = 0; 1-(3-(1H-imidazol-4-yl)propyl)-3-aminoethyl guanidine BODIPY 630/650 (IPAEG BY603)
n = 1; IPAPrG BY630
n = 2; IPABG BY630
n = 3; IPAPG BY630
n = 4; IPAHxG BY630
n = 5; IPAHG BY630
n = 6; IPAOG BY630
n = 7; IPANG BY630
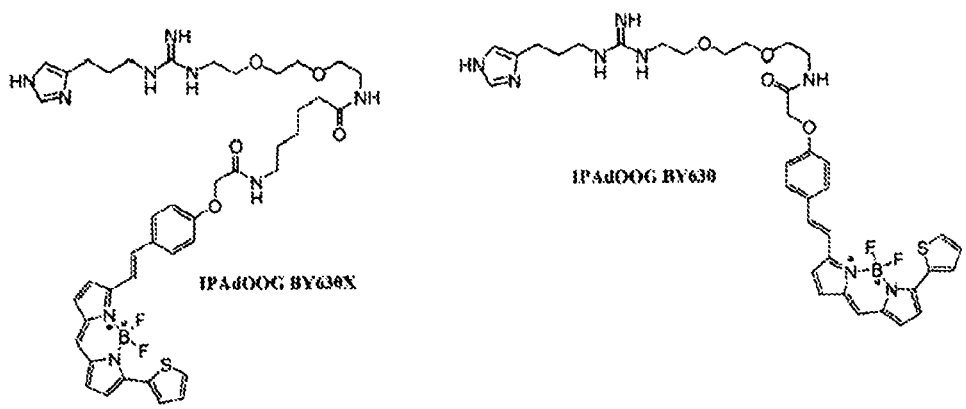

Fig 1.71
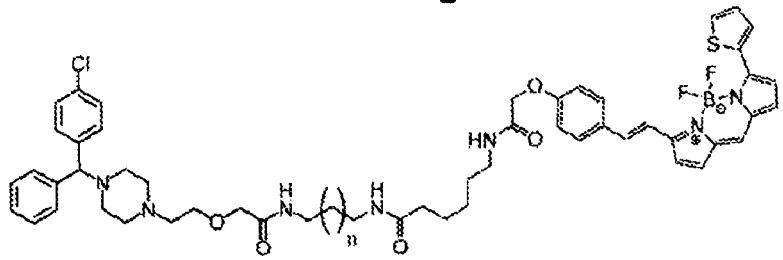
n = 0; Cetirizine aminoethylamide BODIPY 630/650X (CAEA BY603X)
n = 1; CAPrA BY630X
n = 2; CABA BY630X
n = 3; CAPA BY630X
n = 4; CAHxA BY630X
n = 5; CAHA BY630X
n = 6; CAOA BY630X
n = 7; CANA BY630X
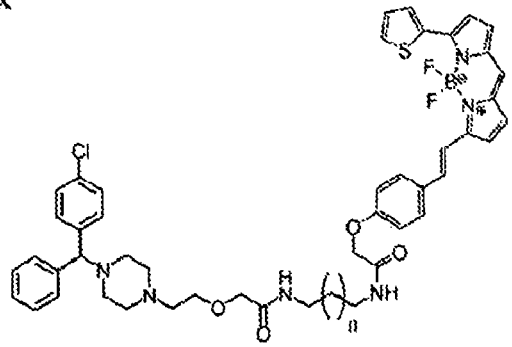
n = 0; Cetirizine aminoethylamide BODIPY 630/650 (CAEA BY603)
n = 1; CAPrA BY630
n = 2; CABA BY630
n = 3; CAPA BY630
n = 4; CAHxA BY630
n = 5; CAHA BY630
n = 6; CAOA BY630
n = 7; CANA BY630
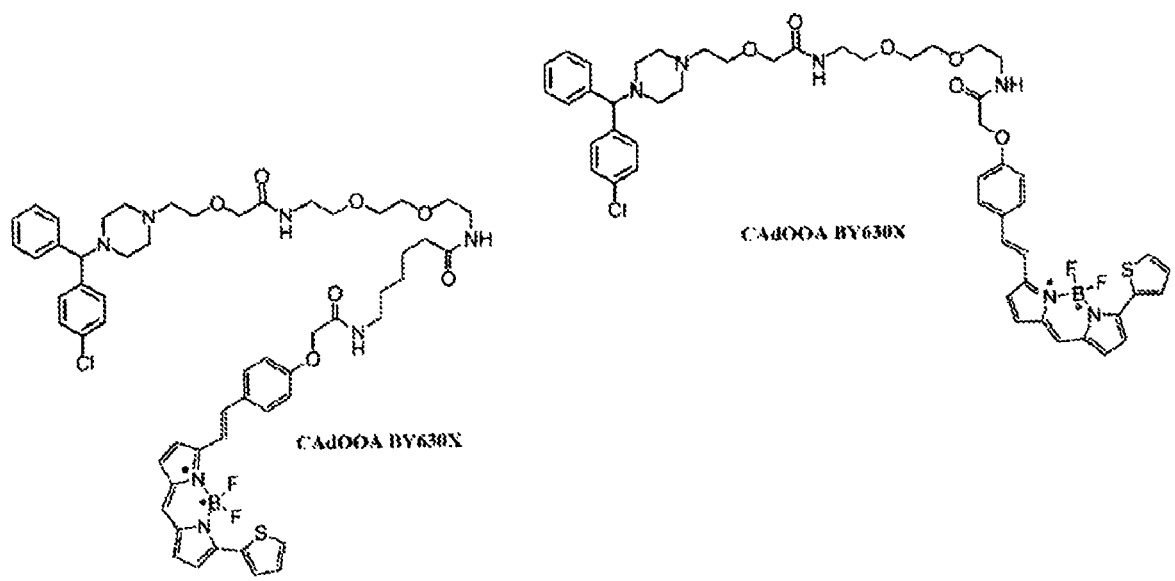
CAdOOA BY630X
CAdOOA BY630X FIG 1.72
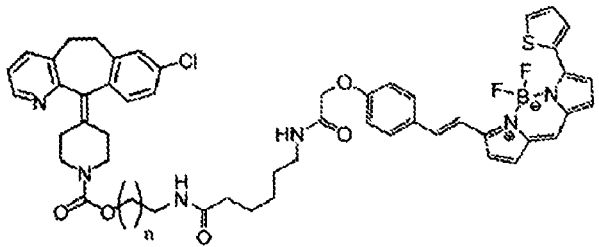
n = 1; Aminoloratidine BODIPY 630/650X (AL BY603X)
n = 2; AML BY630X
n = 3; AEL BY630X
n = 4; APrL BY630X
n = 5; ABL BY630X
n = 6; APL BY630X
n = 7; AHxL BY630X
n = 8; AHL BY630X
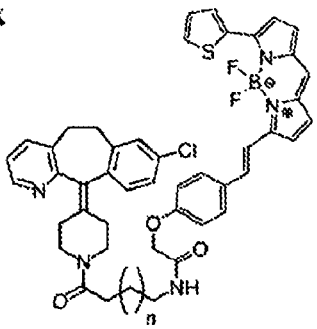
n = 1; Aminoloratidine BODIPY 630/650 (AL BY603)
n = 2; AML BY630
n = 3; AEL BY630
n = 4; APrL BY630
n = 5; ABL BY630
n = 6; APL BY630
n = 7; AHxL BY630
n = 8; AHL BY630
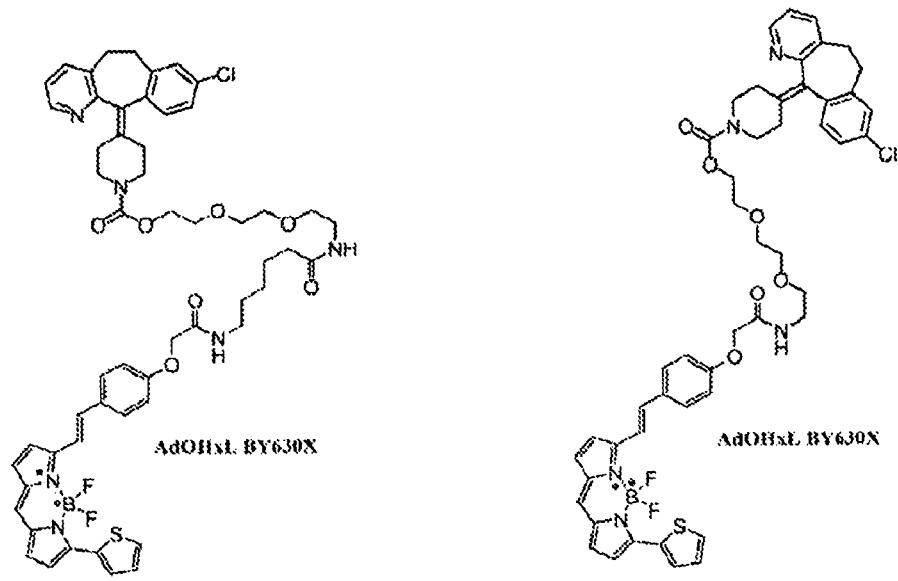
AdOHxL BY630X      AdOHxL BY630X

FIG 1.73

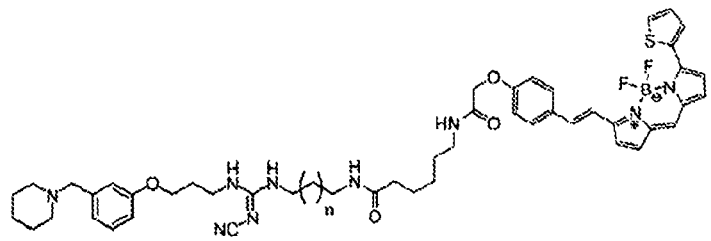

n = 0; 3-Aminoethyl-2-cyano-1-(3-(3-(piperidin-1-ylmethyl)phenoxy)propyl)guanidine BODIPY 630/650X
 (AECPG BY603X)
n = 1; APrCPG BY630X
n = 2; ABCPG BY630X
n = 3; APCPG BY630X
n = 4; AHxCPG BY630X
n = 5; AHCPG BY630X
n = 6; AOCPG BY630X
n = 7; ANCPG BY630X

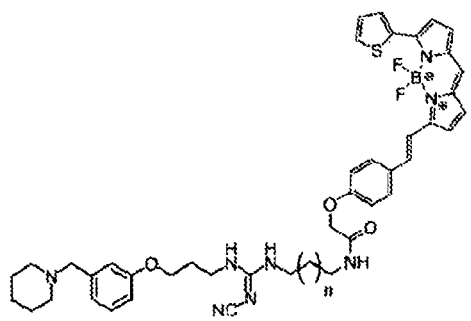

n = 0; 3-Aminoethyl-2-cyano-1-(3-(3-(piperidin-1-ylmethyl)phenoxy)propyl)guanidine BODIPY 630/650X
 (AECPG BY603X)
n = 1; APrCPG BY630X
n = 2; ABCPG BY630X
n = 3; APCPG BY630X
n = 4; AHxCPG BY630X
n = 5; AHCPG BY630X
n = 6; AOCPG BY630X
n = 7; ANCPG BY630X

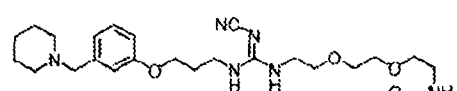
AdOOCPG BY630X

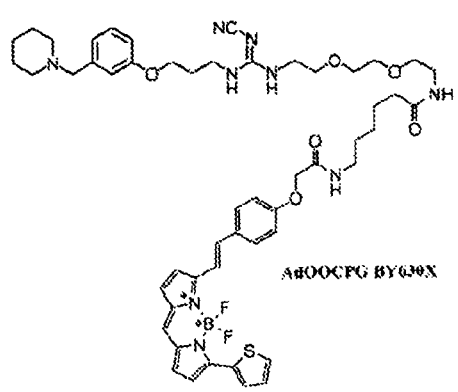
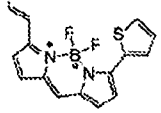
AdOOCPG BY630X

FIG 1.74
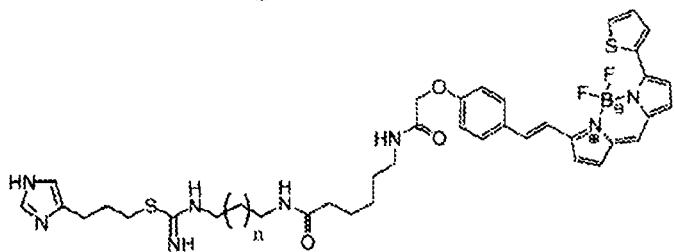
n = 0; 3-(1H-imidazol-4-yl)propyl 2-aminoethylcarbamimidothioate BODIPY 630/650X (IAET BY603X)
n = 1; IAPrT BY630X
n = 2; IABT BY630X
n = 3; IAPT BY630X
n = 4; IAHxT BY630X
n = 5; IAHT BY630X
n = 6; IAOT BY630X
n = 7; IANT BY630X
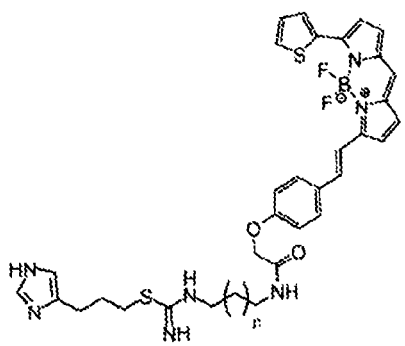
n = 0; 3-(1H-imidazol-4-yl)propyl 2-aminoethylcarbamimidothioate BODIPY 630/650 (IAET BY603)
n = 1; IAPrT BY630
n = 2; IABT BY630
n = 3; IAPT BY630
n = 4; IAHxT BY630
n = 5; IAHT BY630
n = 6; IAOT BY630
n = 7; IANT BY630
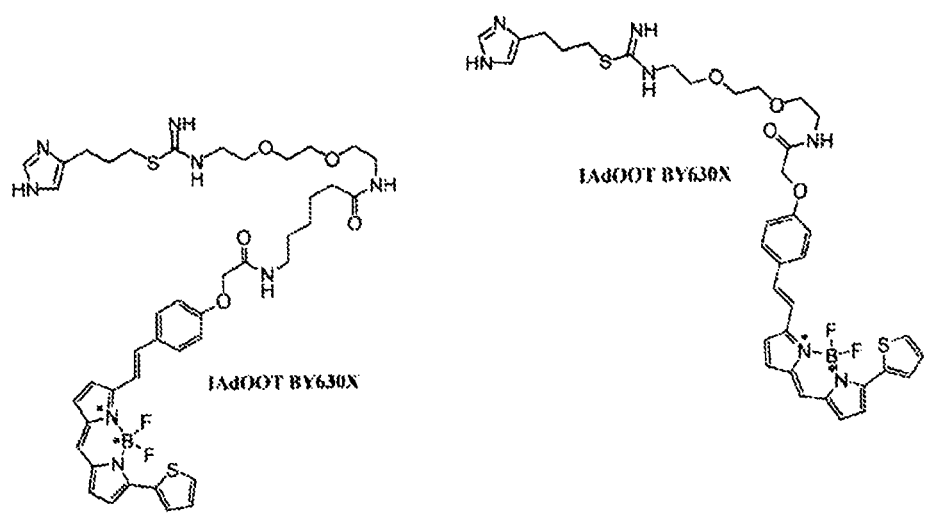
IAdOOT BY630X
IAdOOT BY630X

FIG 1.75

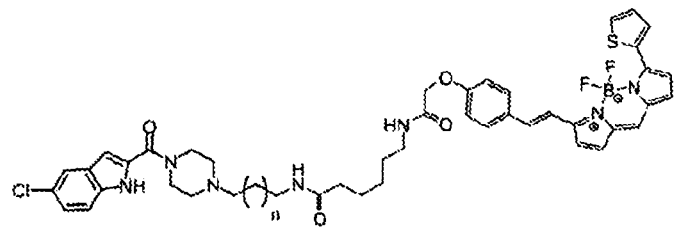

n = 0; Aminomethyl-JNJ 7777120 BODIPY 630/650X
n = 1; Aminoethyl-JNJ 7777120 BODIPY 630/650X
n = 2; Aminopropyl-JNJ 7777120 BODIPY 630/650X
n = 3; Aminobutyl-JNJ 7777120 BODIPY 630/650X
n = 4; Aminopentyl-JNJ 7777120 BODIPY 630/650X
n = 5; Aminohexyl-JNJ 7777120 BODIPY 630/650X
n = 6; Aminoheptyl-JNJ 7777120 BODIPY 630/650X
n = 7; Aminooctyl-JNJ 7777120 BODIPY 630/650X

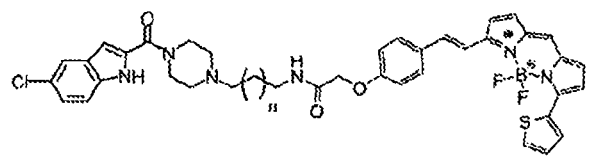

n = 0; Aminomethyl-JNJ 7777120 BODIPY 630/650
n = 1; Aminoethyl-JNJ 7777120 BODIPY 630/650
n = 2; Aminopropyl-JNJ 7777120 BODIPY 630/650
n = 3; Aminobutyl-JNJ 7777120 BODIPY 630/650
n = 4; Aminopentyl-JNJ 7777120 BODIPY 630/650
n = 5; Aminohexyl-JNJ 7777120 BODIPY 630/650
n = 6; Aminoheptyl-JNJ 7777120 BODIPY 630/650
n = 7; Aminooctyl-JNJ 7777120 BODIPY 630/650

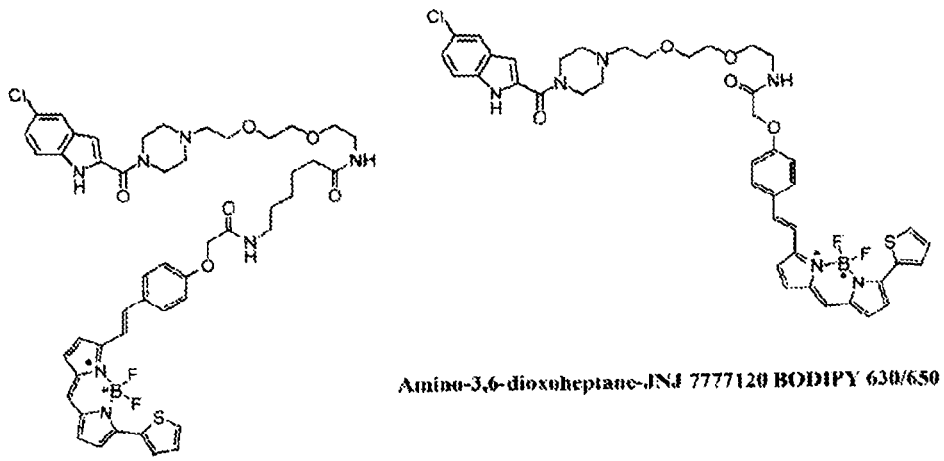

Amino-3,6-dioxoheptane-JNJ 7777120 BODIPY 630/650X

Amino-3,6-dioxoheptane-JNJ 7777120 BODIPY 630/650

(a red, b green, c yellow, green)

*(a red, b green, c red, yellow, green)*

HIGH CONTENT SCREENING

This application is a national stage application of International Application No. PCT/GB2005/003709 filed Sep. 26, 2005, which claims priority under 35 U.S.C. §119 to GB Application No. 0421285.8 filed Sep. 24, 2004, all of which are incorporated herein by reference.

The present invention relates to a high content screening (HCS) assay for rapidly screening one or more compounds to determine functional response/pharmacological properties thereof, a novel fluorescent agonist and the use thereof in the assay of the invention.

The objective of drug discovery is to find new substances that can cure, or at least contain important diseases. As such, a number of innovative approaches for achieving this goal have evolved and the science of high throughput screening (HTS) remains a key component of current methodologies. However, an emerging desire is to place less emphasis on the number of data points that can be produced, and to focus instead on the quality and extent of the information that can be obtained from an individual assay point.

The last sixty years have seen a dramatic increase in the number of drugs available to treat human diseases. The biochemical sites on which these drugs act can range from DNA to cell surface receptors and ion channels. Over 30% of currently marketed drugs act on cell surface G-protein-coupled receptors (GPCRs). The human gene encodes approximately 750 GPCRs, of which some 400 represent potential drug targets. Surprisingly, currently available drugs act at only 30 of these. Current approaches are hugely costly because of the need to run extensive chemical libraries through more than one assay. The ultimate aim is to develop a high throughput screen that provides all the necessary information for drug development in a single run.

The present invention effects a major step-change in the scope and capability of high throughput screening technology aimed at real-time single cell resolution. Our approach will allow for the first time the direct measurement of ligand-receptor binding and functional analysis of agonist and antagonist activity in the same cell. Furthermore, our approach will be equally applicable to addressing that same question in different membrane microdomains of an individual living cell.

There is a need to capitalise on recent advances in fluorescence technology to develop a completely new screening approach that will revolutionise the drug discovery process. Current approaches have until now involved the measurement of a single "read-out" of the activation of an individual receptor type in a recombinant cell system. Invariably the "readout" involves the measurement of a response that is a long way down the receptor-signalling pathway. A major problem with the existing screens for drugs acting on G-protein-coupled receptors is the large number of false-positives that arise because of drug interactions with components of the signalling system down-stream of the target receptor. In addition the assay varies considerably depending on whether the desired "hit" is an agonist (that binds to the receptor and elicits a functional response) or antagonist (that binds to the receptor and produces no response) for the target receptor.

In the broadest aspect of the invention there is provided a high content screening (HCS) assay for rapidly screening one or more compounds to determine functional response or pharmacological properties thereof, comprising:

i) priming a cell or cell material with a sensor for a biological response;
ii) contacting the compound(s) to be tested with the primed cell or cell material or contacting a cell or cell material which has been contacted with the compound(s) with the primed cell or cell material;
iii) simultaneously or subsequently contacting with a fluorescent agonist or a fluorescent neutral antagonist wherein the binding of the fluorescent agonist or antagonist and its associated biological response are detected or monitored in the same cell and are distinct allowing separate readout.

In one embodiment if binding of the (non fluorescent) compound(s) to be tested to the cell or cell material prevents the binding, and thereby prevents fluorescence, of the fluorescent agonist, and if the associated measurable biological response from the cell or cell material is maintained this indicates that the (non fluorescent) compound(s) is a potential agonist.

In an alternative embodiment, if binding of the (non-fluorescent) compound(s) to be tested to the cell or cell material prevents the binding, and thereby fluorescence, of the fluorescent agonist, and if the associated measurable biological response is absent this indicates that the (non-fluorescent) compound(s) is a potential antagonist.

In an alternative embodiment, if the (non-fluorescent) compound inhibits the binding of a fluorescent neutral antagonist to a defined receptor in a cell and if an associated decrease in biological response is observed, then the (non fluorescent) compound is a potential inverse agonist.

In an alternative embodiment, if the (non-fluorescent) compound inhibits the binding of a fluorescent neutral antagonist to a defined receptor in a cell and if no associated change in biological response is observed, then the (non fluorescent) compound is a potential neutral antagonist.

In an alternative embodiment, if the (non-fluorescent) compound inhibits the binding of a fluorescent neutral antagonist to a defined receptor in a cell and if an associated increase in biological response is observed, then the (non fluorescent) compound is a potential agonist.

Preferably, in an embodiment as hereinbefore defined in which the binding of a fluorescent neutral antagonist is to be inhibited, the assay is conducted in a constitutively active receptor system, for example in which a receptor is overexpressed, in which the cellular biological response will produce a stimulated response in the absence of any added agonist, antagonist or compound to be tested.

Preferably the HCS assay additionally includes readout of information relating to morphology of cells, gene transcription and toxicity.

Preferably the binding of the fluorescent agonist or fluorescent antagonist is detected with one particular fluorescent wavelength and its associated biological response is monitored in the same cell or cell material by a separate readout (e.g. different fluorescent, bioluminescent or chemiluminescent response).

The present invention establishes a revolutionary approach to the pharmacological analysis of novel ligands for a major family of drug targets, namely ligands for G-protein-coupled receptors (GPCR), ion channels, tyrosine kinase receptors and intracellular receptors including steroid receptors, PPARs (peroxisome proliferation activated receptor). The invention allows for the first time, the simultaneous measurement of ligand-receptor binding and the functional analysis of agonist and antagonist responses in living cells. This allows the identification of molecules that interact directly with the receptor and, at the same time, the determination of whether these molecules are agonists or antagonists of the target GPCR, ion channel, tyrosine kinase receptor or intracellular receptor. Furthermore, the invention allows this assessment to be made in ultra-high-throughput assays involving multiwell plates (for example 384 or 1456 wells) or in plasma membrane microdomains of a single living cell.

The present invention effects a major step-change in the scope and capability of high throughput screening technology aimed at real-time single cell resolution. The invention will allow for the first time the direct measurement of ligand-receptor binding and functional analysis of agonist and antagonist activity in the same cell. Furthermore, the present invention is equally applicable to addressing that same question in different membrane microdomains of an individual living cell.

Reference herein to a fluorescent agonist is to an agonist which maintains its binding affinity and functional activity on binding.

The assay of the invention determines whether the one or more compounds is a functional agonist or antagonist. In addition the assay determines whether the compound inhibits or binds ligand binding the primed cell or cell material, i.e. inhibits the binding of a fluorescent agonist or antagonist to a defined receptor.

Inhibition or binding may be direct or indirect, for example the one or more compounds may inhibit or bind a cell or cell material which interacts with the primed cell or cell material thereby eliciting or suppressing a response from the primed cell or cell material.

Preferably in the assay of the invention the detection of a sensor response indicates the one or more compounds is an agonist, and in contrast the suppression of an agonist-induced sensor response indicates the one or more compounds is an antagonist. Preferably in the assay of the invention the detection of a reduced basal sensor response indicates that one or more compounds is an inverse agonist. Preferably in the assay of the invention the detection of fluorescent agonist fluorescence indicates the one or more compounds does not inhibit binding of the cell or cell material by the fluorescent agonist and in contrast the suppression of fluorescent agonist fluorescence indicates the one or more compounds inhibits binding of the cell or cell material by the fluorescent agonist.

The assay of the invention may be homogeneous or non-homogeneous. It is well known to the skilled in the art that a homogeneous assay is conducted in a single phase, whilst a non-homogeneous assay requires isolation of assayed material from unbound reagent in order to achieve a clean readout or signal. In a particular advantage of the invention, fluorescent ligands of PCT/GB2004/001418 have affinity such that they bond permanently, semi-permanently or transiently, and may remain bound when unbound ligand is washed away, allowing the use of non-homogeneous assay if desired.

A sensor may be selected from a fluorescent, chemiluminescent or luminescent entity or a reporter gene or the like which is sensitive to a biological response to be investigated, for example a fluorescent or luminescent dye which is pH sensitive, voltage sensitive or the like.

A sensor for monitoring changes in membrane potential in response to agonist stimulation may be for example a fluorescent dye such as a thiocarbocyanine fluorescent dye (Invitrogen). A sensor for monitoring changes in intracellular free calcium may be for example a calcium sensitive fluorescent dye. A sensor for monitoring stimulation of intracellular signalling pathways may be for example a reporter gene (e.g. luciferase, secreted alkaline phosphatase, beta-lactamase and the like) under the control of specific response elements (e.g. CRE, SRE, NFAT, NFKB and the like). A sensor for monitoring changes in cyclic AMP and intracellular free calcium may be for example a chameleon fluorescent sensor which makes use of FRET-based signals.

Preferably a sensor is a fluorescent dye of different wavelength to the fluorescent agonist enabling spectral resolution of the sensor and agonist. For example the sensor may be a Calcium Ion Sensitive Fluorescent dye such as Fura-2, Fluo-3 or Fluo-4, (see www.probes.com). Fura-2 is a widely used UV-excitable fluorescent calcium indicator. Upon calcium binding, the fluorescent excitation maximum of the indicator undergoes a blue shift from 363 nm (Ca2+-free) to 335 nm (Ca2+-saturated), while the fluorescence emission maximum is relatively unchanged at ~510 nm. The indicator is typically excited at 340 nm and 380 nm respectively and the ratio of the fluorescent intensities corresponding to the two excitations is used in calculating the intracellular concentrations. Measurement of calcium concentration using this ratioing method avoids interference due to uneven dye distribution and photobleaching (Bright, G. R., et al, in Fluorescence Microscopy of Living Cells in Culture, Part B, (Methods in Cell Biology, Vol. 30), Academic Press (1989) p. 157). Fura-2 has been used in many cellular systems and applications, particularly in microscopic imaging.

A fluorescent agonist or fluorescent neutral antagonist in the assay of the invention may be any fluorescent agonist or antagonist whose pharmacological properties are known, and is preferably selected from fluorescent agonists or antagonists disclosed in PCT/GB2004/001418, the contents of which are incorporated herein by reference.

In PCT/GB2004/001418 we disclose fluorescent ligands (agonists and antagonists) for a number of G-protein-coupled receptors. Using confocal microscopy we have been able to show that these bind selectivity to membrane receptors in single living cells (FIG. 2). Furthermore, using fluorescence correlation spectroscopy we have been able to evaluate quantitatively the characteristics of this binding in small microdomains of the membrane of single living cells (FIG. 2).

More preferably a fluorescent agonist or fluorescent neutral antagonist for use in the assay of the invention is identified by the methodology of PCT/GB2004/001418 most preferably by a method for determining the functional response or pharmacological properties of a fluorescent ligand, comprising:

a) priming a cell or cell material with a sensor for a biological response;

b) subsequently contacting with a fluorescent ligand wherein the binding of the fluorescent ligand and its associated biological response are detected or monitored in the same cell and are distinct allowing separate readout, and wherein if binding, and thereby fluorescence, of the fluorescent ligand is detected, and if the associated measurable biological response from the cell or cell material is maintained this indicates that the fluorescent ligand is a potential agonist, and if binding, and thereby fluorescence, of the fluorescent ligand is detected but the associated measurable biological response from the cell or the cell material is reduced or is absent, this indicates that the fluorescent ligand is a potential neutral antagonist or inverse agonist.

Preferably a fluorescent ligand comprises one or a plurality of ligand moieties linked to one or a plurality of fluorescent moieties via a linker at a linking site which maintains ligand activity.

Preferably the ligand moiety is a moiety of a ligand for a GPCR, an ion channel, a tyrosine kinase receptor or intracellular receptor such as a steroid receptor, or a PPAR.

Preferably a ligand moiety for a GPCR in a fluorescent ligand of the invention is selected from any compound which is active as an agonist for an adenosine receptor, a beta-adrenoceptor, a muscarinic receptor, a histamine receptor, an opiate receptor, a cannabinoid receptor, a chemokine receptor, an alpha-adrenoceptor, a GABA receptor, a prostanoid receptor, a 5-HT (serotonin) receptor, an excitatory aminoacid receptor (eg glutamate), a dopamine receptor, a protease-activating receptor, a neurokinin receptor, an angiotensin receptor, an oxytocin receptor, a leukotriene receptor, a nucleotide receptor (purines and pyrimidines), a calcium-sensing receptor, a thyroid-stimulating hormone receptor, a neurotensin receptor, a vasopressin receptor, an olfactory receptor, a nucleobase receptor (ag adenosine), a lysophosphatidic acid receptor, a sphingolipid receptor, a tyramine receptor (trace amines), a free-fatty acid receptor and a cyclic nucleotide receptor and the like, preferably for a GPCR receptor for example an adenosine receptor agonist or a beta-adrenoceptor agonist.

A fluorescent moiety may be any moiety recited in PCT/GB2004/001418. Preferably a fluorescent moiety is any red, green, near ir, blue or the like absorbing dyes or other class of dye. Suitably a fluorescent moiety is selected from dyes in particular including fluorescein, fluorescein derivatives including FITC, and fluorescein-like molecules such as Oregon Green™ and its derivatives, Texas red™, 7-nitrobenz-2-oxa-1,3-diazole (NBD) and derivatives thereof, coumarin and derivatives, naphthalene including derivatives of dansyl chloride or its analogues or derivatives, Cascade Blue™, EvoBlue and fluorescent derivatives thereof, pyrenes and pyridyloxazole derivatives, the cyanine dyes, the dyomics (DY dyes and ATTO dyes) and fluorescent derivatives thereof, the Alexafluor dyes and derivatives, BDI dyes including the commercially available Bodipy™ dyes, erythosin, eosin, pyrenes, anthracenes, acridines, fluorescent phycobiliproteins and their conjugates and fluoresceinated microbeads, Rhodamine and fluorescent derivatives thereof including Rhodamine Green™ including the tetramethylrhodamines, X-thodamines and Texas Red derivatives, and Rhodol Green™, coupled to amine groups using the isocyanate, succinimidyl ester or dichlorotriazinyl-reactive groups and other red, blue or green absorbing fluorescent dyes in particular red absorbing dyes as reviewed in Buschmann V et al, Bioconjugate Chemistry (2002), ASAP article.

More preferably a fluorescent moiety is selected from fluorescein derivatives and fluorescein-like molecules such as Oregon Green™ and its derivatives, Texas red™, 7-nitrobenz-2-oxa-1,3-diazole (NBD) and derivatives thereof, coumarin and derivatives, naphthalene including derivatives of dansyl chloride or its analogues or derivatives, Cascade Blue™, EvoBlue and fluorescent derivatives thereof, pyrenes and pyridyloxazole derivatives, the cyanine dyes, the dionics (DY dyes and ATTO dyes) and fluorescent derivatives thereof, the Alexafluor dyes and derivatives, BDI dyes including the commercially available Bodipy™ dyes, erythosin, eosin, FITC, pyrenes, anthracenes, acridines, fluorescent phycobiliproteins and their conjugates and fluoresceinated microbeads, Rhodamine derivatives thereof including Rhodamine Green™ including the tetramethylrhodamines, X-rhodamines and Texas Red derivatives, and Rhodol Green™.

More preferably a fluorescent moiety comprises fluorescein, Texas Red™, Cy5.5 or Cy5 or analogues thereof, BODIPY™ 630/650 and analogues thereof in particular BODIPY™ 630/650X, DY-630, DY-640, DY-650 or DY-655 or analogues thereof, ATTO 655 or ATTO 680 or analogues thereof, EvoBlue 30 or analogues thereof, Alexa 647 or analogues thereof.

Suitably a fluorescent moiety is derived from any of the above commercially available fluorophores, comprising or modified to comprise a reactive group facilitating linking to a ligand.

Preferable the fluorescent agonist or antagonist of the invention is tailored by the site of linking of fluorescent and ligand moieties, the means of linking, ie nature and length of linker, and the stoichiometry thereof, ie 1:1, 2:1, 1:2 etc, whereby binding and function of the agonist or antagonist are retained in the fluorescent agonist or antagonist, and pharmacological properties are known whereby modulation of binding and function are known.

Preferably a fluorescent agonist or antagonist is of the formula

which may be present as a racemate or as one of its optically active isomers wherein Fl is selected from any fluorophore as hereinbefore defined and wherein ligand-linker Lig $J_L$ L $J_T$ is selected from the formulae Lig.a, Lig.b, Lig.c, Lig.d and Lig.h wherein:

Lig.a comprises linking functionality $J_L$ which is amine, and is of the formula, in either of the following forms given:

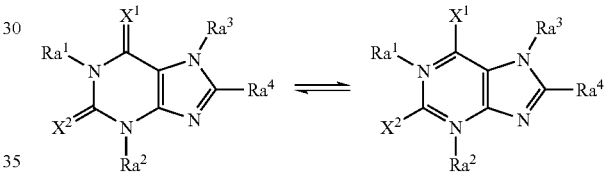

wherein $Ra^4$ comprises linking functionality $J_L$ and $J_T$ which is amine;
$X^1$ and $X^2$ are each O;
$R.a^3$ is H;
each of $R.a^1$ and $R.a^2$ is n-propyl;
$R.a^4$ is p- substituted phenyl wherein the substituent is heteroalkyl amide amine; and includes L which is a single bond or is $C_{1-50}$ alkyl, preferably $C_{1-24}$ alkyl, more preferably $C_{1-12}$ alkyl optionally substituted by C, alkyl and including the formula —$(CH_2)_n$— where n is 3 to 8, optionally including one or more heteroatoms —O—;

Lig.b comprises linking functionality $J_L$ which is amine, and is

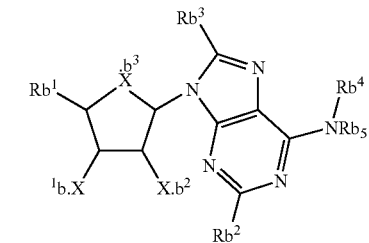

wherein ring substituents $X.b^1$ and $X.b^2$ are each OH;
ring heteroatom $X.b^3$ is —O—;
$Rb^1$ is CONHEt or $CH_2OH$;
and each of $R.b^2$ and $R.b^3$ is H;
$Rb^4$ is H;

Rb⁵ comprises linking functionality $J_T$ which is amino, and linker L.b selected from saturated $C_{1-12}$ aliphatic and $C_{6-24}$ aromatic, optionally substituted by one or more $C_1$ alkyl and optionally including one or more heteroatoms O or cyclic groups;

Lig.c comprises linking functionality $J_L$ which is amine and is

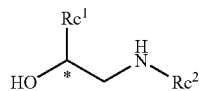

as a racemate or as one of its optically active isomers wherein * indicates an optically active centre, Rc¹ is m-, p- dihydroxyphenyl; and Rc² comprises linking functionality $J_T$ which is amine, and linker L.c which is selected from $C_{1-12}$ straight chain alkyl, $C_{6-12}$ cycloalkyl or aryl and combinations thereof optionally comprising one or more heteroatoms O and optionally substituted by $C_1$ aliphatic;

or Lig.d comprises a linking functionality $J_L$ which is amine and is

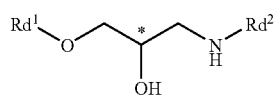

as a racemate or as one of its optically active isomers wherein * indicates an optically active centre, Rd¹ is selected from the structures

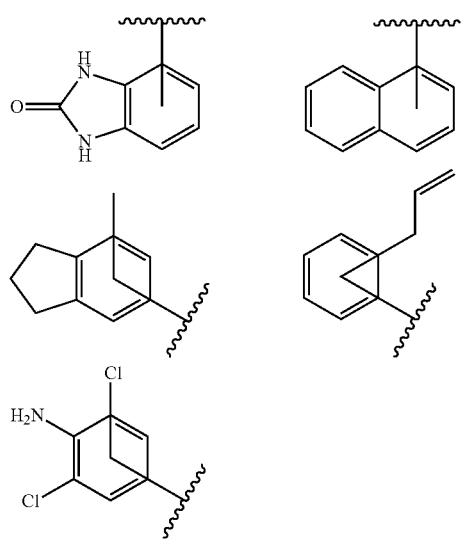

and a substituted $C^{1-20}$ spiro aromatic ring system comprising a single aromatic ring and a heteroaryl and optionally halo substituted; and Rd² comprises linking functionality $J_T$ which is amine, and linker L.d which is selected from $C_{1-12}$ straight chain alkyl, $C_{6-12}$ cycloalkyl or aryl and combinations thereof optionally comprising one or more heteroatoms O and optionally substituted by $C_1$ aliphatic; or Rd² is $C_{1-6}$ straight chain alkyl including ether O and substituted by $C_{6-10}$ aryl which is OH and oxo substituted and comprises linker L.d as hereinbefore defined, or Lig.h comprises a linking functionality $J_L$ which is amine and is

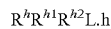

wherein $R^h$ is selected from $C_{1-20}$ hydrocarbyl including one or more heteroary, aryl, cycloatyl, heterocyclyl optionally together with or substituted by or including one or more heteroatoms or halo such as O, N, Cl and the like $R^{h1}$ is selected from $C_{0-4}$ alkyl $R^{h2}$ is a single bond or is selected from —$NR^{h3}$—, —$H^1C(=H^2)NH$— or

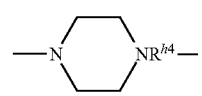

wherein $H^1$ is $NR^{h3}$ or O and $H^2$ is selected from —HN, —O and —S and wherein $R^{h3}$ is selected from H, $CH_{1-3}$ alkyl such as $CH_3$ and CN and $R^{h4}$ is selected from a single bond, $C_{1-6}$ ether or etheramide L.h comprises linking functionality $J_T$ which is amino, and linker linker L which is selected from $C_{1-12}$ straight chain alkyl, $C_{6-12}$ cycloalkyl or aryl and combinations thereof optionally comprising one or more heteroatoms O and optionally substituted by $C_1$ aliphatic.

Preferably R.a⁴, R.b⁵ or R.c² or R.d² or L.h comprises linking functionality $J_T$ which is amino, and linker L.a, L.b, L.c. L.d or L.h selected from $(CH_2)m$ wherein m is in the range 2 to 12, preferably 3 to 8 for example 3, 4, 5, 6, 7 or 8 optionally including one or more substituents $C_1$, or $J_L$ L $J_T$ is mono or polyethylene glycol diamine, or L.a is a single bond; or R.c² or R.d² comprises linking functionality $J_T$ which is amino, and linker L.c or L.d selected from $C(CH_3)_2CH_2Ph$ and mono amino menthane or the structure

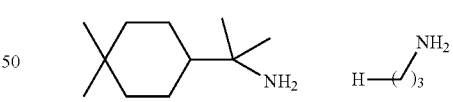

or Rd² comprises the following OH substituted aryl structure wherein linking functionality $J_L$ is shown as amine, Ld is as hereinabove defined and includes $J_T$ which is amine:

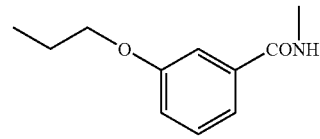

or $R^h$ is selected from the following structures

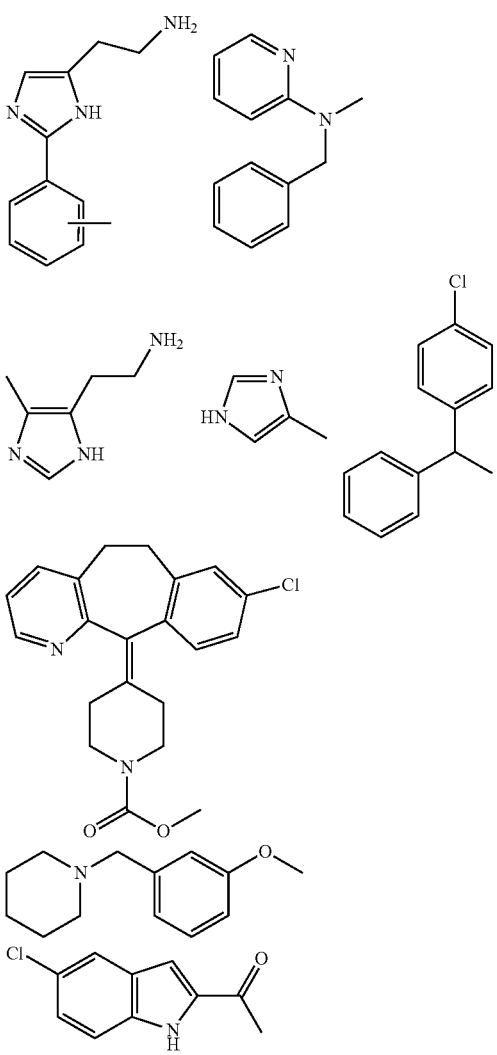

Or $R^{h2}$ is selected from $HNC(=NR^{h3})NH$, $OCH_2C(=O)NH$, $SC(=NH)NH$,

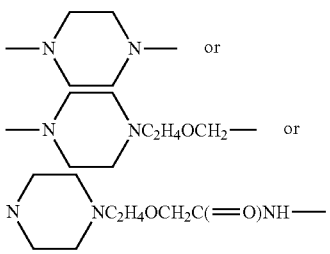

More preferably the fluorescent agonist or neutral antagonist of the invention is selected from compounds as listed in FIG. 1 annexed hereto.

The assay of the invention may be homogeneous or non-homogeneous. In a particular advantage of the invention, fluorescent ligands of PCT/GB2004/001418 have affinity such that they bond permanently, semi-permanently or transiently, and may remain bound or be washed away when unbound ligand is washed away.

A cell or cell material may comprise cells, cell extracts, cell homogenates, purified or reconstituted proteins, recombinant proteins or synthesised proteins and the like, and includes a target for the compound to be tested. A cell or cell material may be derived from plants, animals, fungi, protists, bacteria, archae or cell lines derived from such organisms. Animal or plant cells used to prepare the cell or cell material may be healthy or disfunctional and are optionally used in the diagnosis of a disease such as leukaemia or cancer. In a preferred embodiment of the invention the cell or cell material comprises mammalian cells, extracts and homogenates thereof.

Preferably a cell or cell material comprises live cell material, more preferably including individual cells or sub cell compartments, most preferably comprising GPCRs, intracellular enzymes or drug transporters in living cells, membrane containing these proteins, solubilised receptors, enzymes or drug transporters or GPCR arrays. A cell or cell material may be obtained in known manner by culturing cells or by expressing proteins in cells.

In a preferred embodiment the cell or cell material is a cell expressing a GPCR, enzyme or drug transporter. GPCR's are possibly the single most important class of targets for current and prospective drug therapies.

More preferably the cell or cell material comprises GPCR receptors selected from adenosine $A_1$-, $A_{2A}$-, $A_{2B}$- and $A_3$-receptors, $\beta_1$, $\beta_2$- and $\beta_3$- adrenoceptors, or comprises inhibitors of intracellular enzymes such as cyclic nucleotide pliosphodiesterases, most preferably CHO cells expressing human adenosine $A_1$-receptor or beta-adrenoceptor or an inhibitor of an intracellular enzyme such as an inhibitor of intracellular phosphodiesterases.

Receptors may be provided in membrane samples or in acutely dispersed cell samples, for example endogenous receptors such as $A_1$-AR in acutely dispersed cells. The adenosine receptor binding site is located deep within the pocket of the receptor, whereby a fluorescent agonist as hereinbefore defined is a preferred fluorescent agonist. Whilst there is considerable freedom in modifying a ligand and retaining antagonist binding activity, it is harder to retain agonist activating activity, ie activating the receptors functions on binding, and the fluorescent agonists as hereinbefore defined are particularly effective in this respect.

The method for drug transport of a substrate of a drug transporter would be to follow the uptake of the fluorescent agonist and thereby the compound to be tested into the cell cytosol (if the transporter moves the drug into cells) or after loading the cells with substrate to follow the disappearance of the agonist or compound from the cells and its appearance in the extracellular medium (if the transporter moves the drug out of the cells—for example in the case that the transporter is an ATP-driven pump). Preferably the method comprises monitoring transport of a drug into a cell via an equilibrium transporter that moves the compound into the cell—then applying an inhibitor of this first equilibrium transporter, and monitoring the export of the drug from the cells via an ATP-driven pump transporter.

The method of inhibition of a drug transporter may be monitored by detecting binding to the transporter on the cell surface.

The assay of the invention may employ any suitable optical technique to determine or indicate binding and function. Preferably the assay includes detecting a change in the intensity, excitation or emission wavelength distribution of fluorescence (single and multi photon), fluorescence lifetime, fluorescence polarisation or a combination thereof or the like. The optical response is detected by known means such as cameras, film, laser-scanning devices, fluorometers, photodiodes, quantum counters, microplate, microscopes, fluorescent microscopes such as epifluorescence or confocal, cytometers, readers and the like, preferably CSLM, confocal plate readers, fluorescence polarisation plate readers or FCS. Where the sample is examined using a flow cytometer, examination of the sample optionally includes sorting components of the sample according to their fluorescence response. Preferred techniques include confocal microscopy (CM) and fluorescence correlation microscopy (FCS).

An assay according to the invention may be in vitro or in vivo.

In a particular advantage the assay of the invention is suitable for use in combination with FCS enabling the study of ligand-receptor binding at the single molecule level. Because of the nature of the events being monitored FCS is ideal for the study of thermodynamic and kinetic features of molecular interactions in solution. Another particular advantage of the invention is that the FCS approach can be adapted to monitor ligand-receptor binding at the single molecule level using photon counting fluorescence intensity measurements.

With fluorescent agonists showing low background fluorescence it is not necessary to remove unbound agonist or compound to be tested by washing before performing either confocal microscopy or FCS. It is therefore possible to measure fluorescence with time, in both time and concentration dependent manner.

Confocal microscopy (CSLM) allows visualisation of a section through a cell showing concentration of fluorophore at the cell edges indicating membrane receptors binding. Visualisation is of a particular plane of focus such that a "slice" through an individual cell may be observed, as known in the art. Different coloured channels may be selected to visualise different fluorophore types.

FCS is a non-invasive technique which analyses the diffusion characteristics of fluorescent species through a very small excitation volume ($<10^{-15}$l) by statistically analysing the pattern of their photon emissions. Thus fast-diffusing free ligand can be distinguished from slowly-diffusing receptor-bound ligand and quantified simultaneously when the volume is localised to the cell membrane. Preferably the method incorporating FCS comprises measuring fluctuations in fluorescence intensity in a confocal volume of $<10^{-15}$l. Statistical analysis of these fluctuations gives information about the speed of diffusion (i.e. mass) and concentration of the fluorescent molecules present. Thus free ligand (fast diffusing) and bound ligand (slow diffusing) can be quantified simultaneously on a single cell.

FCS (fluorescence correlation spectroscopy) correlates fluctuations in fluorescence emission of particles to parameters such as particle mass and concentration for the study of molecular interactions in solution. FCS essentially monitors spontaneous fluorescence intensity fluctuations of fluorescently tagged molecules in a microscopic detection volume ($10^{-15}$l) through analysis by a tightly focused laser beam.

These fluctuations provide information on the rate of diffusion or diffusion time of a particle which is directly dependent on the mass of the given molecule. When small and therefore rapidly diffusing molecules pass through the path of the laser they produce rapidly fluctuating fluorescence intensity patterns, whereas when larger molecules pass through the beam they produce bursts of fluorescence that are more sustained. Consequently the increase in the mass of a biomolecule, eg as a result of ligand binding, is detected as an increase in the diffusion time of the resultant biomolecule.

Fluorescence microscopy may be used to localise receptors at single cell or sub cellular level with sensitivity and speed. In this way high affinity fluorescent ligands used in the assay of the invention could help to elucidate molecular characteristics of GPCR receptor subtypes, such as adenosine and the like receptors, their regional distribution and cellular localisation.

The assay of the invention may employ the use of a fluorescent target for the fluorescent agonist, for example, a Green Fluorescent Protein-tagged receptor, intracellular enzyme or drug transporter. In this case the spectral characteristics of the fluorescent agonist are chosen to allow separate detection of the location of both the fluorescent agonist and the fluorescent receptor, intracellular enzyme or drug transporter. Cross-correlation fluorescence correlation spectroscopy or fluorescence intensity measurements will then allow the quantitative analysis of agonist-receptor, agonist-enzyme, agonist-drug transporter or drug transport interactions in a single measurement. This is distinct from prior art methods involving GFP-protein translocation assays and assays involving fluorescence energy transfer (FRET).

In each case, the spectral characteristics of the one or more compounds and the fluorescent agonist are selected to allow optimum two-colour cross-correlation fluorescence correlation spectroscopy or confocal microscopy which may be single or multiphoton.

In a further aspect of the invention there is provided a novel fluorescent agonist or fluorescent neutral antagonist as hereinbefore defined., Preferably a novel fluorescent agonist or fluorescent neutral antagonist is a compound of formula Lig.h Fl wherein Lig.h and Fl are as hereinbefore defined Preferably a novel fluorescent agonist or fluorescent neutral antagonist is selected from compounds as listed in FIG. 1 annexed hereto or from the formula

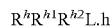

wherein $R^h$ is selected from $C_{1-20}$ hydrocarbyl including one or more heteroaty, aryl, cycloaryl, heterocyclyl optionally together with or substituted by or including one or more heteroatoms or halo such as O, N, Cl and the like $R^{h1}$ is selected from $C_{0-4}$ alkyl $R^{h2}$ is a single bond or is selected from —NR$^{h3}$—, —H$^1$C(=H$^2$)NH— or

wherein $H^1$ is NR$^{h3}$ or O and $H^2$ is selected from —HN, —O and —S and wherein $R^{h3}$ is selected from H, $C_{1-3}$ alkyl such as CH$_3$ and CN and $R^{h4}$ is selected from a single bond, $C_{1-6}$ ether or etheramide L.h comprises linking functionality $J_T$ which is amino, and linker L which is selected from $C_{1-12}$ straight chain alkyl, $C_{6-12}$ cycloalkyl or aryl and combinations thereof optionally comprising one or more heteroatoms O and optionally substituted by $C_1$ aliphatic.

Preferably $R^h$ is selected from the following structures

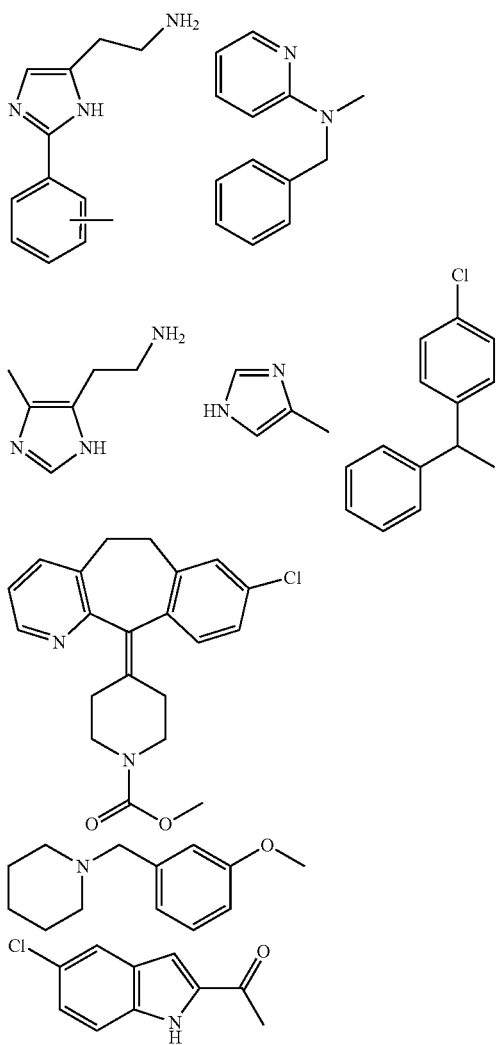

Or $R^{h2}$ is selected from HNC(=$NR^{h3}$)NH, $OCH_2C$(=O)NH, SC(=NH)NH,

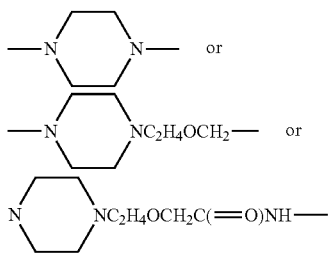

In a further aspect of the invention there is provided the use of a novel or known fluorescent agonist or fluorescent neutral antagonist, as hereinbefore defined or as defined in PCT/GB2004/001418 or other publications, the contents of which are incorporated herein by reference, in the assay of the invention.

In a further aspect of the invention there is provided a ligand identified by the HCS assay of the invention for drug targets selected from G-protein-coupled receptors (GPCRs), ion channels, tyrosine kinase receptors and intracellular receptors including steroid receptors, PPARs.

The invention is now illustrated in non-limiting manner with reference to the following figures and examples.

FIG. 1 shows fluorescent ligands of the invention

FIG. 2 shows binding of red fluorescent (a) antagonist or (b) agonist to CHO cells transfected with the human adenosine $A_1$-receptor. (c) Diffusion of fluorescent molecules through the FCS confocal volume. (d) FCS fluctuations due to free ligand or receptor-bound ligand (large fluctuations in red) diffusing through the confocal volume when it is placed on the cell membrane or in the media above the cells confocal volume (red signal 20 micron above cell, blue signal upper membrane).

Figure 3:
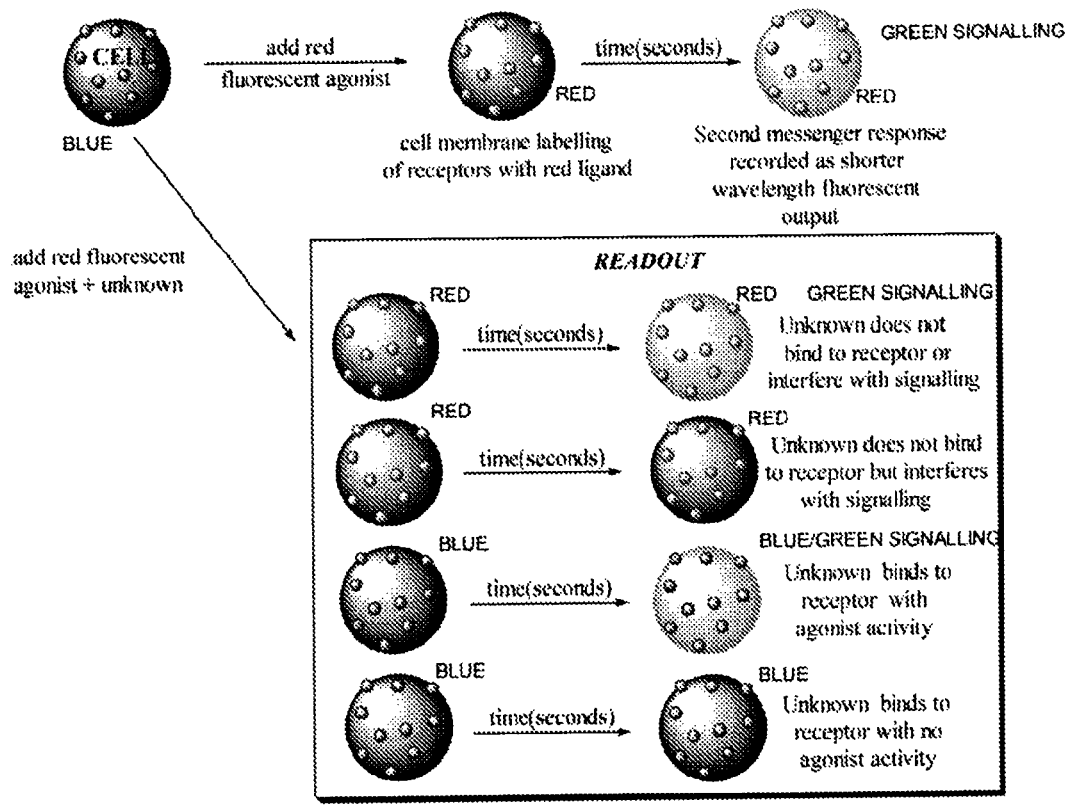

FIG. 3 shows schematic representation of the pharmacological assay of the invention employing fluorescent ligands and novel engineered cell lines expressing a GPCR target receptor with an in-built calcium sensor motif.

Figure 4A:
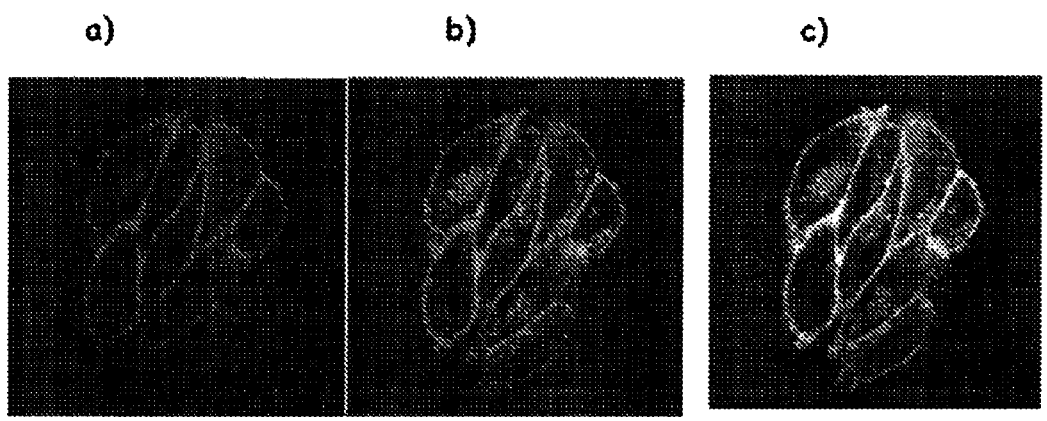
Figure 4B:
Figure 5A:
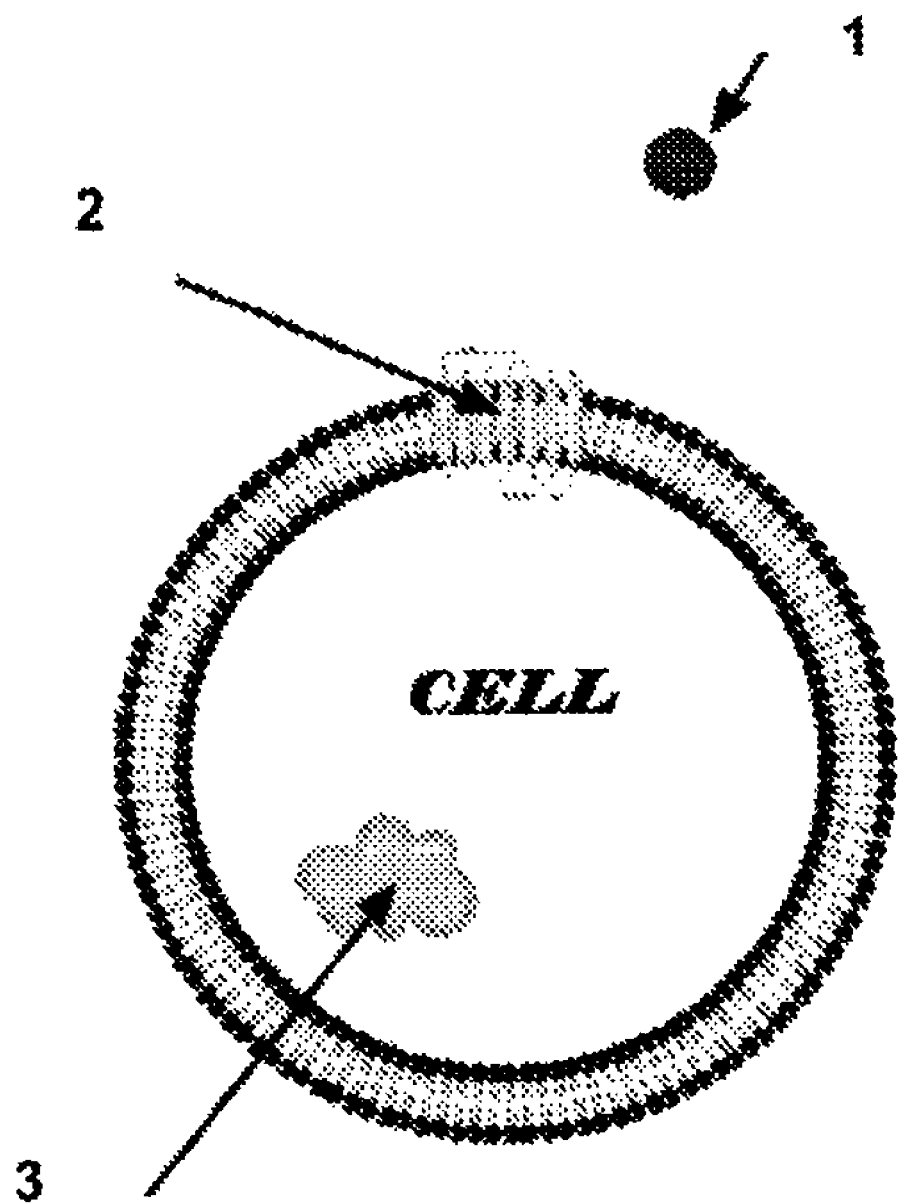
Figure 5B:
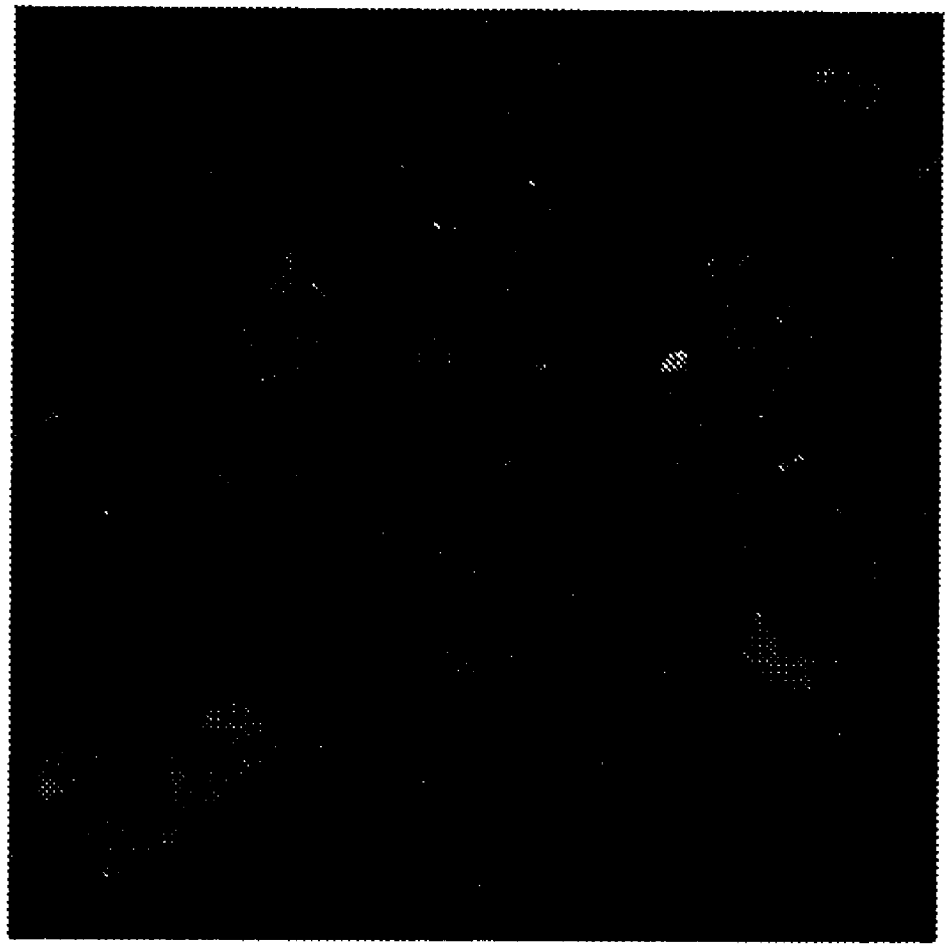
Figure 5C:
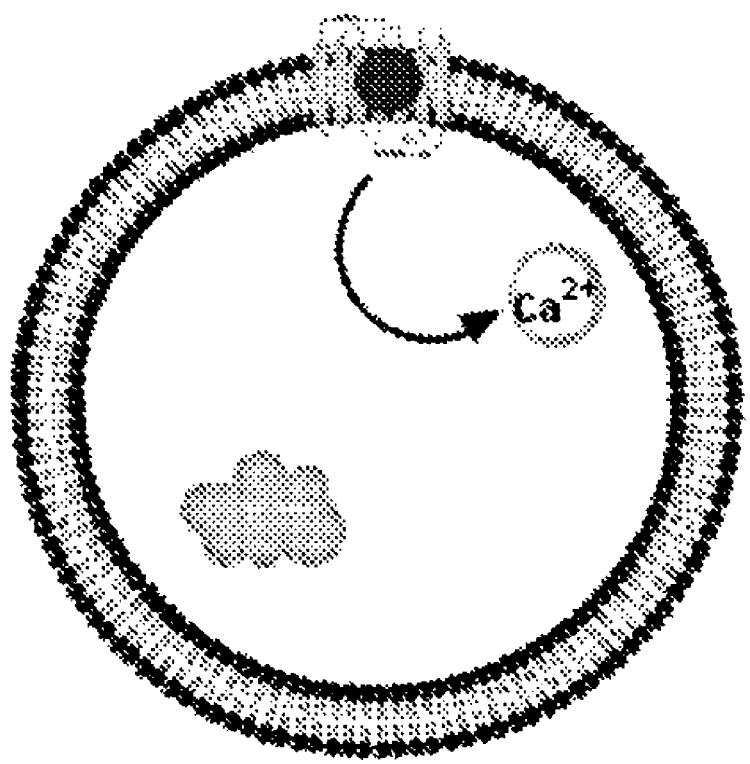
Figure 5D:
Figure 5E:
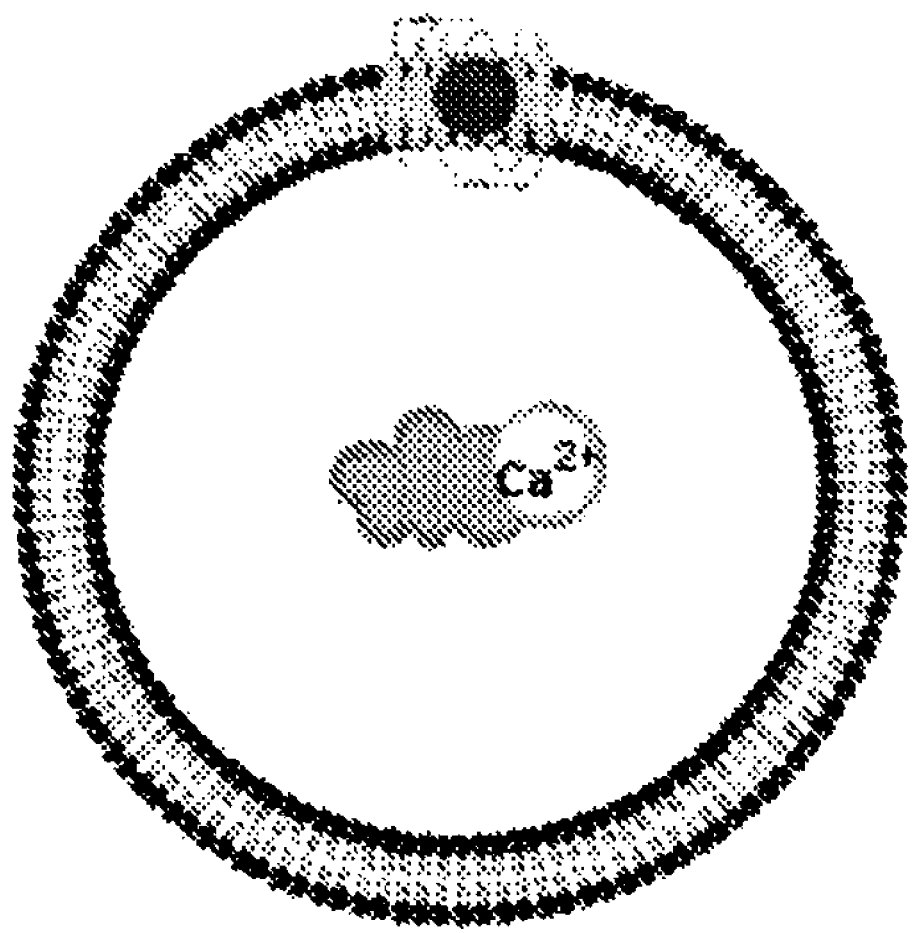
Figure 5F:

The FIG. 3 schematic illustrates the potential readouts that could be obtained using a red fluorescent agonist, a shorter wavelength second messenger and a non fluorescent unknown compound;

FIG. 4A shows images taken from confocal microscopy imaging (50 nM, 15') of a) fluorescence derived from ligand binding of a fluorescent ligand of the invention, BODIPY-XAC, to CHO cells observed at the red channel, b) fluorescence derived from green fluorescent protein expressed by CHO cells(A1-R-Topaz) indicating receptor locations observed via the green channel and c) overlaid images from a) and b) showing overlap of fluorescence and therefore confirming ligand binding is specific to receptors. FIG. 4B shows the same for binding of fluorescent ligand ABEA- BY630 (100 nM, 30');

In FIG. 5A the cell is charged with a second messenger (e.g. Calcium) sensitive fluorescent dye (3) and the, red fluorescent ligand (1) is introduced. FIG. 5B shows that at the zero time point, there is no membrane, binding of the ligand to the receptor (2) and no visible second messenger response. In FIG. 5C the red fluorescent ligand (1) binds to the receptor (2) and if it is an agonist, stimulates production of the detectable second messenger. In FIG. 5D the membrane binding of the fluorescent ligand (1) is visible at 500 seconds and the second messenger response is small. In FIG. 5E the second messenger interacts with the fluorescent dye (3) to produce an increase in fluorescence output. In FIG. 5F there is clear and widespread membrane labeling at 620 seconds from the binding of the red fluorescent ligand (1) with its target receptor (2), accompanied by strong intracellular fluorescent oscillations produced by the increase in concentration of the second messenger and its interaction with the sensing dye (3).

EXAMPLE 1

A fluorescent agonist for use in the assay of the invention is designed to be an agonist in transfected cells with a defined level of target GPCR expression. This allows antagonists to be identified by their ability to inhibit both the binding of the fluorescent agonist and the subsequent functional response (FIG. 3).

A full agonist is identified by its ability to inhibit binding to the GPCR and to maintain the functional response as the fluorescent agonist is displaced from the receptors on the cell surface (FIG. 3).

The sensor is Fura-2, Fluo-3 or Fluo-4, all Calcium Ion Sensitive Fluorescent dyes (see www.probes.com) which are preloaded into the transfected cells.

Functional responses is initially monitored using fluorescent probes for particular second messengers (e.g. cAMP and $Ca^{2+}$), The fluorescent agonist for use in the assay of the invention is designed with a fluorophore that is excited at 633 nm in order to make sure there is easy detection of the two signals without interference (the functional responses will generally utilise the 488 nm laser line). Measurement of both binding and function for high-throughput assays is made with a confocal multi-well plate reader. Measurement of binding and function in microdomains of a single living cell is made using a confocal microscope and a fluorescence-correlation spectroscopy (FCS) detection head.

An aim is to synergise the two technologies. in order to facilitate this we will engineer cell lines to ensure that the probe for the second messenger response is in close proximity to the receptor on the cell surface. This will be achieved by genetically engineering the GPCR to attach the second messenger detector to the C-terminus of the receptor (FIG. 3).

EXAMPLE 2

The following compounds were synthesised or modelled and binding affinity studied in PCT/GB2004/001418:

Example A1/B 1/C1 Adenosine Receptors Antagonists

XAC-BODIPY 630/650 (1)

Example A2/B2 Adenosine Receptor Agonists

Adenosine-BODIPY 630/650 (2)
NECA-BODIPY 630/650 (3) (ABEA-BODIPY 630)
APEA-BODIPY 630/650 (3a)
ABIPEA-BODIPY 630/650 (3b)

Example A3/B3 Beta-adrenoreceptor Agonists

Salmeterol-BODIPY 630/650 (4)
Clenbuterol-BODIPY 630/650 (9)

Example A4/B4 Beta-Adrenoreceptor Antagonists

CGP12177-BODIPY 630/650 (5)
Propranolol-BODIPY 630/650 (6)
IC1118551-BODIPY 630/650 (7)
Alprenolol-BODIPY 630/650(8)

Example A5/B5 Inhibitors of Cyclic Nucleotide Phosphodiesterases

XAC-BODIPY 630/650 (1)

In Example B2 BY630-ABEA was identified as a fluorescent agonist ligand for the human $A_1$-AR and is suitable for use as a fluorescent ligand in the assay of the invention.

Example B2-Binding of NECA Based Fluorescent $A_1$-Receptor Agonists

2. BY630-ABEA (3)

Functional studies were performed in CHO-K1 cells expressing both the human $A_1$-AR and a c-fos-pGL3 reporter vector (CHO-A1fos cells). Cells were incubated for 24 h in serum-free DMEM/F-12 media, then stimulated with agonist for 5 h, in some cases following 30 min incubation with 8-cyclopentyl-1,3-dipropylxanthine (DPCPX). Luciferase expression was quantified using a Luclite® kit according to manufacturer's instructions. Live cell confocal imaging was carried out on CHO-A1 cells or CHO cells expressing the $A_1$-AR tagged on the C-terminus with a green fluorescent protein (CHO-A1Tpz).

In CHO-A1fos cells, both BY630-ABEA and the $A_1$-AR agonist $N^6$-cyclopentyl adenosine (CPA) stimulated luciferase expression in a dose-dependent manner ($pEC_{50}$'S of 7.01±0.04 (n=6) and 6.76±0.18 (n=5) for CPA and BY630-ABEA, respectively, mean+s.e.mean). Stimulation was mediated by the $A_1$-AR receptor, since the concentration response curves were shifted to the right in a competitive manner by 10 nM DPCPX, yielding $pK_d$ values of 8.72±0.03 and 9.05±0.10 vs. CPA and BY630-ABEA, respectively (n=3). A higher dose of DPCPX (100 nM), gave a $pK_d$ of 8.62±0.02 for CPA stimulation, but completely blocked the response to BY630-ABEA (n=3). For receptor visualisation, CHO-$A_1$ cells were incubated with 100 nM BY630-ABEA for up to 60 min Binding of ligand to the membrane was detectable after 5 min, and was substantial after 30 min (n=3). Binding was to the $A_1$-AR, since it was substantially reduced by preincubation with DPCPX (1 μM, 30 min). In addition, experiments in CHO-A1Tpz cells, showed co-localisation of ligand fluorescence at the membrane with that from the fluorescently tagged $A_1$-AR.

Results are shown in FIG. 4 which shows images taken from confocal microscopy imaging of a) fluorescence derived from ligand binding of a fluorescent ligand of the invention to CHO cells observed at the red channel, b) fluorescence derived from green fluorescent protein expressed by CHO cells indicating receptor locations observed via the green channel and c) overlaid images from a) and b) showing overlap of fluorescence and therefore confirming ligand binding is specific to receptors.

In conclusion, we have succeeded in synthesising a novel fluorescent agonist ligand for the human $A_1$-AR. This ligand will be useful in monitoring the localisation of the endogenous $A_1$-AR receptor in both acutely dispersed cells and cell lines.

The invention claimed is:

1. A high content screening (HCS) assay for rapidly screening one or more compounds to determine functional response or pharmacological properties thereof, comprising:
    i) priming a cell or cell material expressing a GPCR with a sensor for a biological response;
    ii) contacting the compound(s) to be tested with the primed cell or cell material or contacting a cell or cell material which has been contacted with the compound(s) with the primed cell or cell material, whereby the compound(s) is to be pharmacologically analyzed as a ligand for GPCRs;
    iii) simultaneously or subsequently contacting with a fluorescent agonist or a fluorescent antagonist whose pharmacological properties are known, selected from a GPCR ligand moiety linked to a fluorescent moiety via a linker at a linking site which maintains ligand activity, the fluorescent moiety comprising a red absorbing BDI dye wherein the binding of the fluorescent agonist or antagonist and its associated biological response are detected or monitored in the same cell and are distinct allowing separate readout, wherein the fluorescent agonist or fluorescent antagonist is a novel fluorescent histamine receptor agonist or fluorescent histamine receptor antagonist selected from red absorbing BODIPY derivatives of GPCR ligands wherein the ligand is selected from the formula

wherein $R^h$ is selected from $C_{1-20}$ hydrocarbyl including one or more heteroaryl, aryl, cycloaryl, heterocyclyl optionally together with or substituted by or including one or more heteroatoms or halo such as O, N, Cl $R^{h1}$ is selected from $C_{0-4}$ alkyl $R^{h2}$ is a single bond or is selected from —$NR^{h3}$—, —$H^1C(=H^2)NH$— or

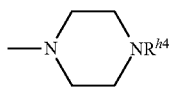

wherein $H^1$ is $NR^{h3}$ or O or S and $H^2$ is selected from —HN, —O and —S and wherein $R^{h3}$ is selected from H, $C_{1-3}$ alkyl such as $CH_3$ and CN and $R^{h4}$ is selected from a single bond, $C_{1-6}$ ether or etheramide Or $R^{h2}$ is selected from $HNC(=NR^{h3})NH$, $OCH_2C(=O)NH$, $SC(=NH)NH$,

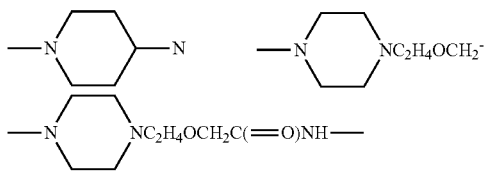

L.h comprises linking functionality $J_T$ which is amino, and linker linker L which is selected from $C_{1-12}$ straight chain alkyl, $C_{6-12}$ cycloalkyl or aryl and combinations thereof optionally comprising one or more heteroatoms O and optionally substituted by $C_1$ aliphatic.

2. A HCS assay as claimed in claim 1 wherein if binding of the test compound(s) to the cell or cell material prevents the binding, and thereby prevents fluorescence, of the fluorescent agonist, and if the associated measurable biological response from the cell or cell material is maintained this indicates that the test compound(s) is a potential agonist.

3. A HCS assay as claimed in claim 1 wherein if binding of the test compound(s) to the cell or cell material prevents the binding, and thereby fluorescence, of the fluorescent agonist, and if the associated measurable biological response is absent this indicates that the test compound(s) is a potential antagonist.

4. A HCS assay as claimed in claim 1 wherein if the test compound inhibits the binding of a fluorescent antagonist to a defined receptor in a cell and if an associated decrease in biological response is observed, then the test compound is a potential inverse agonist.

5. A HCS assay as claimed in claim 1 wherein if the test compound inhibits the binding of a fluorescent antagonist to a defined receptor in a cell and if no associated change in biological response is observed, then the test compound is a potential antagonist.

6. A HCS assay as claimed in claim 1 wherein if the test compound inhibits the binding of a fluorescent antagonist to a defined receptor in a cell and if an associated increase in biological response is observed, then the test compound is a potential agonist.

7. A HCS assay of claim 4 wherein which the binding of a fluorescent antagonist is to be inhibited, and the assay is conducted in a constitutively active receptor system, wherein a receptor is overexpressed, in which the cellular biological response will produce a stimulated response in the absence of any added agonist, antagonist or compound to be tested.

8. A HCS assay of claim 1 additionally further comprising a readout of information relating to morphology of cells, gene transcription and toxicity.

9. A HCS assay of claim 1 wherein the binding of the fluorescent agonist is detected with one particular fluorescent wavelength and its associated biological response is monitored in the same cell by a separate readout.

10. A HCS assay of claim 1 for the pharmacological analysis of ligands for drug targets wherein the ligands are G-protein-coupled receptors (GPCR).

11. A HCS assay of claim 1 conducted in ultra-high-throughput assays involving multiwell plates or in plasma membrane microdomains of a single living cell.

12. A HCS assay of claim 1 wherein inhibition or binding is direct or indirect, and one or more compounds inhibit or bind a cell or cell material which interacts with the primed cell or cell material thereby eliciting or suppressing a response from the primed cell or cell material.

13. A HCS assay of claim 1 wherein the detection of a sensor response indicates the one or more compounds is an agonist, and in contrast the suppression of a sensor response indicates the one or more compounds is an antagonist or the detection of a reduced basal sensor response indicates that one or more compounds is an inverse agonist.

14. A HCS assay as claimed in claim 13 wherein the detection of fluorescent agonist fluorescence indicates the one or more compounds does not inhibit binding of the cell or cell material by the fluorescent agonist and in contrast the suppression of fluorescent agonist fluorescence indicates the one or more compounds inhibits binding of the cell or cell material by the fluorescent agonist.

15. A HCS assay of claim 1 which is homogeneous, conducted in a single phase.

16. A HCS assay of claim 1 wherein a sensor is selected from a fluorescent, chemiluminescent or luminescent entity or a reporter gene which is sensitive to a biological response to be investigated, including a fluorescent or luminescent dye which is pH sensitive or voltage sensitive.

17. A HCS assay as claimed in claim 16 wherein a sensor is a fluorescent dye of different wavelength to the fluorescent agonist enabling spectral resolution of the sensor and agonist.

18. A HCS assay of claim 1 wherein a fluorescent agonist or fluorescent antagonist is identified by a method for determining the functional response or pharmacological properties of a fluorescent ligand, comprising:
a) priming a cell or cell material with a sensor for a biological response;
b) subsequently contacting with a fluorescent ligand
wherein the binding of the fluorescent ligand and its associated biological response are detected or monitored in the same cell and are distinct allowing separate readout, and wherein if binding, and thereby fluorescence, of the fluorescent ligand is detected, and if the associated measurable biological response from the cell or cell material is maintained this indicates that the fluorescent ligand is a potential agonist, and if binding, and thereby fluorescence, of the fluorescent ligand is detected but the associated measurable biological response from the cell or the cell material is reduced or is absent, this indicates that the fluorescent ligand is a potential neutral antagonist or inverse agonist.

19. A HCS assay of claim 1 wherein a cell or cell material comprises live cell material, including individual cells or sub cell compartments, selected from GPCRs in living cells, membrane containing these proteins, solubilised receptors or GPCR arrays.

20. A HCS assay of claim 1 which includes detecting a change in the intensity, excitation or emission wavelength distribution of fluorescence (single and multi photon), fluorescence lifetime, fluorescence polarisation or a combination thereof.

21. A HCS assay as claimed in claim 20 wherein the spectral characteristics of the one or more compounds and the fluorescent agonist are selected to allow optimum two-colour cross-correlation fluorescence correlation spectroscopy or confocal microscopy, which may be single or multiphoton.

22. A fluorescent histamine receptor agonist or fluorescent histamine receptor antagonist selected from red absorbing BODIPY derivatives of GPCR ligands wherein the ligand is selected from the formula $R^h R^{h1} R^{h2} L.h$ wherein $R^h$ is selected from $C_{1-20}$ hydrocarbyl including one or more heteroaryl, aryl, cycloaryl, heterocyclyl optionally together with or substituted by or including one or more heteroatoms or halo such as O, N, Cl $R^{h1}$ is selected from $C_{0-4}$ alkyl $R^{h2}$ is a single bond or is selected from —$NR^{h3}$—, —$H^1C(=H^2)NH$— or

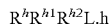

wherein $H^1$ is $NR^{h3}$ or O or S and $H^2$ is selected from —HN, —O and —S and wherein $R^{h3}$ is selected from H, $C_{1-3}$ alkyl such as $CH_3$ and CN and $R^{h4}$ is selected from a single bond, $C_{1-6}$ ether or etheramide Or $R^{h2}$ is selected from $HNC(=NR^{h3})NH$, $OCH_2C(=O)NH$, $SC(=NH)NH$,

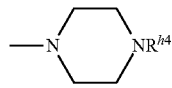

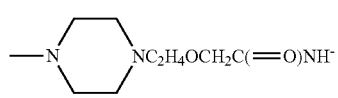

L.h comprises linking functionality $J_T$ which is amino, and linker linker L which is selected from $C_{1-12}$ straight chain alkyl, $C_{6-12}$ cycloalkyl or aryl and combinations thereof optionally comprising one or more heteroatoms O and optionally substituted by $C_1$ aliphatic.

23. A novel fluorescent agonist or fluorescent antagonist as claimed in claim 22 wherein $R^h$ is selected from the following structures

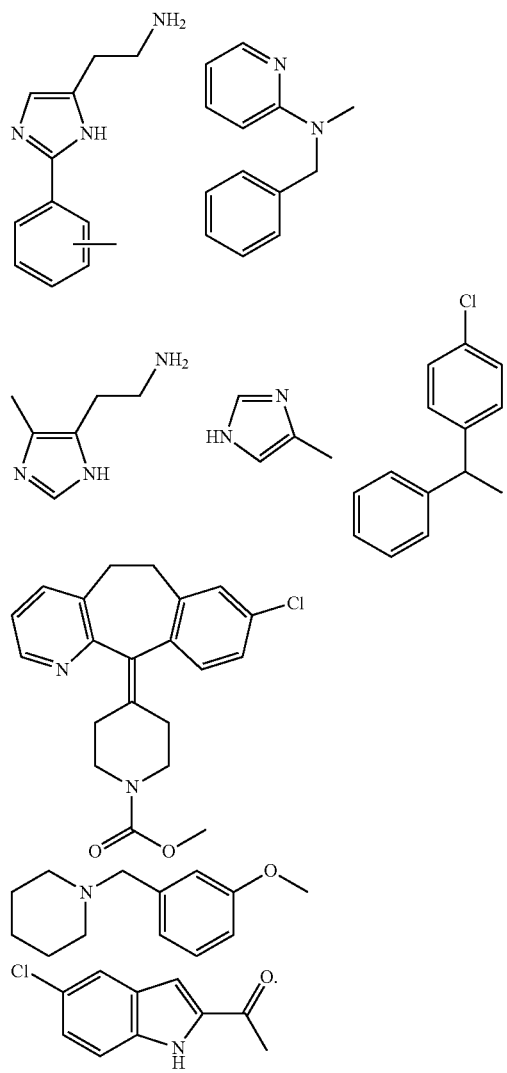

24. A HCS assay of claim 5 wherein the binding of a fluorescent antagonist is to be inhibited, and the assay is conducted in a constitutively active receptor system, wherein a receptor is overexpressed, in which the cellular biological response will produce a stimulated response in the absence of any added agonist, antagonist or compound to be tested.

25. A HCS assay of claim 6 wherein the binding of a fluorescent antagonist is to be inhibited, and the assay is conducted in a constitutively active receptor system, wherein a receptor is overexpressed, in which the cellular biological response will produce a stimulated response in the absence of any added agonist, antagonist or compound to be tested.

26. A HCS assay according to claim 1, wherein the Flurocent moiety of the fluorescent agonist or fluorescent antagonist comprises BODIPY™ 630/650 or analogues thereof.

27. A fluorescent histamine receptor agonist or fluorescent histamine receptor antagonist of claim 22 selected from the following compounds including their single enantiomers, (R, S), enantiomer pairs and racemic mixtures:

2-(2,3 or 4-aminoethylphenyl)histamine BODIPY 630/ 650X (AEPH BY630X), APrPH BY630X, ABPH BY630X, APPH BY630X, AHxPH BY630X, AHPH BY630X, AOPH BY630X, ANPH BY630X, 2-(2,3 or 4-aminoethylphenyl)histamine BODIPY 630/650

(AEPH BY630), APrPH BY630, ABPH BY630, APPH BY630, AHxPH BY630, AHPH BY630, AOPH BY630, ANPH BY630, AdOOH BY630X, AdOOH BY630, Desmethylaminoethyl Mepyramine BODIPY 630/650X (DMAEM BY630X), DMAPrM BY630X, DMABM BY630X, DMAPM BY630X, DMAHxM BY630X, DMAHM BY630X, DMAOM BY630X, DMANM BY630X, Desmethylaminoethyl Mepyramine BODIPY 630/650 (DMAEM BY630), DMAPrM BY630, DMABM BY630, DMAPM BY630, DMAHxM BY630, DMAHM BY630, DMAOM BY630, DMANM BY630, DMAdOO BY630X, DMAdOO BY630, 4-aminoethylhistamine BODIPY 630/650X (AEH BY630X), APrH BY630X, ABH BY630X, APH BY630X, AHxH BY630X, AHH BY630X, AOH BY630X, ANH BY630X, 4-aminoethylhistamine BODIPY 630/650 (AEH BY630), APrH BY630, ABH BY630, APH BY630, AHxH BY630, AHH BY630, AOH BY630, ANH BY630, AdOO BY630X, AdOO BY630, 1-(3-(1H-imidazol-4-yl)propyl)-3-aminoethyl guanidine BODIPY 630/650X (IPAEG BY603X), IPAPrG BY630X, IPABG BY630X, IPAPG BY630X, IPAHxG BY630X, IPAHG BY630X, IPAOG BY630X, IPANG BY630X, IPAEG BY603, IPAPrG BY630, IPABG BY630, IPAPG BY630, IPAHxG BY630, IPAHG BY630, IPAOG BY630, IPANG BY630, IPAdOOG BY630X, IPAdOOG BY630, Cetirizine aminoethylamide BODIPY 630/650X (CAEA BY630X), CAPrA BY630X, CABA BY630X, CAPA BY630X, CAHxA BY630X, CAHA BY630X, CAOA BY630X, CANA BY630X, CAEA BY630, CAPrA BY630, CABA BY630, CAPA BY630, CAHxA BY630, CAHA BY630, CAOA BY630, CANA BY630, CAdOOA BY630X, CAdOOA BY630, Aminoloratidine BODIPY 630/650X (AL BY630X), AML BY630X, AEL BY630X, APrL BY630X, ABL BY630X, APL BY630X, AHxL BY630X, AHL BY630X, AL BY630, AML BY630, AEL BY630, APrL BY630, ABL BY630, APL BY630, AHxL BY630, AHL BY630, AdOHxL BY630X, AdOHxL BY630, 3-Aminoethyl-2-cyano-1-(3-(3-(piperidin-1-ylmethyl)phenoxy)propyl)guanidine BODIPY 630/650X (AECPG BY603X), APrCPG BY630X, ABCPG BY630X, APCPG BY630X, AHx-CPG BY630X, AHCPG BY630X, AOCPG BY630X, ANCPG BY630X, AECPG BY630, APrCPG BY630, ABCPG BY630, APCPG BY630, AHxCPG BY630, AHCPG BY630, AOCPG BY630, ANCPG BY630, AdOOCPG BY630X, AdOOCPG BY630, 3-(1H-imidazol-4- yl)propyl 2-aminoethylcarbamimidothioate BODIPY 630/650X (IAET BY630X), IAPrT BY630X, IABT BY630X, IAPT BY630X, IAHxT BY630X, IAHT BY630X, IAOT BY630X, IANT BY630X, IAET BY630, IAPrT BY630, IABT BY630, IAPT BY630, IAHxT BY630, IAHT BY630, IAOT BY630, IANT BY630, IAdOOT BY630X, IAdOOT BY630, Aminomethyl-JNJ 7777120 BODIPY 630/650X, Aminoethyl-JNJ 7777120 BODIPY 630/650X, Aminopropyl-JNJ 7777120 BODIPY 630/650X, Aminobutyl-JNJ 7777120 BODIPY 630/650X, Aminopentyl-JNJ 7777120 BODIPY 630/650X, Aminohexyl-JNJ 7777120 BODIPY 630/650X, Aminoheptyl-JNJ 7777120 BODIPY 630/650X, Aminooctyl-JNJ 7777120 BODIPY 630/650X, Aminomethyl-JNJ 7777120 BODIPY 630/650, Aminoethyl-JNJ 7777120 BODIPY 630/650, Aminopropyl-JNJ 7777120 BODIPY 630/650, Aminobutyl-JNJ 7777120 BODIPY 630/650, Aminopentyl-JNJ 7777120 BODIPY 630/650, Aminohexyl-JNJ 7777120 BODIPY 630/650, Aminoheptyl-JNJ 7777120 BODIPY 630/650, Aminooctyl-JNJ 7777120 BODIPY 630/650, Amino-3,6-dioxoheptane-JNJ 7777120 BODIPY 630/650X, Amino-3,6-dioxoheptane-JNJ 7777120 BODIPY 630/650.

28. A HCS assay as claimed in claim 16 wherein a sensor is selected from a sensor for monitoring changes in membrane potential in response to agonist stimulation, a sensor for monitoring changes in intracellular free calcium, a sensor for monitoring stimulation of intracellular signalling pathways and a sensor for monitoring changes in cyclic AMP and intracellular free calcium.

29. A HCS assay as claimed in claim 16 wherein a sensor is selected from a fluorescent dye such as a thiocarbocyanine fluorescent dye (Invitrogen), a calcium sensitive fluorescent dye, a reporter gene under the control of specific response elements and a chameleon fluorescent sensor which makes use of FRET-based signals.

\* \* \* \* \*